US008691830B2

(12) United States Patent
Tavares et al.

(10) Patent No.: US 8,691,830 B2
(45) Date of Patent: Apr. 8, 2014

(54) CDK INHIBITORS

(71) Applicant: G1 Therapeutics, Inc., Chapel Hill, NC (US)

(72) Inventors: Francis X. Tavares, Durham, NC (US); Jay C. Strum, Hillsborough, NC (US)

(73) Assignee: G1 Therapeutics, Inc., Chapel Hill, NC (US)

( * ) Notice: Subject to any disclaimer, the term of this patent is extended or adjusted under 35 U.S.C. 154(b) by 0 days.

(21) Appl. No.: 13/869,594

(22) Filed: Apr. 24, 2013

(65) Prior Publication Data

US 2013/0237534 A1 Sep. 12, 2013

Related U.S. Application Data

(63) Continuation of application No. PCT/US2011/057749, filed on Oct. 25, 2011.

(60) Provisional application No. 61/406,498, filed on Oct. 25, 2010.

(51) Int. Cl.
*A01N 43/90* (2006.01)
*A01N 43/66* (2006.01)

(52) U.S. Cl.
USPC ........................................ 514/265.1; 544/244

(58) Field of Classification Search
None
See application file for complete search history.

(56) References Cited

U.S. PATENT DOCUMENTS

2004/0236084 A1 11/2004 Biwersi et al.

FOREIGN PATENT DOCUMENTS

| WO | WO 99/15500 A1 | 4/1999 |
| WO | WO 03/062236 A1 | 7/2003 |
| WO | WO 2005/040166 A1 | 5/2005 |
| WO | WO 2005/052147 A2 | 6/2005 |
| WO | WO 2005/105213 A2 | 11/2005 |
| WO | WO 2007/048847 A2 | 5/2007 |
| WO | WO 2009/003003 A2 | 12/2008 |
| WO | WO 2009/085185 A1 | 7/2009 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/103485 A2 | 8/2011 |

OTHER PUBLICATIONS

Presser, Armin and Antje Hüfner "Trimethylsilyldiazomethane—A Mild and Efficient Reagent for the Methylation of Carboxylic Acids and Alcohols in Natural Products" Monatshefte für Chemie, 2004, vol. 135, Issue 8, pp. 1015-1022.

Schönauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983, vol. 24, pp. 573-576.

White, J.D. et al. "Transformations of Quinic Acid. Asymmetric Synthesis and Absolute Configuration of Mycosporin I and Mycosporin-gly" Journal of Organic Chemistry, 1995, vol. 60, Issue 12, pp. 3600-3611.

Guillard et al., "Synthesis and biological evaluations of new pyrrolo[2,3-b]pyrimidine as SDI analogs," Heterocyles, vol. 75(5), 2008, 1163-1189.

*Primary Examiner* — James O Wilson
*Assistant Examiner* — Oluwafemi Masha
(74) *Attorney, Agent, or Firm* — Knowles Intellectual Property Strategies, LLC

(57) ABSTRACT

Compounds of formulae I, II or III, and pharmaceutically acceptable salts thereof, are useful as CDK inhibitors.

42 Claims, 8 Drawing Sheets

CDK INHIBITORS

STATEMENT OF RELATED APPLICATIONS

This application is a continuation of International Application No. PCT/US2011/057749 filed Oct. 25, 2011, which is related to and claims the benefit of provisional U.S. Application No. 61/406,498 filed Oct. 25, 2010. The entirety of each of these applications is hereby incorporated by reference for all purposes.

STATEMENT REGARDING FEDERALLY SPONSORED RESEARCH OR DEVELOPMENT

This invention was made with government support under Grant No. 5R44AI084284 awarded by the National Institutes of Allergy and Infectious Disease. The government has certain rights in the invention.

FIELD OF THE INVENTION

The invention relates to compounds useful for inhibiting cyclin-dependent kinase ("CDK").

BACKGROUND

Cancer continues to be a challenge for modern medicine. At a basic level, cancer occurs when there is uncontrollable cell division. The uncontrollable cell division is an effect of a break down in the natural life cycle of cells. CDK is a family of kinases involved in the cell life cycle. Abnormally high CDK activity is one characteristic of several cancers. There are naturally occurring CDK-inhibiting proteins and the abnormally high CDK activity maybe due to a malfunction of the naturally occurring CDK inhibitors or due to an overabundance of CDK. CDK inhibitors are known in the art but there remains a need for additional CDK inhibitors.

SUMMARY

The invention is directed to compounds of formula I, II or III:

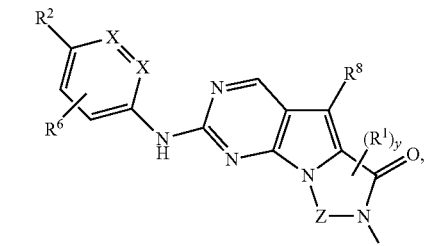

I

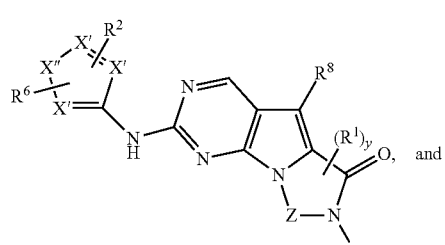

II

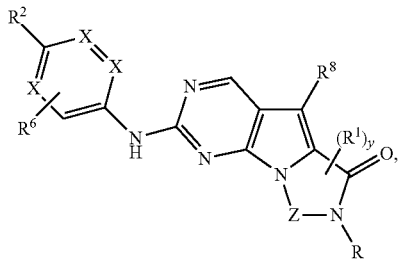

III wherein R, $R^1$, $R^2$, $R^6$, $R^8$, X, X', X", Z and y are as defined herein and to pharmaceutically acceptable salts thereof.

The disclosed compounds are useful as CDK inhibitors and could be useful in the treatment of diseases and disorders mediated by CDK such as cancer. Pharmaceutical compositions comprising the compounds and pharmaceutically acceptable salts of the compounds are also disclosed.

DETAILED DESCRIPTION

Figure 1:
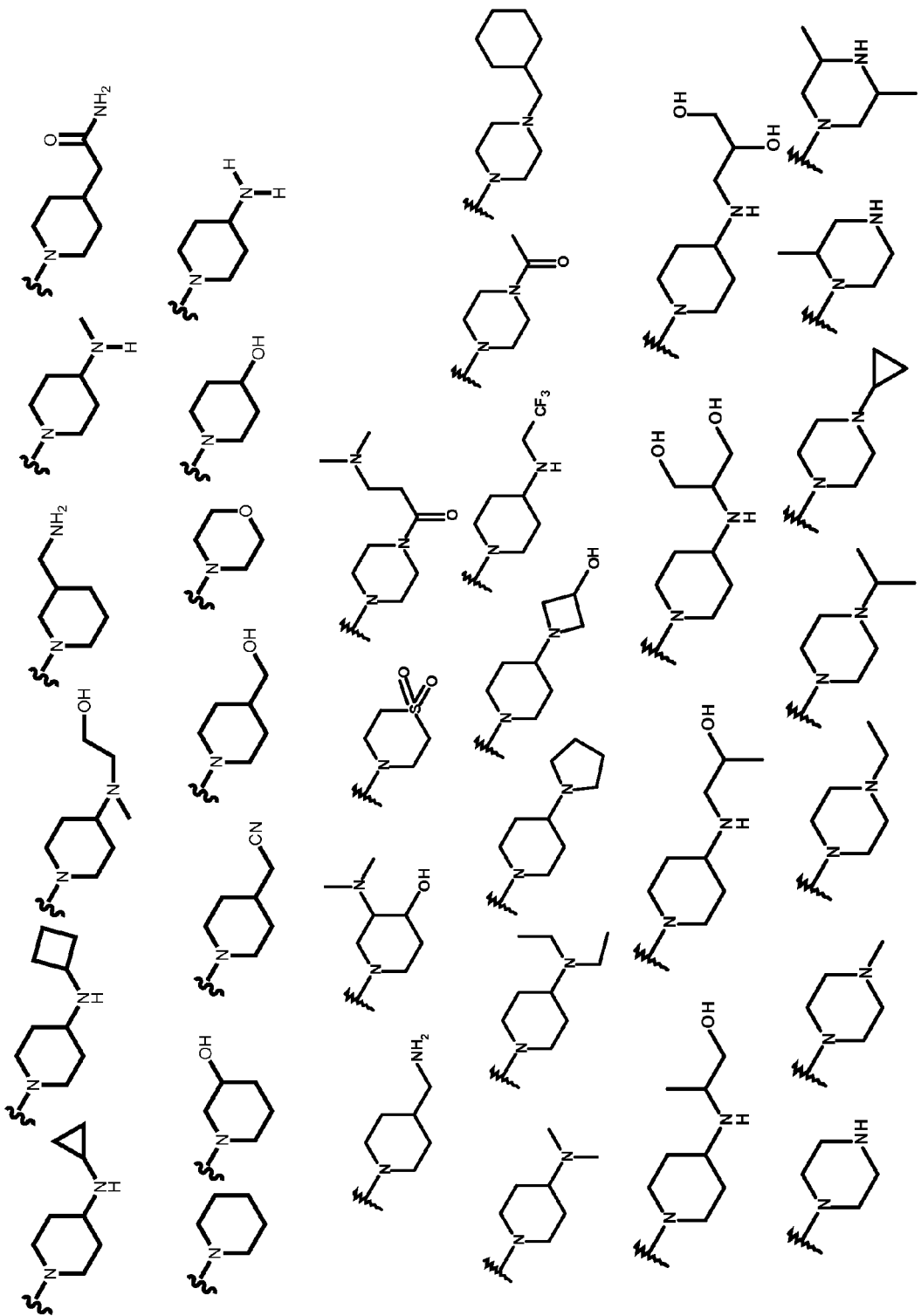
FIGS. 1-3 illustrate embodiments of $R^2$ of the compounds of the invention.

In one embodiment, compounds of formula I and II are provided:

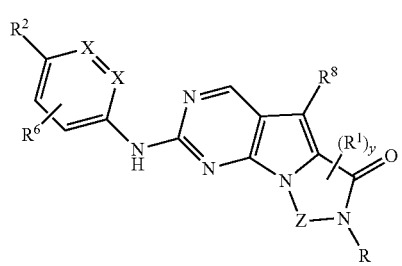

I

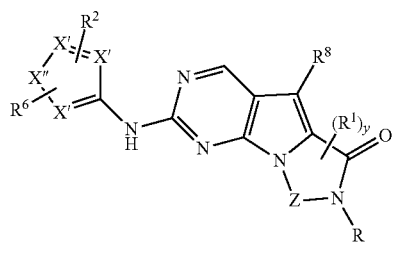

II wherein:
Z is —$(CH_2)_x$— wherein x is 1, 2, 3 or 4 or —O—$(CH_2)_z$— wherein z is 2, 3 or 4;
each X is independently CH or N;
each X' is independently, CH or N;
X" is $CH_2$, S or NH;
each of R and $R^8$ are independently H, $C_1$-$C_3$ alkyl or haloalkyl;
each $R^1$ is independently aryl, alkyl, cycloalkyl or haloalkyl, wherein each of said alkyl, cycloalkyl and haloalkyl groups optionally includes O or N heteroatoms in place of a carbon in the chain and two $R^1$'s on adjacent ring atoms or on the same ring atom together with the ring atom(s) to which they are attached optionally form a 3-8-membered cycle;

y is 0, 1, 2, 3 or 4;

$R^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-C(O)—O-alkyl; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring and wherein m is 0 or 1 and n is 0, 1 or 2;

$R^3$ and $R^4$ at each occurrence are independently:
  (i) hydrogen or
  (ii) alkyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance, and wherein two R$^x$ groups bound to the same or adjacent atom may optionally combine to form a ring; or R$^3$ and R$^4$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;

$R^5$ and $R^{5*}$ at each occurrence is:
  (i) hydrogen or
  (ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance;

$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-O-alkylene-OR$^5$, -(alkylene)$_m$-S(O)$_n$—R$^5$, -(alkylene)$_m$-NR$^3$R$^4$, -(alkylene)$_m$-CN, -(alkylene)$_m$C(O)—R$^5$, -(alkylene)$_m$C(S)—R$^5$, -(alkylene)$_m$-C(O)—OR$^5$, -(alkylene)$_m$-O—C(O)—R$^5$, -(alkylene)$_m$-C(S)—OR$^5$, -(alkylene)$_m$-C(O)-(alkylene)$_m$-NR$^3$R$^4$, -(alkylene)$_m$-C(S)—NR$^3$R$^4$, -(alkylene)$_m$-N(R$^3$)—C(O)—NR$^3$R$^4$, -(alkylene)$_m$-N(R$^3$)—C(S)—NR$^3$R$^4$, -(alkylene)$_m$-N(R$^3$)—C(O)—R$^5$, -(alkylene)$_m$-N(R$^3$)—C(S)—R$^5$, -(alkylene)$_m$-O—C(O)—NR$^3$R$^4$, -(alkylene)$_m$-O—C(S)—NR$^3$R$^4$, -(alkylene)$_m$-SO$_2$—NR$^3$R$^4$, -(alkylene)$_m$-N(R$^3$)—SO$_2$—R$^5$, -(alkylene)$_m$-N(R$^3$)—SO$_2$—NR$^3$R$^4$, -(alkylene)$_m$-N(R$^3$)—C(O)—OR$^5$) -(alkylene)$_m$-N(R$^3$)—C(S)—OR$^5$, or -(alkylene)$_m$-N(R$^3$)—SO$_2$—R$^5$; wherein:
  said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$OR$^{5*}$, -(alkylene)$_m$-S(O)$_n$—R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)OR$^{5*}$, -(alkylene)$_m$-OC(=O)R$^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO$_2$—NR$^{3*}$R$^{4*}$, -(alkylene)$_m$-N(R$^{3*}$)—SO$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$*N(R$^{3*}$)—C(S)—OR$^{5*}$, or -(alkylene)$_m$-N(R$^{3*}$)—SO$_2$—R$^{5*}$, n is 0, 1 or 2, and m is 0 or 1;

$R^{3*}$ and $R^{4*}$ at each occurrence are independently:
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance; or R$^{3*}$ and R$^{4*}$ together with the nitrogen atom to which they are attached may combine to form a heterocyclo ring optionally independently substituted with one or more R$^x$ groups as allowed by valance; and $R^6$ is H or lower alkyl, or a pharmaceutically acceptable salt thereof.

In some aspects, the compound is of formula I or formula II and $R^6$ is absent.

In some aspects, the compound is of formula III:

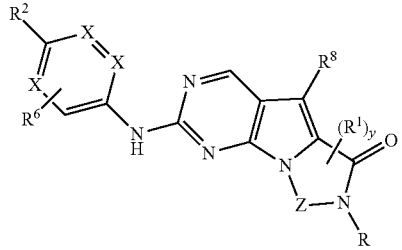

and the variables are as defined for compounds of formulae I and II and pharmaceutically acceptable salts thereof.

In some aspects, R$^x$ is not further substituted.

In some aspects, R$^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring and wherein m is 0 or 1 and n is 0, 1 or 2.

In some aspects, R$^8$ is hydrogen or C$_1$-C$_3$ alkyl.

In some aspects, R is hydrogen or C$_1$-C$_3$ alkyl.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ any of which may be optionally independently substituted with one or more R$^x$ groups as allowed by valance, and wherein two R$^x$ groups bound to the same or adjacent atom may optionally combine to form a ring.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ without further substitution.

In some aspects, m in R$^2$ is 1. In a further aspect, the alkylene in R$^2$ is methylene.

In some aspects, $R^2$ is

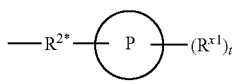

wherein:
$R^{2*}$ is a bond, alkylene, -(alkylene)$_m$-O-(alkylene)$_m$-, -(alkylene)$_m$-C(O)-(alkylene)$_m$-, -(allylene)$_m$-S(O)$_2$-(alkylene)$_m$- and -(alkylene)$_m$-NH-(alkylene)$_m$- wherein each m is independently 0 or 1;
P is a 4- to 8-membered mono- or bicyclic saturated heterocyclyl group;
each $R^{x1}$ is independently -(alkylene)$_m$-(C(O))$_m$-(alkylene)$_m$-(N($R^N$))$_m$-(alkyl)$_m$ wherein each m is independently 0 or 1 provided at least one m is 1, —(C(O))—O-alkyl, -(alkylene)$_m$-cycloalkyl wherein m is 0 or 1, —N($R^N$)-cycloalkyl, —C(O)-cycloalkyl, -(alkylene)$_m$-heterocyclyl wherein m is 0 or 1, or —N($R^N$)-heterocyclyl, —C(O)-heterocyclyl, —S(O)$_2$-(alkylene)$_m$ wherein m is 1 or 2, wherein:
$R^N$ is H, $C_1$ to $C_4$ alkyl or $C_1$ to $C_6$ heteroalkyl, and
wherein two $R^{x1}$ can, together with the atoms to which they attach on P, which may be the same atom, form a ring; and
t is 0, 1 or 2.

In some aspects, each $R^{x1}$ is only optionally substituted by unsubstituted alkyl, halogen or hydroxy.

In some aspects, $R^{x1}$ is hydrogen or unsubstituted $C_1$-$C_4$ alkyl.

In some aspects, at least one $R^{x1}$ is -(alkylene)$_m$-heterocyclyl wherein m is 0 or 1.

In some aspects, $R^2$ is

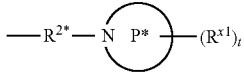

wherein P* is a 4- to 8-membered mono- or bicyclic saturated heterocyclyl group.

In some aspects, $R^2$ is

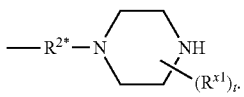

In some aspects, $R^2$ is

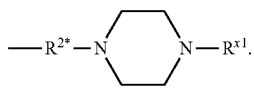

In some aspects, $R^2$ is

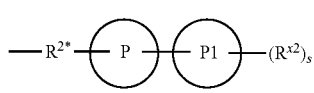

wherein:
$R^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- and -(alkylene)$_m$-NH-(alkylene)$_m$- wherein each m is independently 0 or 1;
P is a 4- to 8-membered mono- or bicyclic saturated heterocyclyl group;
P1 is a 4- to 6-membered monocyclic saturated heterocyclyl group;
each $R^{x2}$ is independently hydrogen or alkyl; and
s is 0, 1 or 2.

In some aspects, $R^2$ is

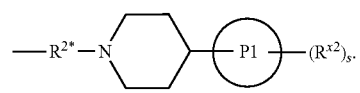

Figure 2:
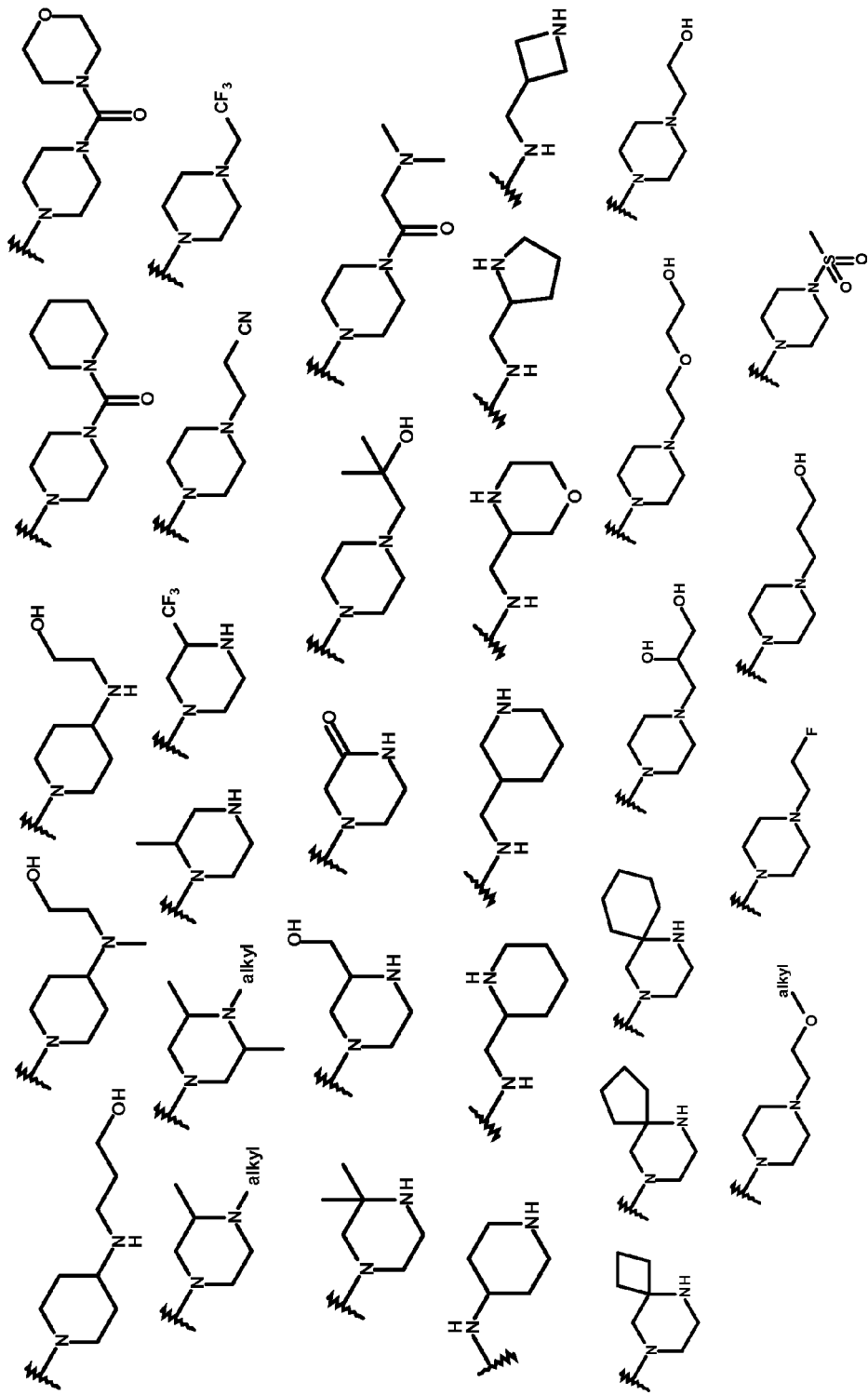
Figure 3:
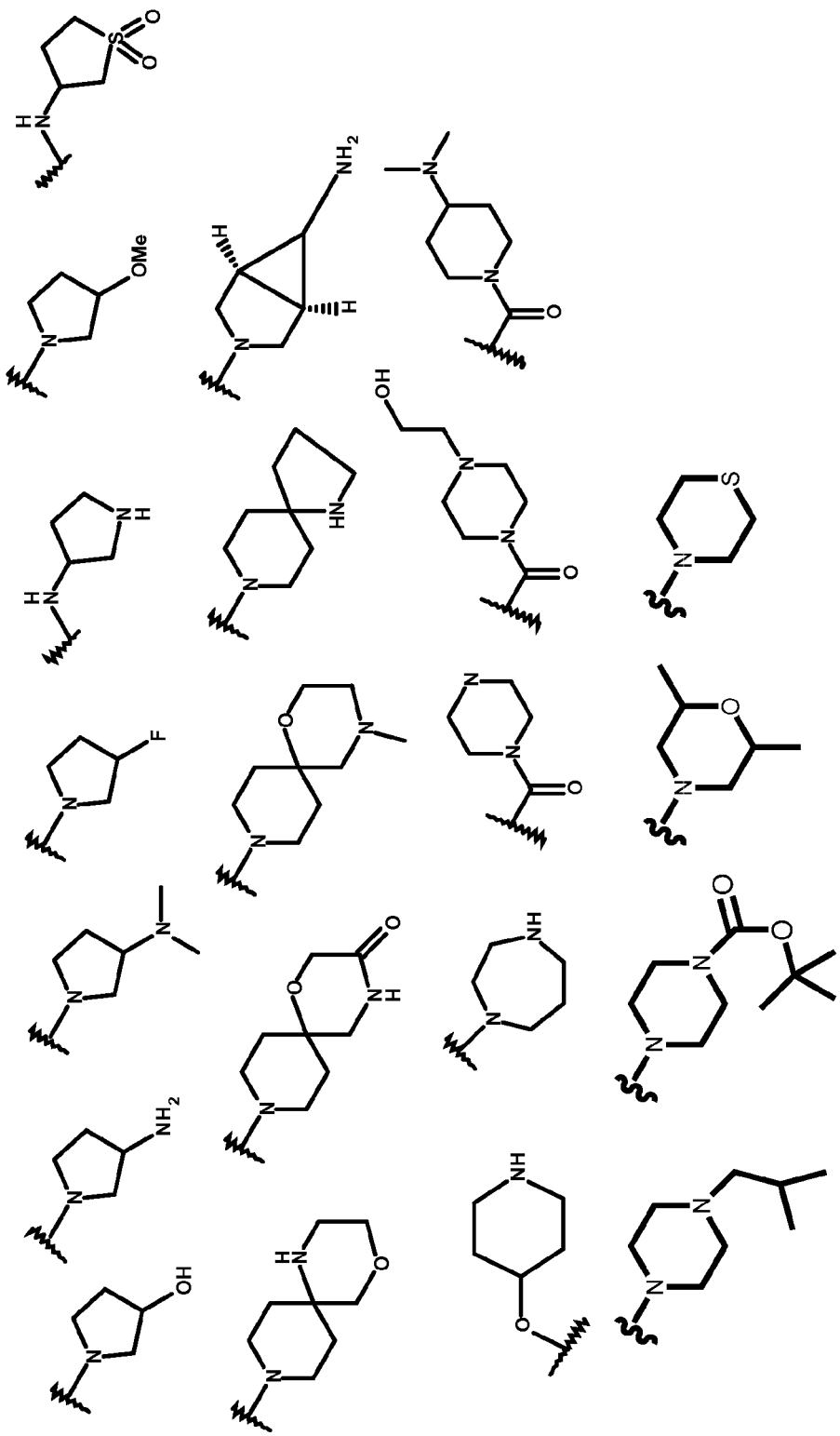
Figure 4:
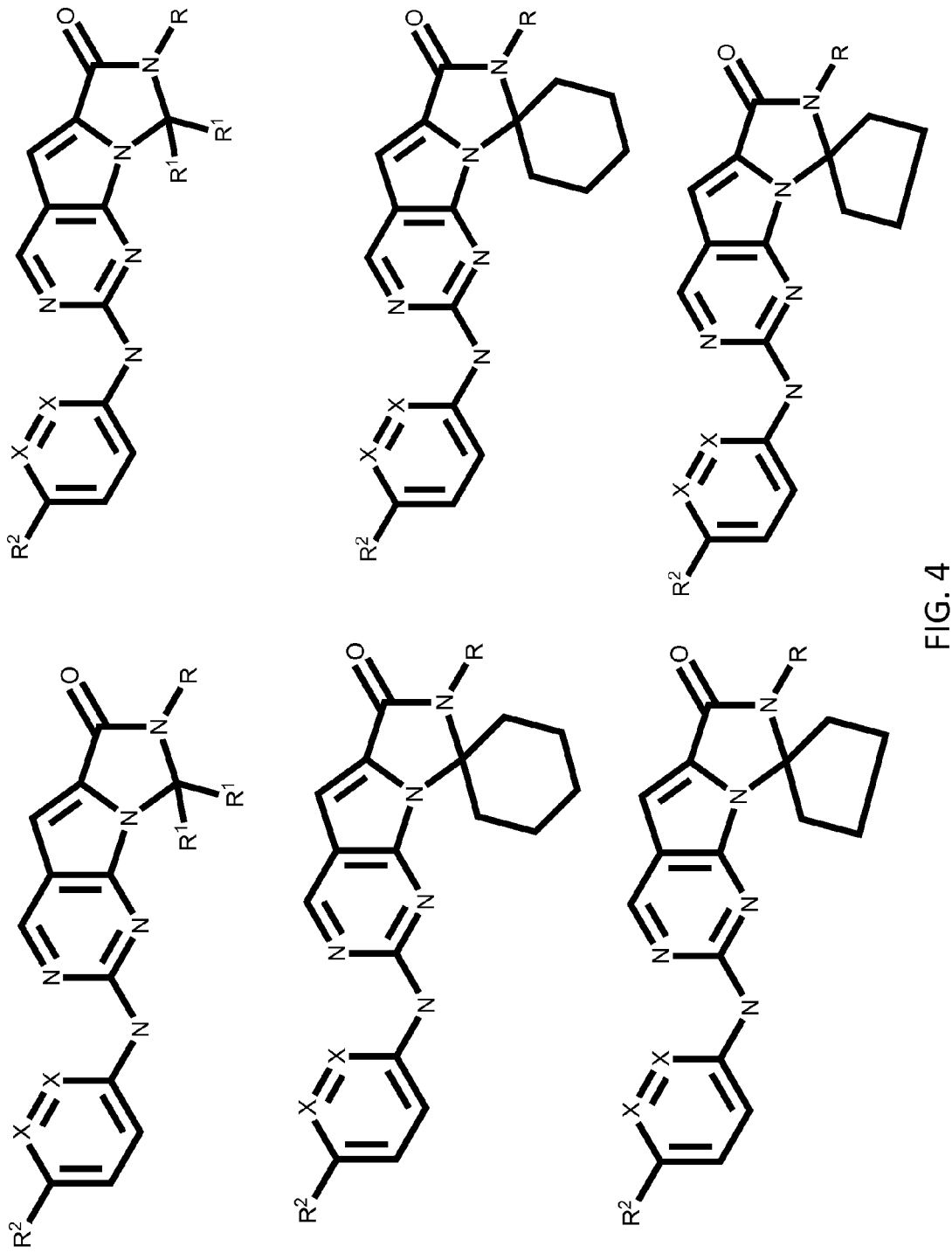
FIGS. 4-8 illustrate embodiments of the core structure of the compounds of the invention.
Figure 5:
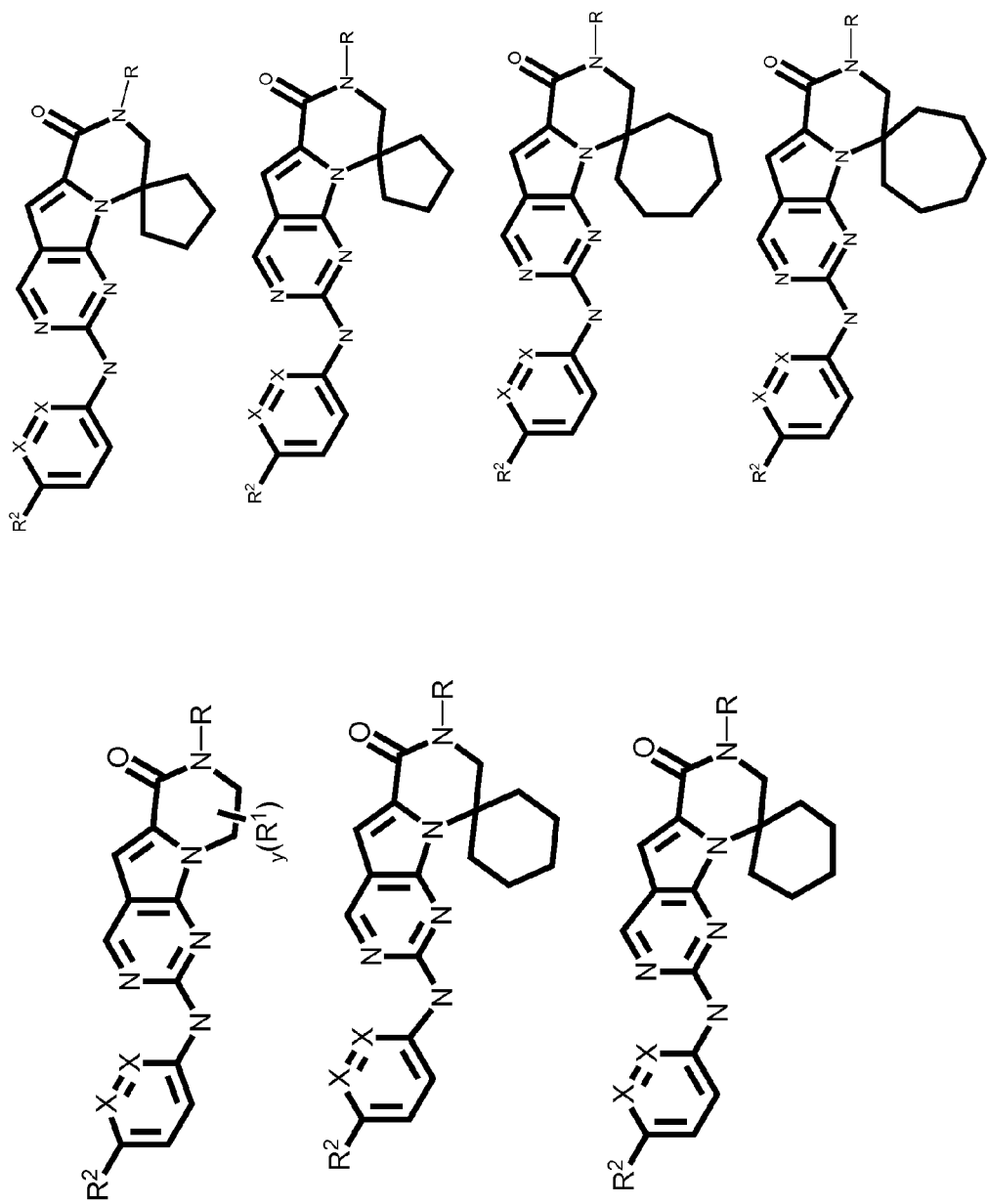
Figure 6:
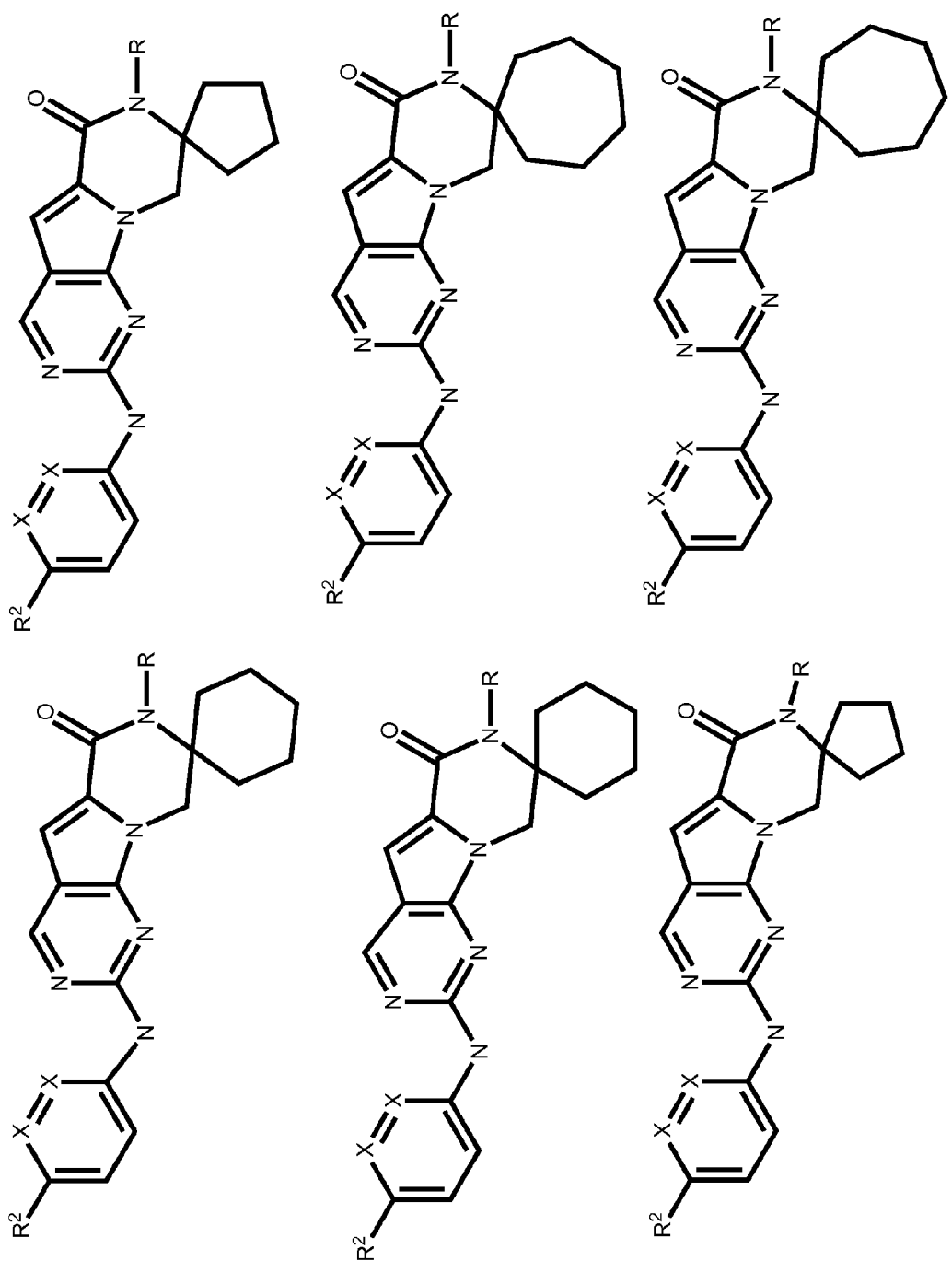
Figure 7:
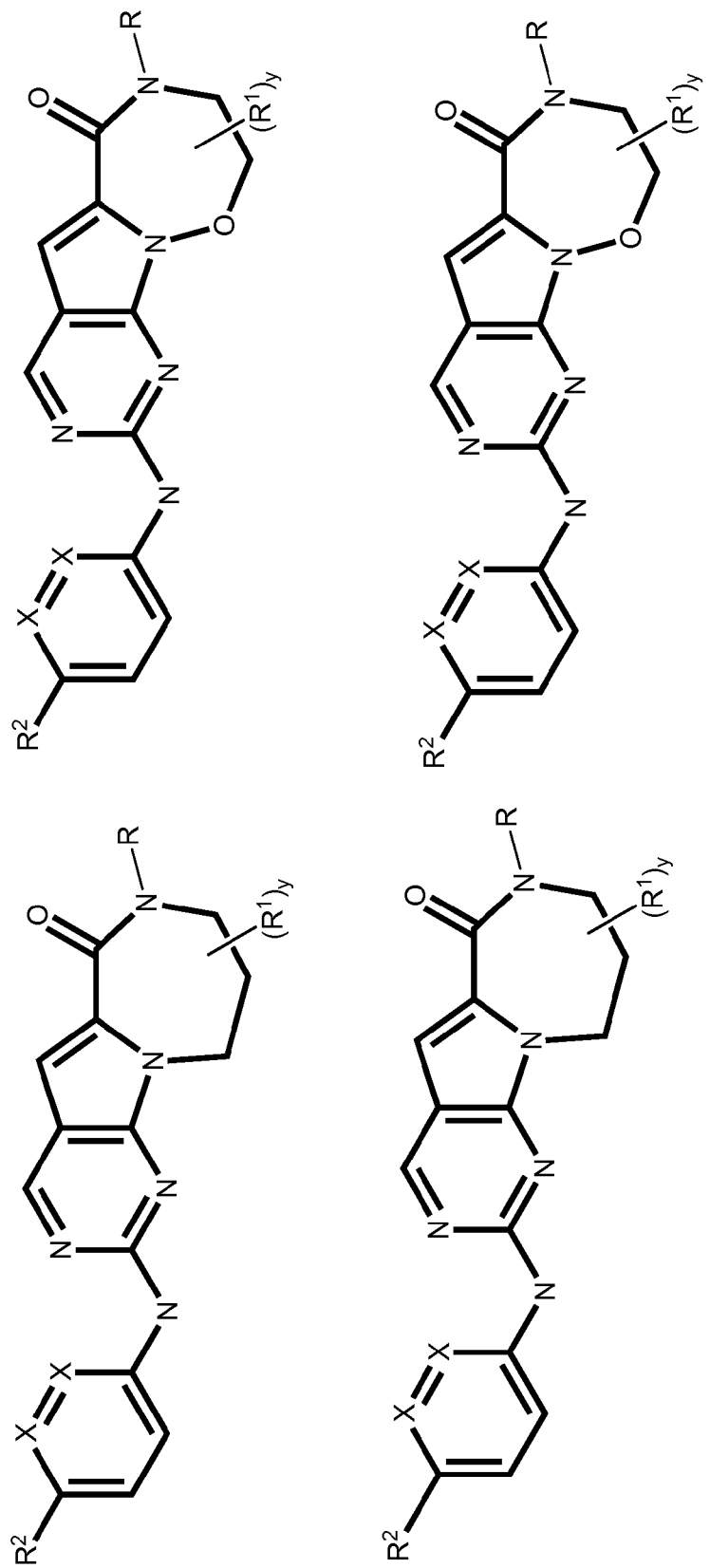
Figure 8:
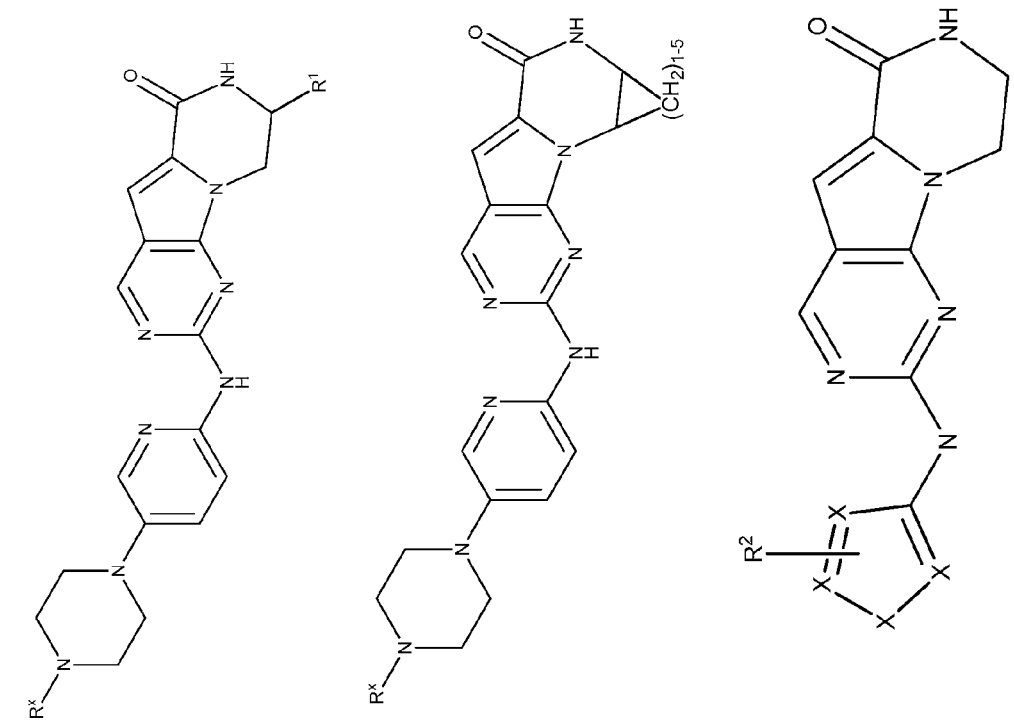
Figure 8:
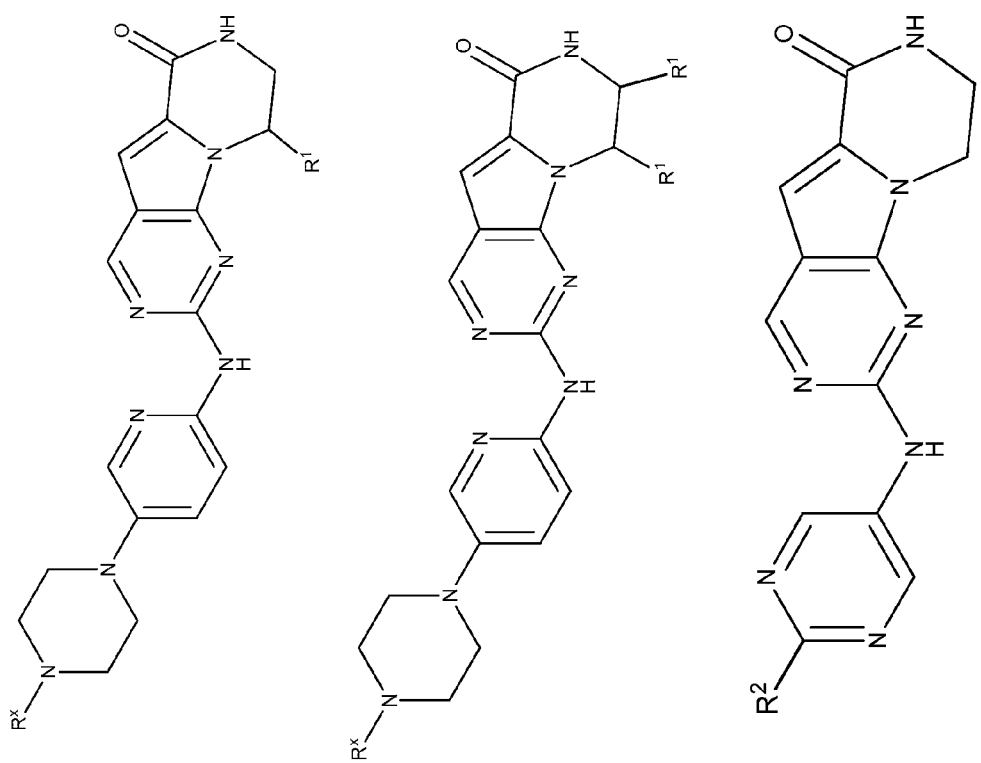

In some aspects, P1 includes at least one nitrogen.
In some aspects, any alkylene in $R^{2*}$ in any previous aspect is not further substituted.
In some aspects, $R^2$ is selected from the structures depicted in FIGS. 1-3.
In some aspects, $R^2$ is

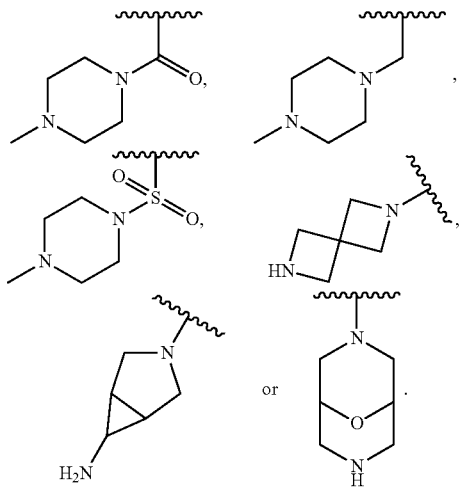

In some aspects, the compound has general formula I and more specifically one of the general structures in FIGS. 4-8 wherein the variables are as previously defined.

In some aspects, the compound has general formula Ia:

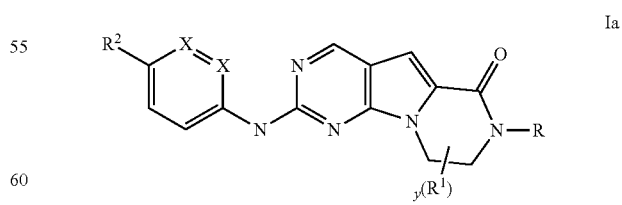

Ia wherein $R^1$, $R^2$, R and y are as previously defined.
In some embodiments, the compound has formula Ia and R is alkyl.
In some embodiments, the compound has formula Ia and R is H.

In some embodiments, the compound has formula Ia and $R^2$ is

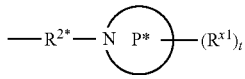

wherein P* is a 4- to 8-membered mono- or bicyclic saturated heterocyclyl group and $R^{2*}$, $R^{x1}$ and t are as previously defined.

In some embodiments, the compound has formula Ia and $R^2$ is

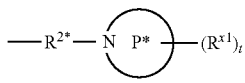

wherein P* is a 4- to 8-membered mono- or bicyclic saturated heterocyclyl group, $R^{x1}$ is hydrogen or unsubstituted $C_1$-$C_4$ alkyl and $R^{2*}$ is as previously defined.

In some embodiments, the compound has formula Ib:

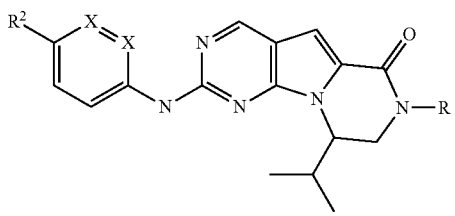

wherein $R^2$ and R are as previously defined.

In some embodiments, the compound has formula Ib and R is alkyl.

In some embodiments, the compound has formula Ib and R is H.

In some embodiments, the compound has formula Ib and $R^2$ is

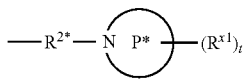

wherein P* is a 4- to 8-membered mono- or bicyclic saturated heterocyclyl group and $R^{2*}$, $R^{x1}$ and t are as previously defined.

In some embodiments, the compound has formula Ib and $R^2$ is

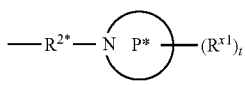

wherein P* is a 4- to 8-membered mono- or bicyclic saturated heterocyclyl group, $R^{11}$ is hydrogen or $C_1$-$C_4$ alkyl and $R^{2*}$ is as previously defined.

In some embodiments, the compound has formula Ic:

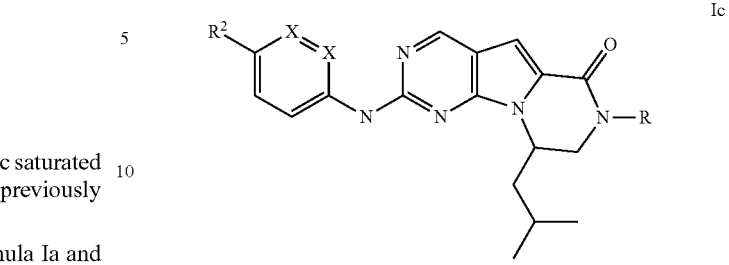

wherein $R^2$ and R are as previously defined.

In some embodiments, the compound has formula Ic and R is alkyl.

In some embodiments, the compound has formula Ic and R is H.

In some embodiments, the compound has formula Ic and $R^2$ is

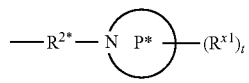

wherein P* is a 4- to 8-membered mono- or bicyclic saturated heterocyclyl group and $R^{2*}$, $R^{x1}$ and t are as previously defined.

In some embodiments, the compound has formula Ic and $R^2$ is

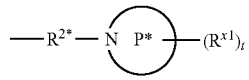

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has formula Id:

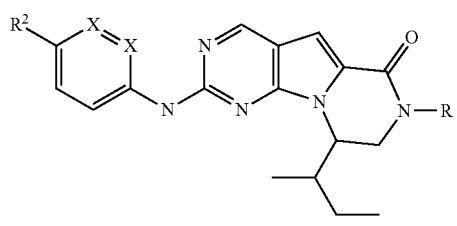

wherein $R^2$ and R are as previously defined.

In some embodiments, the compound has formula Id and R is alkyl.

In some embodiments, the compound has formula Id and R is H.

In some embodiments, the compound has formula Id and $R^2$ is

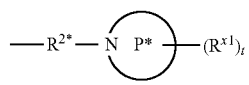

wherein P* is a 4- to 8-membered mono- or bicyclic saturated heterocyclyl group and $R^{2*}$, $R^{x1}$ and t are as previously defined.

In some embodiments, the compound has formula Id and $R^2$ is

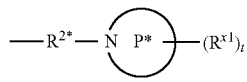

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has formula Ie:

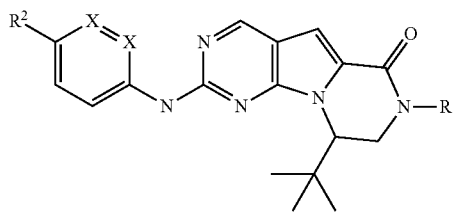

In some embodiments, the compound has formula Ie and R is alkyl.

In some embodiments, the compound has formula Ie and R is H.

In some embodiments, the compound has formula Ie and $R^2$ is

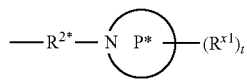

wherein P* is a 4- to 8-membered mono- or bicyclic saturated heterocyclyl group and $R^{2*}$, $R^{x1}$ and t are as previously defined.

In some embodiments, the compound has formula Ie and $R^2$ is

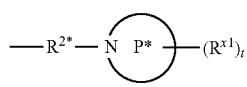

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has formula If:

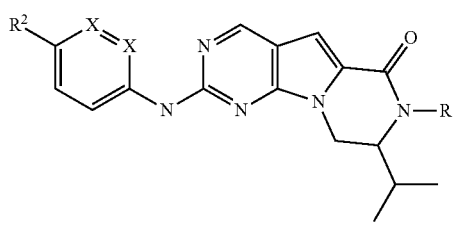

In some embodiments, the compound has formula If and R is alkyl.

In some embodiments, the compound has formula If and R is H.

In some embodiments, the compound has formula If and $R^2$ is

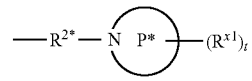

wherein P* is a 4- to 8-membered mono- or bicyclic saturated heterocyclyl group and $R^{2*}$, $R^{x1}$ and t are as previously defined.

In some embodiments, the compound has formula If and $R^2$ is

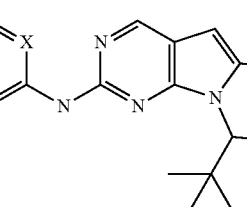

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has formula Ig:

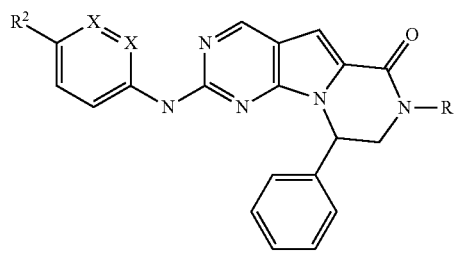

In some embodiments, the compound has formula Ig and R is alkyl.

In some embodiments, the compound has formula Ig and R is H.

In some embodiments, the compound has formula Ig and $R^2$ is

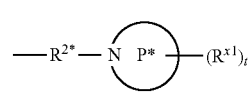

wherein P* is a 4- to 8-membered mono- or bicyclic saturated heterocyclyl group and $R^{2*}$, $R^{x1}$ and t are as previously defined.

In some embodiments, the compound has formula Ig and $R^2$ is

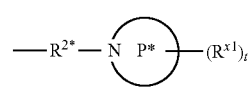

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has formula Ih:

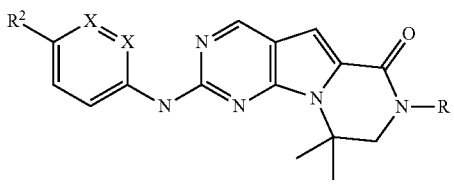

In some embodiments, the compound has formula Ih and R is alkyl.

In some embodiments, the compound has formula Ih and R is H.

In some embodiments, the compound has formula Ih and $R^2$ is

wherein P* is a 4- to 8-membered mono- or bicyclic saturated heterocyclyl group and $R^{2*}$, $R^{x1}$ and t are as previously defined.

In some embodiments, the compound has formula Ih and $R^2$ is

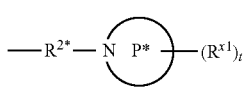

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has formula Ii:

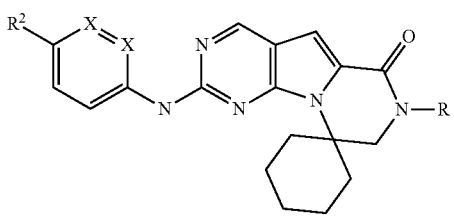

In some embodiments, the compound has formula Ii and R is alkyl.

In some embodiments, the compound has formula Ii and R is H.

In some embodiments, the compound has formula Ii and $R^2$ is

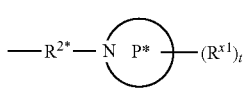

wherein P* is a 4- to 8-membered mono- or bicyclic saturated heterocyclyl group and $R^{2*}$, $R^{x1}$ and t are as previously defined.

In some embodiments, the compound has formula Ii and $R^2$ is

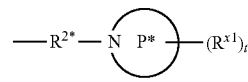

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has formula Ij:

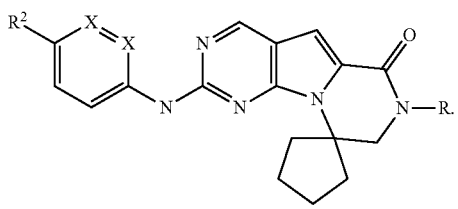

In some embodiments, the compound has formula Ij and R is alkyl.

In some embodiments, the compound has formula Ij and R is H.

In some embodiments, the compound has formula Ij and $R^2$ is

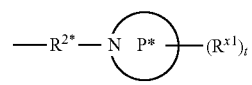

wherein P* is a 4- to 8-membered mono- or bicyclic saturated heterocyclyl group.

In some embodiments, the compound has formula Ij and $R^2$ is

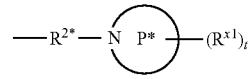

wherein P* is a 4- to 8-membered mono- or bicyclic saturated heterocyclyl group, $R^{x1}$ is hydrogen or $C_1$-$C_4$ alkyl.

In some embodiments, the compound has formula Ij and R is H, and both X are N.

In some embodiments, the compound has formula Ik:

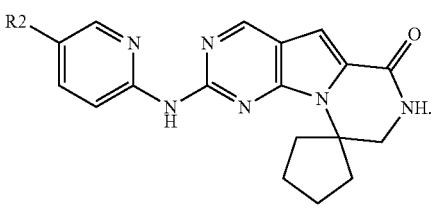

In some embodiments, the compound has formula Ik and R² is

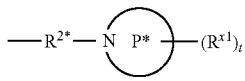

wherein P* is a 4- to 8-membered mono- or bicyclic saturated heterocyclyl group.

In some embodiments, the compound has formula Ik and R² is

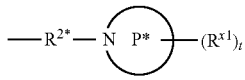

wherein P* is a 4- to 8-membered mono- or bicyclic saturated heterocyclyl group, $R^{x1}$ is hydrogen or $C_1$-$C_4$ alkyl.

In some embodiments, the compound has formula Il:

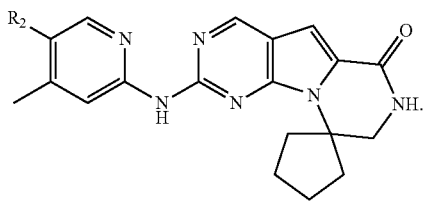

In some embodiments, the compound has formula Il and R² is

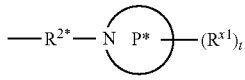

wherein P* is a 4- to 8-membered mono- or bicyclic saturated heterocyclyl group.

In some embodiments, the compound has formula Il and R² is

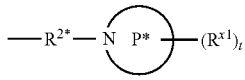

wherein P* is a 4- to 8-membered mono- or bicyclic saturated heterocyclyl group, $R^{x1}$ is hydrogen or $C_1$-$C_4$ alkyl.

In some embodiments, the compound has formula Im:

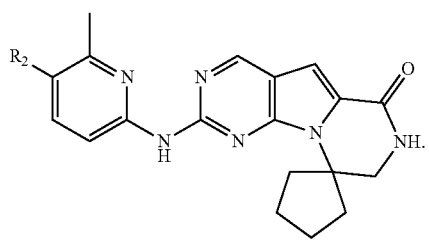

In some embodiments, the compound has formula Im and R² is

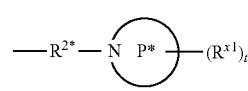

wherein P* is a 4- to 8-membered mono- or bicyclic saturated heterocyclyl group.

In some embodiments, the compound has formula Im and R² is

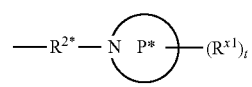

wherein P* is a 4- to 8-membered mono- or bicyclic saturated heterocyclyl group, $R^{x1}$ is hydrogen or $C_1$-$C_4$ alkyl.

In some embodiments, the compound has formula IIa:

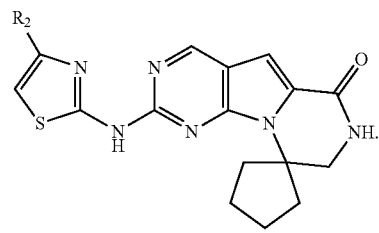

In some embodiments, the compound has formula IIa and R² is

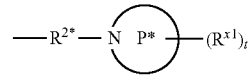

wherein P* is a 4- to 8-membered mono- or bicyclic saturated heterocyclyl group.

In some embodiments, the compound has formula IIa and R² is

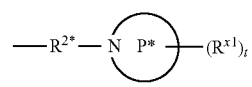

wherein P* is a 4- to 8-membered mono- or bicyclic saturated heterocyclyl group, $R^{x1}$ is hydrogen or $C_1$-$C_4$ alkyl.

In some embodiments, the compound has formula IIb:

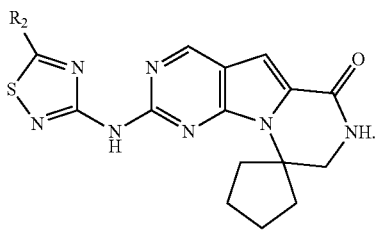

In some embodiments, the compound has formula Im and $R^2$ is

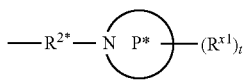

wherein P* is a 4- to 8-membered mono- or bicyclic saturated heterocyclyl group.

In some embodiments, the compound has formula Im and $R^2$ is

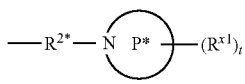

wherein P* is a 4- to 8-membered mono- or bicyclic saturated heterocyclyl group, $R^{x1}$ is hydrogen or $C_1$-$C_4$ alkyl.

DEFINITIONS

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) *Advanced Organic Chemistry* 5$^{th}$ Ed. Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in *March's Advanced Organic Chemistry: Reactions, Mechanisms, and Structure, 6$^{th}$ Edition*, M. B. Smith and J. March, John Wiley & Sons, Inc., Hoboken, N.J., 2007.

The term "alkyl," either alone or within other terms such as "haloalkyl" and "alkylamino," embraces linear or branched radicals having one to about twelve carbon atoms. "Lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylene" embraces bridging divalent linear and branched alkyl radicals. Examples include methylene, ethylene, propylene, isopropylene and the like.

The term "alkenyl" embraces linear or branched radicals having at least one carbon-carbon double bond of two to about twelve carbon atoms. "Lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl," embrace radicals having "cis" and "trans" orientations, or alternatively, "E" and "Z" orientations.

The term "alkynyl" denotes linear or branched radicals having at least one carbon-carbon triple bond and having two to about twelve carbon atoms. "Lower alkynyl" radicals having two to about six carbon atoms. Examples of such radicals include propargyl, butynyl, and the like.

Alkyl, alkenyl, and alkynyl radicals may be optionally substituted with one or more functional groups such as halo, hydroxy, nitro, amino, cyano, haloalkyl, aryl, heteroaryl, heterocyclo and the like.

The term "alkylamino" embraces "N-alkylamino" and "N,N-dialkylamino" where amino groups are independently substituted with one alkyl radical and with two alkyl radicals, respectively. "Lower alkylamino" radicals have one or two alkyl radicals of one to six carbon atoms attached to a nitrogen atom. Suitable alkylamino radicals may be mono or dialkylamino such as N-methylamino, N-ethylamino, N,N-dimethylamino, N,N-diethylamino and the like.

The term "halo" means halogens such as fluorine, chlorine, bromine or iodine atoms.

The term "haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means an alkyl radical having all hydrogen atoms replaced with fluoro atoms. Examples include trifluoromethyl and pentafluoroethyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. An aryl group may be optionally substituted with one or more functional groups such as halo, hydroxy, nitro, amino, cyano, haloalkyl, aryl, heteroaryl, heterocyclo and the like.

The term "heterocyclyl" (or "heterocyclo") embraces saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

Heterocyclo groups also includes radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5- oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroarylalkyl" denotes alkyl radicals substituted with a heteroaryl group. Examples include pyridylmethyl and thienylethyl.

The term "sulfonyl", whether used alone or linked to other terms such as alkylsulfonyl, denotes respectively divalent radicals —SO$_2$—.

The terms "carboxy" or "carboxyl", whether used alone or with other terms, such as "carboxyalkyl", denotes —C(O)—OH.

The term "carbonyl", whether used alone or with other terms, such as "aminocarbonyl", denotes —C(O)—.

The term "aminocarbonyl" denotes an amide group of the formula —C(O)—NH$_2$.

The terms "heterocycloalkyl" embrace heterocyclic-substituted alkyl radicals. Examples include piperidylmethyl and morpholinylethyl.

The term "arylalkyl" embraces aryl-substituted alkyl radicals. Examples include benzyl, diphenylmethyl and phenylethyl. The aryl in said aralkyl may be additionally substituted with halo, alkyl, alkoxy, halkoalkyl and haloalkoxy.

The term "cycloalkyl" includes saturated carbocyclic groups of 3 to 10 carbons. Lower cycloalkyl groups include $C_3$-$C_6$ rings. Examples include cyclopentyl, cyclopropyl, and cyclohexyl. Cycloalkyl groups may be optionally substituted with one or more functional groups such as halo, hydroxy, nitro, amino, cyano, haloalkyl, aryl, heteroaryl, heterocyclo and the like.

The term "cycloalkylalkyl" embraces cycloalkyl-substituted alkyl radicals. "Lower cycloalkylalkyl" radicals are cycloalkyl radicals attached to alkyl radicals having one to six carbon atoms. Examples of include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Examples include cyclopentenyl, cyclopentadienyl, cyclohexenyl and cycloheptadienyl.

The term "comprising" is meant to be open ended, including the indicated component but not excluding other elements.

The term "oxo" as used herein contemplates an oxygen atom attached with a double bond.

The term "nitro" as used herein contemplates —NO$_2$.

The term "cyano" as used herein contemplates —CN.

Synthesis

The disclosed compounds can be made by the following general schemes:

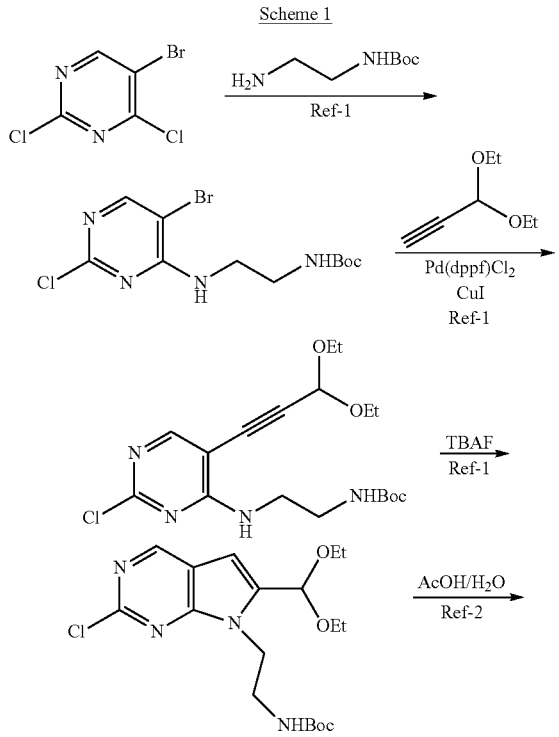

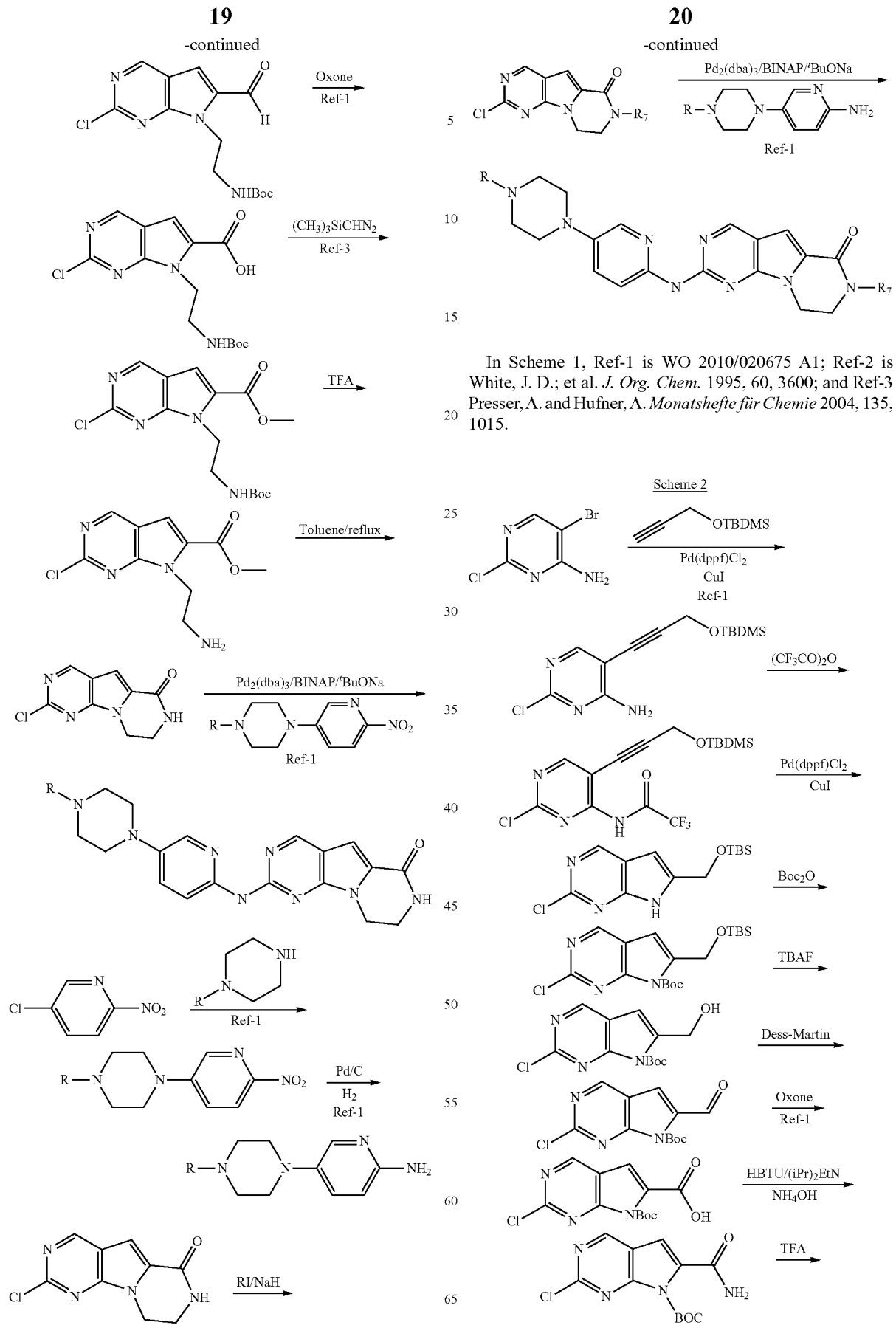
In Scheme 1, Ref-1 is WO 2010/020675 A1; Ref-2 is White, J. D.; et al. *J. Org. Chem.* 1995, 60, 3600; and Ref-3 Presser, A. and Hufner, A. *Monatshefte für Chemie* 2004, 135, 1015.

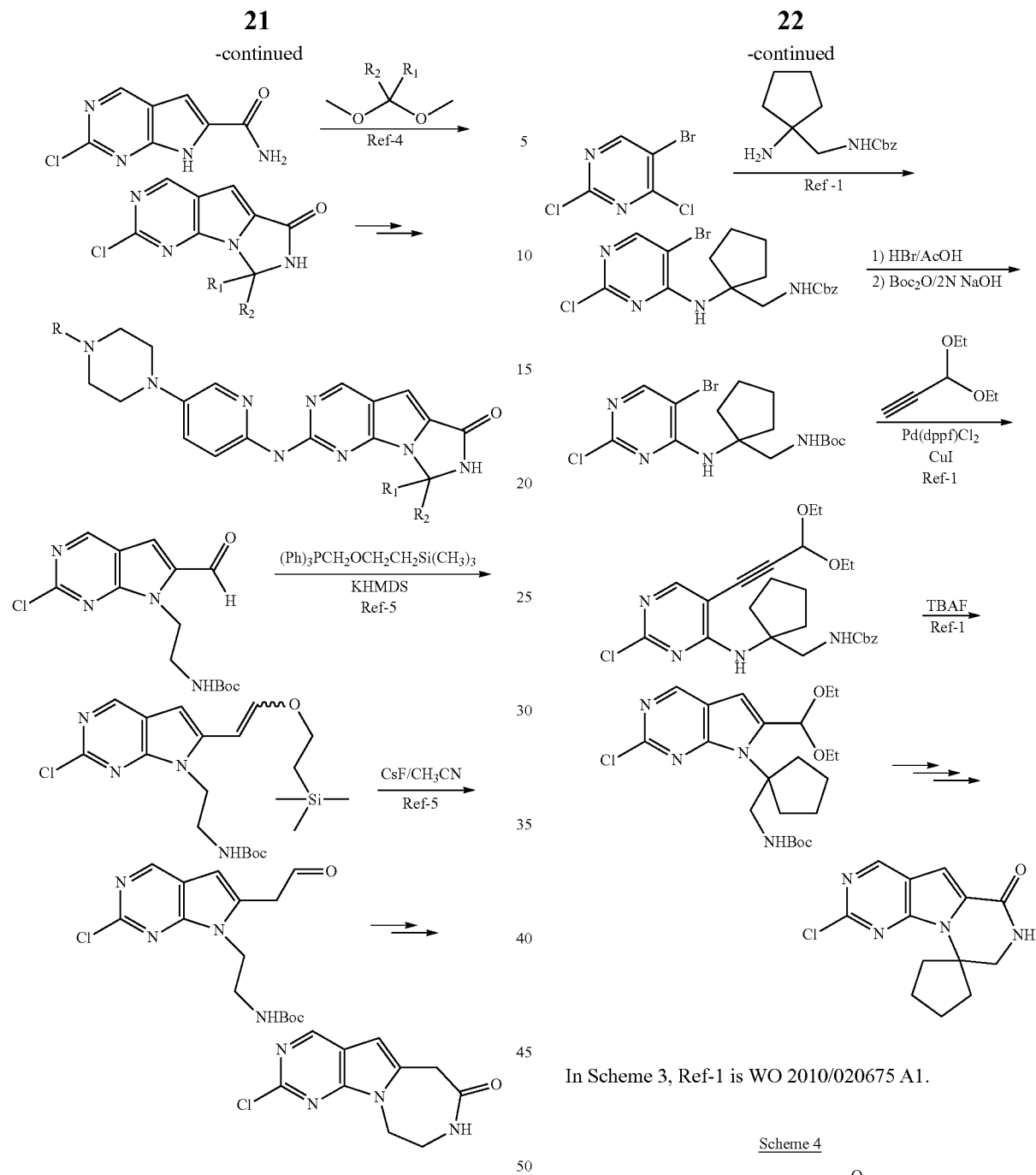
In Scheme 2, Ref-1 is WO 2010/020675 A1; Ref-4 is WO 2005/040166 A1; and Ref-5 is Schoenauer, K. and Zbiral, E. *Tetrahedron Letters* 1983, 24, 573.
In Scheme 3, Ref-1 is WO 2010/020675 A1.
Scheme 3
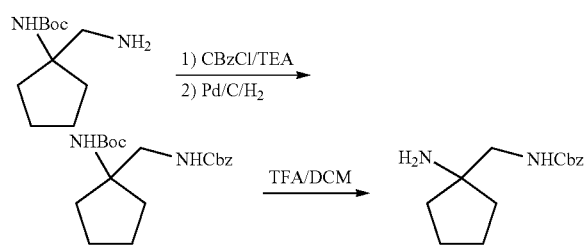
Scheme 4
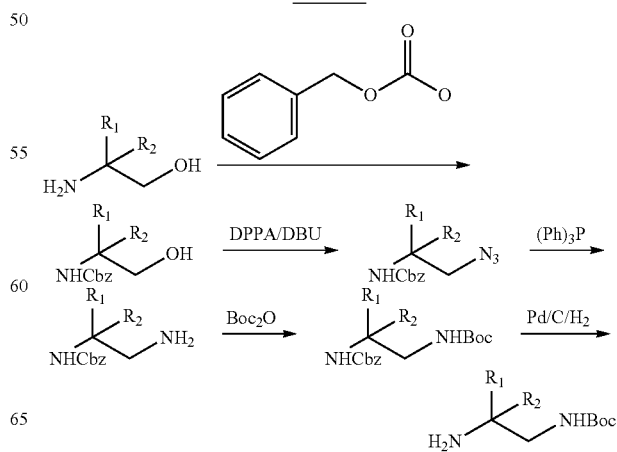

23

-continued

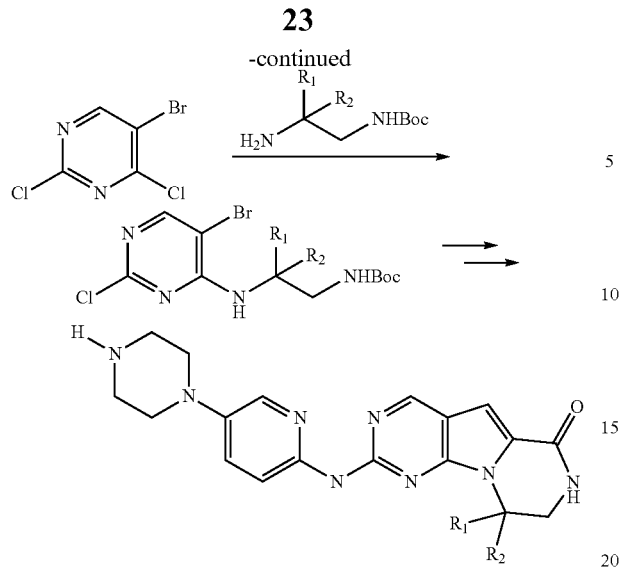

Scheme 5

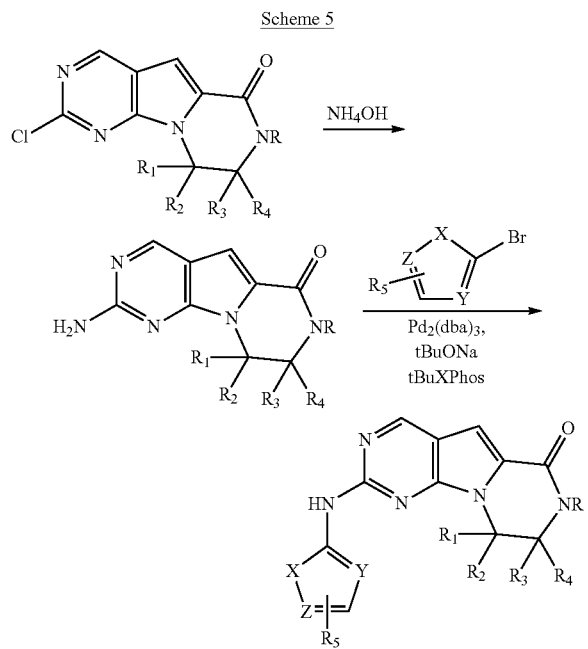

Scheme 5 illustrates a scheme useful for the synthesis of compounds of formula II.

EXAMPLES

Example 1 tert-butyl N-[2-[(5-bromo-2-chloro-pyrimidin-4-yl)amino]ethyl]carbamate

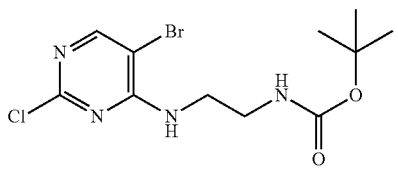 [SMILES: CC(C)(C)OC(=O)NCCNc1nc(Cl)ncc1Br]

24

To a solution of 5-bromo-2,4-dichloropyrimidine 3.2 g (0.0135 mole) in ethanol 80 mL was added Hunig's base 3.0 mL followed by the addition of a solution of N-(tert-butoxy carbonyl)-1,2-diaminoethane 2.5 g (0.0156 mole) in 20 mL ethanol. The contents were stirred overnight for 20 hrs. The solvent was evaporated under vacuum. Ethyl acetate (200 mL) and water (100 mL) was added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl] carbamate. $^1$HNMR (d6-DMSO) 8.21 (s, 1H), 7.62 (brs, 1H), 7.27 (brs, 1H), 3.39 (m, 2H), 3.12 (m, 2H), 1.34 (s, 9H). LCMS (ESI) 351 (M+H)

tert-butyl N-[2-[[2-chloro-5-(3,3-diethoxyprop-1-ynyl)pyrimidin-4-yl]amino]ethyl]carbamate To 3.6 mmole (1.265 g) of tert-butyl N-[2-[(5-bromo-2-chloro-pyrimidin-4-yl)amino]ethyl]carbamate in THF (10 mL) was added 0.778 mL of the acetal (5.43 mmol), 148 mg of Pd(dppf)CH$_2$Cl$_2$, triethylamine 0.757 mL (5.43 mmol. The contents were degassed and then purged with nitrogen. To this was then added 29 mg of CuI. The reaction mixture was heated under reflux for 48 hrs. After cooling, the contents were filtered over CELITE™ and concentrated. Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. $^1$HNMR (d6-DMSO) 8.18 (s, 1H), 7.63 (brs, 1H), 7.40 (brs, 1H), 5.55 (s, 1H), 3.70 (m, 2H), 3.60 (m, 2H), 3.42 (m, 2H), 3.15 (m, 2H), 1.19-1.16 (m, 15H). LCMS (ESI) 399 (M+H)

tert-butyl N-[2-[2-chloro-6-(diethoxymethyl)pyrrolo[2,3-d]pyrimidin-7-yl]ethyl]carbamate To a solution of the coupled product 2.1 g (0.00526 mole) in THF (30 mL) was added 7.0 g of TBAF solid. The contents were heated to 65 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). ¹HNMR (d6-DMSO) 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

tert-butyl N-[2-(2-chloro-6-formyl-pyrrolo[2,3-d]pyrimidin-7-yl)ethyl]carbamate

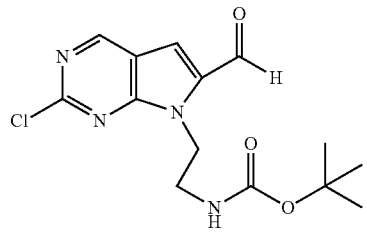 [SMILES: CC(C)(C)OC(=O)NCCn1c(C=O)cc2cnc(Cl)nc21]

To 900 mg of the acetal was added 8.0 mL AcOH and 1.0 mL water. This was stirred at room temperature for 16 hrs. Conc. and column ethyl acetate/hexanes (0-60%) afforded 0.510 g of tert-butyl N-[2-(2-chloro-6-formyl-pyrrolo[2,3-d]pyrimidin-7-yl)ethyl]carbamate as a foam. ¹HNMR (d6-DMSO) 9.98 (s, 1H), 9.18 (s, 1H), 7.66 (s, 1H), 6.80 (brs, 1H), 4.52 (m, 2H), 4.36 (m, 2H), 1.14 (s, 9H). LCMS (ESI) 325 (M+H)

7-[2-(tert-butoxycarbonylamino)ethyl]-2-chloro-pyrrolo[2,3-d]pyrimidine-6-carboxylic acid

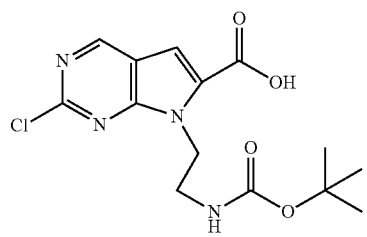 [SMILES: CC(C)(C)OC(=O)NCCn1c(C(=O)O)cc2cnc(Cl)nc21]

To the aldehyde 0.940 g in DMF (4 mL) was added oxone (1.95 g, 1.1 eq). The contents were stirred at room temp for 7 hrs. Column hexane/ethyl acetate (0-100%) afforded 0.545 g of 7-[2-(tert-butoxycarbonylamino)ethyl]-2-chloro-pyrrolo[2,3-d]pyrimidine-6-carboxylic acid. ¹HNMR (d6-DMSO) 9.11 (s, 1H), 7.39 (s, 1H), 4.38 (m, 2H), 4.15 (m, 2H), 1.48 (m, 9H). LCMS (ESI) 341(M+H)

methyl 7-[2-(tert-butoxycarbonylamino)ethyl]-2-chloro-pyrrolo[2,3-d]pyrimidine-6-carboxylate

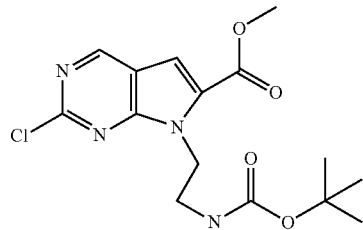

To a solution of 2-chloro-7-propyl-pyrrolo[2,3-d]pyrimidine-6-carboxylic acid 0.545 g (0.00156 mole) in toluene (3.5 mL) and MeOH (1 mL) was added TMS-diazomethane (1.2 mL). After stirring overnight at room temperature excess of TMS-diazomethane was quenched with acetic acid (3 mL) and then concentrated under vacuum. The residue was columned with hexane/ethyl acetate (0-70%) to afford methyl 7-[2-(tert-butoxycarbonylamino)ethyl]-2-chloro-pyrrolo[2,3-d]pyrimidine-6-carboxylate as a off white solid (0.52 g). ¹HNMR (d6-DMSO) 9.10 (s, 1H), 7.45 (s, 1H), 6.81 (brs, 1H) 4.60 (m, 2H), 3.91 (s, 3H), 3.29 (m, 2H), 1.18 (m, 9H) LCMS (ESI) 355 (M+H)

Chloro Tricyclic Amide

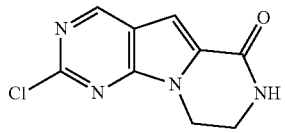 [SMILES: O=C1NCCn2c1cc1cnc(Cl)nc12]

To methyl 7-[2-(tert-butoxycarbonylamino)ethyl]-2-chloro-pyrrolo[2,3-d]pyrimidine-6-carboxylate 0.50 g (0.0014 mole) in dichloromethane (2.0 mL) was added TFA 0.830 mL. The contents were stirred at room temperature for 1 hr. Concentration under vacuum afforded the crude amino ester which was suspended in toluene (5 mL) and Hunig's base (0.5 mL). The contents were heated under reflux for 2 hrs. Concentration followed by column chromatography using hexane/ethyl acetate (0-50%) afforded the desired chloro tricyclic amide (0.260 g). ¹HNMR (d6-DMSO) 9.08 (s, 1H), 8.48 (brs, 1H), 7.21 (s, 1H) 4.33 (m, 2H), 3.64 (m, 2H). LCMS (ESI) 223 (M+H)

Chloro-N-methyltricyclic amide

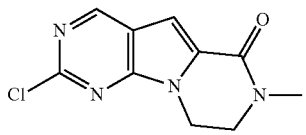 [SMILES: CN1CCn2c(cc3cnc(Cl)nc32)C1=O]

To a solution of the chloro tricycliclactam (185 mg, 0.00083 mole) in DMF (2.0 mL) was added sodium hydride (55% dispersion in oil, 52 mg). After stirring for 15 mins, methyl iodide (62 μL, 1.2 eq). The contents were stirred at room temperature for 30 mins. After the addition of methanol (5 mL), sat NaHCO₃ was added followed by the addition of ethyl acetate. Separation of the organic layer followed by drying with magnesium sulfate and concentration under vacuum afforded the N-methylated amide in quantitative yield. ¹HNMR (d6-DMSO) 9.05 (s, 1H), 7.17 (s, 1H), 4.38 (m, 2H), 3.80 (m, 2H), 3.05 (s, 3H). LCMS (ESI) 237 (M+H)

1-methyl-4-(6-nitro-3-pyridyl)piperazine

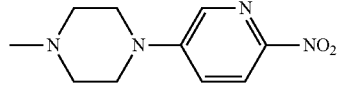

To 5-bromo-2-nitropyridine (4.93 g, 24.3 mmole) in DMF (20 mL) was added N-methylpiperazine (2.96 g, 1.1 eq) followed by the addition of DIPEA (4.65 mL, 26.7 mmole). The contents were heated at 90 degrees for 24 hrs. After addition of ethyl acetate (200 mL) water 100 mL was added and the layers separated. Drying followed by concentration afforded the crude product which was columned using (0-10%) DCM/Methanol. $^1$HNMR (δ6-DMSO) 8.26 (s, 1H), 8.15 (1H, d, J=9.3 Hz), 7.49 (1H, d, J=9.4 Hz), 3.50 (m, 4H), 2.49 (m, 4H), 2.22 (s, 3H).

5-(4-methylpiperazin-1-yl)pyridin-2-amine

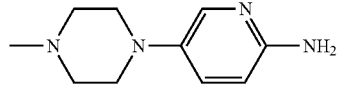

To 1-methyl-4-(6-nitro-3-pyridyl)piperazine 3.4 g in ethyl acetate (100 mL) and ethanol (100 mL) was added 10% Pd/c (400 mg) and then contents stirred under hydrogen (10 psi) overnight. After filtration through CELITE™, the solvents were evaporated and the crude product was purified over silica gel using DCM/7N Ammonia in MeOH (0-5%) to afford 5-(4-methylpiperazin-1-yl)pyridin-2-amine (2.2 g). $^1$HNMR (d6-DMSO) 7.56 (1H, d, J=3 Hz), 7.13 (1H, m), 6.36 (1H, d, J=8.8 Hz), 5.33 (brs, 2H), 2.88 (m, 4H), 2.47 (m, 4H), 2.16 (s, 3H).

tert-butyl 4-(6-amino-3-pyridyl)piperazine-1-carboxylate

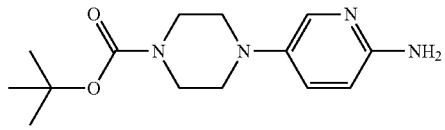 [SMILES: CC(C)(C)OC(=O)N1CCN(c2ccc(N)nc2)CC1]

This compound was prepared as described in WO 2010/020675 A1.

Example 2

Synthesis of Additional Intermediates

Scheme 4

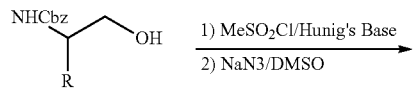

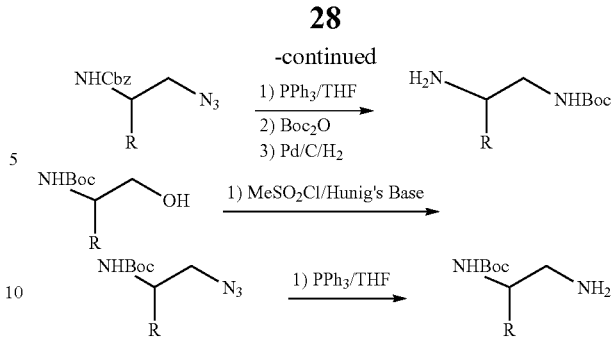

Intermediate A: tert-butyl N-[2-(benzyloxycarbonylamino)-3-methyl-butyl]carbamate

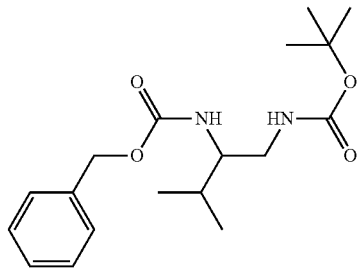 [SMILES: CC(C)C(CNC(=O)OC(C)(C)C)NC(=O)OCc1ccccc1]

To 11.0 g (0.0464 mole) of benzyl N-[1-(hydroxymethyl)-2-methyl-propyl]carbamate in dioxane (100 mL) cooled to 0° C. was added diphenylphosphoryl azide 10.99 mL (1.1 eq) followed by the addition of DBU 8.32 mL (1.2 eq). The contents were allowed to warm to room temperature and stirred for 16 hrs. After the addition of ethyl acetate (300 mL) and water (100 mL), the organic layer was separated and then washed with satd. NaHCO$_3$ (100 mL). The organic layer was then dried (magnesium sulfate) and then concentrated under vacuum. To this intermediate in DMSO (100 mL) was added sodium azide 7.54 g and the contents then heated to 90 degrees for 2 hrs. After addition of ethyl acetate and water the layers were separated. The organic layer was dried with magnesium sulfate followed by concentration under vacuum to afford an oil that was columned using hexane/ethyl acetate (0-70%) to afford benzyl N-[1-(azidomethyl)-2-methyl-propyl]carbamate 6.9 g as a colorless oil.

To benzyl N-[1-(azidomethyl)-2-methyl-propyl]carbamate 6.9 g (0.0263 mole) in THF (100 mL) was added triphenyl phosphine 7.59 g (1.1 eq). The contents were stirred for 20 hrs. After addition of water (10 mL), and stirring for an additional 6 hrs, ethyl acetate was added and the layers separated. After drying with magnesium sulfate and concentration under vacuum, the crude product was columned using DCM/MeOH (0-10%) to afford benzyl N-[1-(aminomethyl)-2-methyl-propyl]carbamate as a yellow oil.

To benzyl N-[1-(aminomethyl)-2-methyl-propyl]carbamate 4.65 g (0.019 mole) in THF (70 mL) was added 2N NaOH (20 mL) followed by the addition of di-tert-butyl dicarbonate 5.15 g (1.2 eq). After stirring for 16 hrs, ethyl acetate was added and the layers were separated. After drying with magnesium sulfate and concentration under vacuum, the crude product was purified using hexane/ethyl acetate (0-40%) over a silica gel column to afford intermediate A, tert-butyl N-[2-(benzyloxycarbonylamino)-3-methyl-butyl]carbamate, (6.1 g). 1H NMR (600 MHz, CHLOROFORM-d) δ ppm 0.89 (d, J=6.73 Hz, 3 H) 0.92 (d, J=6.73 Hz, 3 H) 1.38 (s, 9 H) 1.70-1.81 (m, 1 H) 3.18 (d, J=5.56 Hz, 2 H) 3.47-3.60 (m, 1 H) 4.76 (s, 1 H) 4.89 (d, J=7.90 Hz, 1 H) 5.07 (s, 2 H) 7.25-7.36 (m, 5 H). LCMS (ESI) 337 (M+H).

Intermediate B: tert-butyl N-[2-(benzyloxycarbonylamino)-4-methyl-pentyl]carbamate

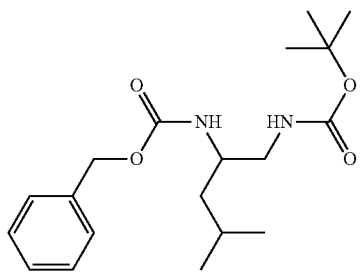

To a solution of benzyl N-[1-(hydroxymethyl)-3-methyl-butyl]carbamate 6.3 g (0.025 mole) in DCM (100 mL) was added diisopropylethyl amine 5.25 mL (1.2 eq) followed by the addition of methane sulfonylchloride 2.13 mL (1.1 eq) at 0 degrees. After stirring for 3 hrs, water (100 mL) was added and the organic layer separated. After drying with magnesium sulfate and concentration under vacuum, the crude [2-(benzyloxycarbonylamino)-4-methyl-pentyl]methanesulfonate which was taken directly to the next step.

To the crude [2-(benzyloxycarbonylamino)-4-methyl-pentyl]methanesulfonate from the above reaction in DMF (50 mL), was added sodium azide 2.43 g. The reaction mixture was then heated to 85 degrees for 3 hrs. After cooling, ethyl acetate (300 mL) and water was added. The organic layer was separated, dried with magnesium sulfate and then concentrated under vacuum to afford the crude benzyl N-[1-(azidomethyl)-3-methyl-butyl]carbamate. To this crude intermediate was added THF (100 mL) followed by triphenylphosphine 7.21 g and stirred under nitrogen for 16 hrs. After addition of water (10 mL), and stirring for an additional 6 hrs, ethyl acetate was added and the layers separated. After drying with magnesium sulfate and concentration under vacuum, the crude product was columned using DCM/MeOH (0-10%) to afford benzyl N-[1-(aminomethyl)-3-methyl-butyl]carbamate (4.5 g).

To benzyl N-[1-(aminomethyl)-3-methyl-butyl]carbamate 4.5 g (0.018 mole) in THF (60 mL) was added 2N NaOH (18 mL) followed by the addition of di-tert-butyl dicarbonate 4.19 g (1.07 eq). After stirring for 16 hrs, ethyl acetate was added and the layers separated. After drying with magnesium sulfate and concentration under vacuum, the crude product was taken to the next step. 1H NMR (600 MHz, CHLOROFORM-d) δ ppm 0.89 (d, J=6.73 Hz, 6 H) 1.25-1.34 (m, 1 H) 1.39 (s, 9 H) 1.57-1.71 (m, 2 H) 3.04-3.26 (m, 2 H) 3.68-3.80 (m, 1 H) 4.72-4.89 (m, 2 H) 5.06 (s, 2 H) 7.25-7.38 (m, 5H). LCMS (ESI) 351 (M+H).

Intermediate C: tert-butyl N-[(2R)-2-(benzyloxycarbonylamino)-3-methyl-butyl]carbamate

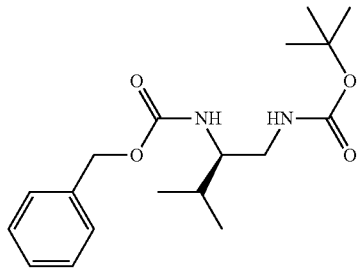 [SMILES: CC(C)[C@H](CNC(=O)OC(C)(C)C)NC(=O)OCc1ccccc1]

Intermediate C was synthesized from benzyl N-[(1R)-1-(hydroxymethyl)-2-methyl-propyl]carbamate using similar synthetic steps as that described for intermediate B. The analytical data (NMR and mass spec) was consistent with that for intermediate A.

Intermediate D: -tert-butyl N-[(2S)-2-(benzyloxycarbonylamino)-3-methyl-butyl]carbamate

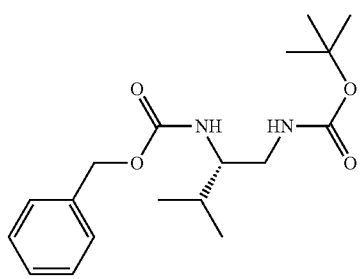 [SMILES: CC(C)[C@@H](CNC(=O)OC(C)(C)C)NC(=O)OCc1ccccc1]

Intermediate D was synthesized from benzyl N-[(1S)-1-(hydroxymethyl)-2-methyl-propyl]carbamate using similar synthetic steps as that described for intermediate B. The analytical data (NMR and mass spec) was consistent with that for intermediate A.

Intermediate E: tert-butyl N-[(1S)-1-(aminomethyl)-2-methyl-propyl]carbamate

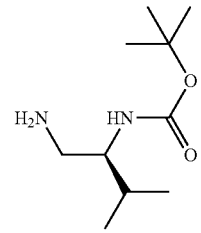

To a solution of tert-butyl N-[(1S)-1-(hydroxymethyl)-2-methyl-propyl]carbamate carbamate 6.3 g (0.025 mole) in THF (100 mL) was added diisopropylethyl amine 5.25 mL (1.2 eq) followed by the addition of methane sulfonylchloride 2.13 mL (1.1 eq) at 0 degrees. After stirring for 3 hrs, water (100 mL) was added and the organic layer separated. After drying with magnesium sulfate and concentration under vacuum, the crude [(2S)-2-(tert-butoxy carbonylamino)-3-methyl-butyl]methanesulfonate which was taken directly to the next step.

To the crude [(2S)-2-(tert-butoxycarbonylamino)-3-methyl-butyl]methanesulfonate from the above reaction in DMSO (50 mL), was added sodium azide 2.43 g. The reaction mixture was then heated to 85 degrees for 3 hrs. After cooling, ethyl acetate (300 mL) and water was added. The organic layer was separated, dried with magnesium sulfate and then concentrated under vacuum to afford the crude benzyl N-[1-(azidomethyl)-3-methyl-butyl]carbamate. To this crude intermediate was added THF (100 mL) followed by triphenylphosphine 7.21 g and stirred under nitrogen for 16 hrs. After addition of water (10 mL), and stirring for an additional 6 hrs, ethyl acetate was added and the layers separated. After drying with magnesium sulfate and concentration under vacuum, the crude product was columned using DCM/MeOH (0-10%) to afford benzyl N-[1-(aminomethyl)-3-methyl-butyl]carbamate (4.5 g). LCMS (ESI) 203 (M+H).

Intermediate F: tert-butyl N-[(1R)-1-(aminomethyl)-2-methyl-propyl]carbamate

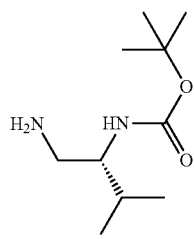

Intermediate F was synthesized from tert-butyl N-[(1R)-1-(hydroxymethyl)-2-methyl-propyl]carbamate using a similar synthetic sequence as described for intermediate E. The analytical data (NMR and mass spec) was consistent with intermediate E.

Intermediate G: tert-butyl N-[(2S)-2-(benzyloxycarbonylamino)-4-methyl-pentyl]carbamate

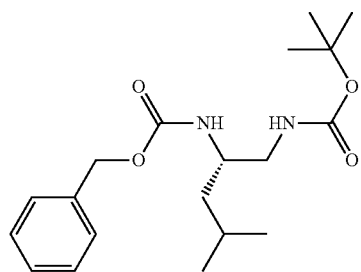 [SMILES: CC(C)C[C@@H](CNC(=O)OC(C)(C)C)NC(=O)OCc1ccccc1]

Intermediate G was synthesized from benzyl N-[(1S)-1-(hydroxymethyl)-3-methyl-butyl]carbamate using a similar synthetic sequence as described for intermediate B. The analytical data (NMR and mass spec) was consistent with intermediate B.

Intermediate H: tert-butyl N-[(2S)-2-(benzyloxycarbonylamino)-2-phenyl-ethyl]carbamate

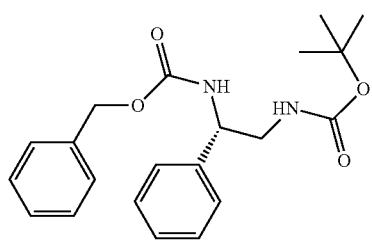 [SMILES: CC(C)(C)OC(=O)NC[C@@H](NC(=O)OCc1ccccc1)c1ccccc1]

Intermediate H was synthesized from benzyl N-[(1S)-2-hydroxy-1-phenyl-ethyl]carbamate using a similar synthetic sequence as described for intermediate B. 1H NMR (600 MHz, DMSO-$d_6$) δ ppm 1.20-1.33 (m, 9 H) 3.11 (t, J=6.29 Hz, 2 H) 4.59-4.68 (m, 1 H) 4.88-5.01 (m, 2 H) 6.81 (t, J=5.42 Hz, 1 H) 7.14-7.35 (m, 10 H) 7.69 (d, J=8.49 Hz, 1 H). LCMS (ESI) 371 (M+H).

Intermediate I: tert-butyl N-[(2S)-2-(benzyloxycarbonylamino)-3-methyl-pentyl]carbamate

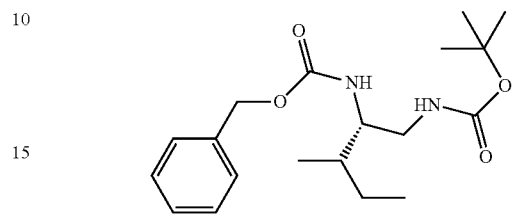

Intermediate I was synthesized from benzyl N-[(1S)-1-(hydroxymethyl)-2-methyl-butyl]carbamate using a similar synthetic sequence as described for intermediate B. 1H NMR (600 MHz, CHLOROFORM-d) δ ppm 0.85-0.92 (m, 6 H) 1.05-1.15 (m, 1 H) 1.35-1.41 (m, 9 H) 1.45-1.56 (m, 2 H) 3.14-3.24 (m, 2 H) 3.54-3.64 (m, 1 H) 4.78 (s, 1 H) 4.96 (d, J=7.91 Hz, 1 H) 5.06 (s, 2 H) 7.27-7.37 (m, 5 H). LCMS (ESI) 351 (M+H).

Intermediate J: tert-butyl N-[(2S)-2-(benzyloxycarbonylamino)-3,3-dimethyl-butyl]carbamate

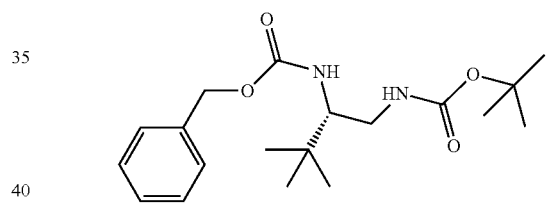

Intermediate J was synthesized from benzyl N-[(1S)-1-(hydroxymethyl)-2,2-dimethyl-propyl]carbamate using a similar synthetic sequence as described for intermediate B. LCMS (ESI) 351.

Intermediate K: tert-butyl N-[[1-(benzyloxycarbonylamino)cyclohexyl]methyl]carbamate

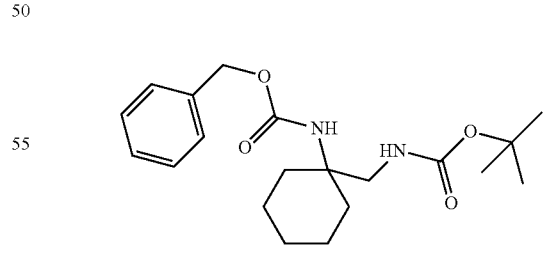

To a solution of benzyl N-[1-(aminomethyl)cyclohexyl]carbamate 10.0 g (0.0381 mole) in THF (150 mL) was added di-tert-butyl dicarbonate (9.15 g, 1.1 eq) and the contents stirred at room temperature for 16 hrs. Ethyl acetate and water was then added. The organic layer was separated, dried over magnesium sulfate and then concentrated under vacuum to afford tert-butyl N-[[1-(benzyloxycarbonylamino)cyclohexyl]methyl]carbamate (13.1 g). 1H NMR (600 MHz, DMSO-d$_6$) δ ppm 0.92-1.54 (m, 17 H) 1.76-2.06 (m, 2 H) 3.09 (d, J=6.15 Hz, 2 H) 4.92 (s, 2 H) 6.63 (d, J=17.27 Hz, 1 H) 7.16-7.49 (m, 6 H). LCMS (ESI) 363 (M+H).

Intermediate L: tert-butyl N-[[1-(benzyloxycarbonylamino)cyclopentyl]methyl]carbamate

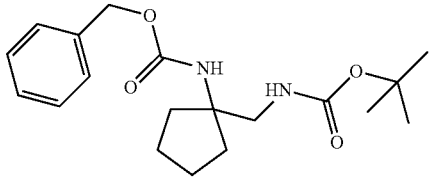 [SMILES: CC(C)(C)OC(=O)NCC1(NC(=O)OCc2ccccc2)CCCC1]

tert-butyl N-[[1-(benzyloxycarbonylamino)cyclopentyl]methyl]carbamate was synthesized in an analogous manner to tert-butyl N-[[1-(benzyloxycarbonylamino)cyclohexyl]methyl]carbamate. LCMS (ESI) 349 (M+H).

Example 3

Synthesis of Substituted 2-aminopyridines

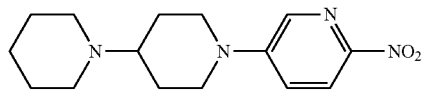 [SMILES: O=[N+]([O-])c1ccc(N2CCC(N3CCCCC3)CC2)cn1]

To 5-bromo-2-nitropyridine (1.2 g, 5.9 mmol) in DMSO (4 mL) was added 1-(4-piperidyl)piperidine (1.0 g, 5.9 mmole) and triethyl amine (0.99 mL, 7.1 mmole). The contents were heated to 120 degrees in a CEM Discovery microwave system for 3 hours. The crude reaction was then loaded over a silica gel column and eluted with DCM/methanol (0-20%) to afford 2-nitro-5-[4-(1-piperidyl)-1-piperidyl]pyridine as an oil (457 mg). 1H NMR (600 MHz, DMSO-d$_6$) δ ppm 1.26-1.36 (m, 2 H) 1.43 (m, 6 H) 1.76 (m, 2 H) 2.37 (m, 5 H) 2.94 (t, J=12.74 Hz, 2 H) 4.06 (d, J=13.47 Hz, 2 H) 7.41 (dd, J=9.37, 2.64 Hz, 1 H) 8.08 (d, J=9.37 Hz, 1 H) 8.20 (d, J=2.64 Hz, 1 H).

5-[4-(1-piperidyl)-1-piperidyl]pyridin-2-amine

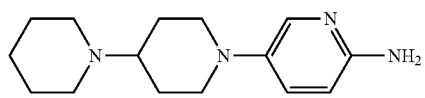

5-[4-(1-piperidyl)-1-piperidyl]pyridin-2-amine was prepared in a manner similar to that used in the synthesis of 5-(4-methylpiperazin-1-yl)pyridin-2--amine. 1H NMR (600 MHz, DMSO-d$_6$) δ ppm 1.13-1.37 (m, 6 H) 1.40-1.63 (m, 6 H) 1.71 (m, 2 H), 2.24 (m, 1 H) 2.43 (m, 2 H) 3.33 (d, J=12.30 Hz, 2 H) 5.31 (s, 2 H) 6.33 (d, J=8.78 Hz, 1 H) 7.10 (dd, J=8.78, 2.93 Hz, 1 H) 7.55 (d, J=2.64 Hz, 1 H). LCMS (ESI) 261 (M+H).

4-[1-(6-nitro-3-pyridyl)-4-piperidyl]morpholine

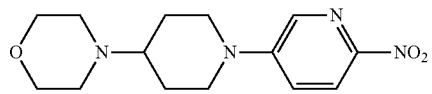

4-[1-(6-nitro-3-pyridyl)-4-piperidyl]morpholine was synthesized in a manner similar to that used in the synthesis of 2-nitro-5-[4-(1-piperidyl)-1-piperidyl]pyridine. 1H NMR (600 MHz, DMSO-d$_6$) δ ppm 1.41 (m, 2 H) 1.82 (m, 2 H) 2.42 (m, 5 H) 2.98 (t, J=12.44 Hz, 2 H) 3.52 (s, 4 H) 4.04 (d, J=12.88 Hz, 2 H) 7.42 (d, J=9.37 Hz, 1 H) 8.08 (d, J=9.08 Hz, 1 H) 8.21 (s, 1 H).

5-(4-morpholino-1-piperidyl) pyridin-2-amine

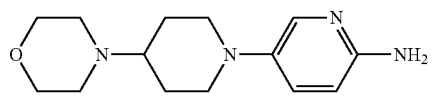

5-(4-morpholino-1-piperidyl)pyridin-2-amine was prepared in a manner similar to that used in the synthesis of 5-(4-methylpiperazin-1-yl)pyridin-2-amine. 1H NMR (600 MHz, DMSO-d$_6$) δ ppm 1.34-1.52 (m, 2 H) 1.78 (m, 2 H) 2.14 (m, 1 H) 2.43 (m, 4 H) 3.32 (d, J=12.30 Hz, 4 H) 3.47-3.59 (m, 4 H) 5.32 (s, 2 H) 6.34 (d, J=8.78 Hz, 1 H) 7.11 (dd, J=8.93, 2.78 Hz, 1 H) 7.47-7.62 (m, 1 H). LCMS (ESI) 263 (M+H).

4-[1-(6-nitro-3-pyridyl)-4-piperidyl]thiomorpholine

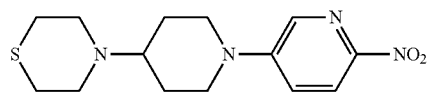

4-[1-(6-nitro-3-pyridyl)-4-piperidyl]thiomorpholine was synthesized in a manner similar to that used in the synthesis of 2-nitro-5-[4-(1-piperidyl)-1-piperidyl]pyridine. 1H NMR (600 MHz, DMSO-d$_6$) δ ppm 1.40-1.52 (m, 2 H) 1.71 (m, 2 H) 2.49-2.55 (m, 4 H) 2.56-2.63 (m, 1 H) 2.68-2.75 (m, 4 H) 2.88-2.98 (m, 2 H) 4.09 (d, J=13.18 Hz, 2 H) 7.42 (dd, J=9.22, 3.07 Hz, 1 H) 8.08 (d, J=9.37 Hz, 1 H) 8.20 (d, J=3.22 Hz, 1 H).

5-(4-thiomorpholino-1-piperidyl)pyridin-2-amine

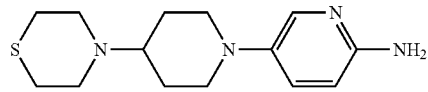 [SMILES: Nc1ccc(N2CCC(N3CCSCC3)CC2)cn1]

5-(4-thiomorpholino-1-piperidyl)pyridin-2-amine was prepared in a manner similar to that used in the synthesis of 5-(4-methylpiperazin-1-yl)pyridin-2--amine. 1H NMR (600

MHz, DMSO-d$_6$) δ ppm 1.47-1.59 (m, 2 H) 1.65 (m, 2 H) 2.22-2.38 (m, 1 H) 2.50-2.59 (m, 6 H) 2.68-2.82 (m, 4 H) 3.33 (d, J=12.00 Hz, 2 H) 5.31 (s, 2 H) 6.33 (d, J=9.08 Hz, 1 H) 7.10 (dd, J=8.78, 2.93 Hz, 1 H) 7.55 (d, J=2.64 Hz, 1 H). LCMS (ESI) 279 (M+H).

2-nitro-5-(1-piperidyl)pyridine

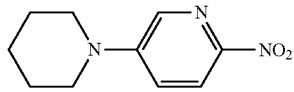 [SMILES: O=[N+]([O-])c1ccc(N2CCCCC2)cn1]

2-nitro-5-(1-piperidyl)pyridine was synthesized in a manner similar to that used in the synthesis of 2-nitro-5-[4-(1-piperidyl)-1-piperidyl]pyridine. 1H NMR (600 MHz, DMSO-d$_6$) δ ppm 1.56 (m, 6 H) 3.49 (d, J=4.39 Hz, 4 H) 7.30-7.47 (m, 1 H) 8.02-8.12 (m, 1 H) 8.15-8.26 (m, 1 H).

5-(1-piperidyl)pyridin-2-amine

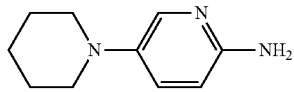

5-(1-piperidyl)pyridin-2-amine was prepared in a manner similar to that used in the synthesis of 5-(4-methylpiperazin-1-yl)pyridin-2--amine. 1H NMR (600 MHz, DMSO-d$_6$) δ ppm 1.39-1.46 (m, 2 H) 1.51-1.62 (m, 4 H) 2.75-2.92 (m, 4 H) 5.30 (s, 2 H) 6.34 (d, J=8.78 Hz, 1 H) 7.09 (dd, J=8.78, 2.93 Hz, 1 H) 7.54 (d, J=2.93 Hz, 1 H). LCMS (ESI) 178 (M+H).

4-(6-nitro-3-pyridyl)thiomorpholine

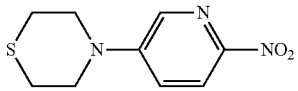

4-(6-nitro-3-pyridyl)thiomorpholine was synthesized in a manner similar to that used in the synthesis of 2-nitro-5-[4-(1-piperidyl)-1-piperidyl]pyridine. 1H NMR (600 MHz, DMSO-d$_6$) δ ppm 2.56-2.69 (m, 4 H) 3.79-3.92 (m, 4 H) 7.43 (dd, J=9.22, 3.07 Hz, 1 H) 8.10 (d, J=9.37 Hz, 1 H) 8.20 (d, J=2.93 Hz, 1 H).

5-thiomorpholinopyridin-2-amine

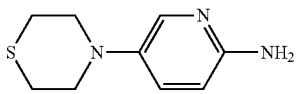 [SMILES: Nc1ccc(N2CCSCC2)cn1]

5-thiomorpholinopyridin-2-amine was prepared in a manner similar to that used in the synthesis of 5-(4-methylpiperazin-1-yl)pyridin-2--amine. 1H NMR (600 MHz, DMSO-d$_6$) δ ppm 2.59-2.73 (m, 4 H) 3.04-3.20 (m, 4 H) 5.41 (s, 2 H) 6.35 (d, J=8.78 Hz, 1 H) 7.10 (dd, J=8.78, 2.93 Hz, 1 H) 7.57 (d, J=2.64 Hz, 1 H). LCMS (ESI) 196 (M+H).

tert-butyl (4R)-5-(6-nitro-3-pyridyl)-2,5-diazabicyclo[2.2.1]heptane-2-carboxylate

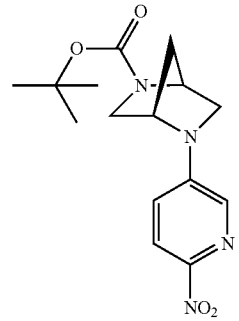

tert-butyl (4R)-5-(6-nitro-3-pyridyl)-2,5-diazabicyclo[2.2.1]heptane-2-carboxylate was synthesized in a manner similar to that used in the synthesis of 2-nitro-5-[4-(1-piperidyl)-1-piperidyl]pyridine. 1H NMR (600 MHz, DMSO-d$_6$) δ ppm 1.33 (d, J=32.21 Hz, 11 H) 1.91 (m, 2 H) 3.15 (d, J=10.25 Hz, 1 H) 3.58 (m, 1 H) 4.46 (m, 1 H) 4.83 (s, 1 H) 7.16 (s, 1 H) 7.94 (s, 1 H) 8.05-8.16 (m, 1 H).

tert-butyl (4R)-5-(6-amino-3-pyridyl)-2,5-diazabicyclo[2.2.1]heptane-2-carboxylate

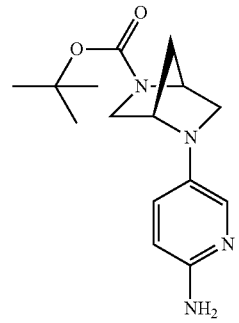 [SMILES: CC(C)(C)OC(=O)N1C[C@H]2CC1CN2c1ccc([N+](=O)[O-])nc1]

tert-butyl (4R)-5-(6-amino-3-pyridyl)-2,5-diazabicyclo[2.2.1]heptane-2-carboxylate was prepared in a manner similar to that used in the synthesis of 5-(4-methylpiperazin-1-yl)pyridin-2--amine. 1H NMR (600 MHz, DMSO-d$_6$) δ ppm 1.31 (d, J=31.91 Hz, 11 H) 1.83 (m, 2 H) 2.71-2.82 (m, 1 H) 3.44 (m, 1 H) 4.30 (d, 2H) 5.08 (s, 2 H) 6.35 (d, J=8.78 Hz, 1 H) 6.77-6.91 (m, 1 H) 7.33 (s, 1 H). LCMS (ESI) 291 (M+H).

N,N-dimethyl-1-(6-nitro-3-pyridyl)piperidin-4-amine

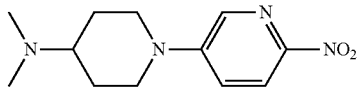 [SMILES: CN(C)C1CCN(c2ccc([N+](=O)[O-])nc2)CC1]

N,N-dimethyl-1-(6-nitro-3-pyridyl)piperidin-4-amine was synthesized in a manner similar to that used in the synthesis of 2-nitro-5-[4-(1-piperidyl)-1-piperidyl]pyridine. 1H NMR (600 MHz, DMSO-d$_6$) δ ppm 1.30-1.45 (m, 2 H) 1.79 (m, 2 H) 2.14 (s, 6 H) 2.33 (m, 1 H) 2.92-3.04 (m, 2 H) 4.03 (d, J=13.76 Hz, 2 H) 7.42 (dd, J=9.22, 3.07 Hz, 1 H) 8.04-8.11 (m, 1 H) 8.21 (d, J=2.93 Hz, 1 H).

5-[4-(dimethylamino)-1-piperidyl]pyridin-2-amine

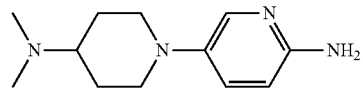

5-[4-(dimethylamino)-1-piperidyl]pyridin-2-amine was prepared in a manner similar to that used in the synthesis of 5-(4-methylpiperazin-1-yl)pyridin-2--amine. 1H NMR (600 MHz, DMSO-d$_6$) δ ppm 1.35-1.50 (m, 2 H) 1.69-1.81 (m, 2 H) 2.00-2.10 (m, 1 H) 2.11-2.22 (s, 6 H) 3.17-3.36 (m, 4 H) 5.19-5.38 (s, 2 H) 6.34 (d, J=8.78 Hz, 1 H) 7.10 (dd, J=8.78, 2.93 Hz, 1 H) 7.55 (d, J=2.63 Hz, 1 H). LCMS (ESI) 221 (M+H).

4-(6-nitro-3-pyridyl)morpholine

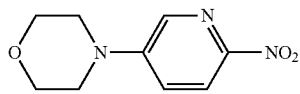 [SMILES: O=[N+]([O-])c1ccc(N2CCOCC2)cn1]

4-(6-nitro-3-pyridyl)morpholine was synthesized in a manner similar to that used in the synthesis of 2-nitro-5-[4-(1-piperidyl)-1-piperidyl]pyridine.

5-morpholinopyridin-2-amine

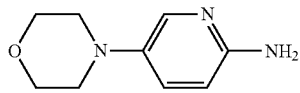

5-morpholinopyridin-2-amine was prepared in a manner similar to that used in the synthesis of 5-(4-methylpiperazin-1-yl)pyridin-2--amine. 1H NMR (600 MHz, CHLOROFORM-d) δ ppm 2.91-3.00 (m, 4 H) 3.76-3.84 (m, 4 H) 4.19 (br. s., 2 H) 6.45 (d, J=8.78 Hz, 1 H) 7.12 (dd, J=8.78, 2.93 Hz, 1 H) 7.72 (d, J=2.93 Hz, 1 H).

5-(4-isobutylpiperazin-1-yl)pyridin-2-amine

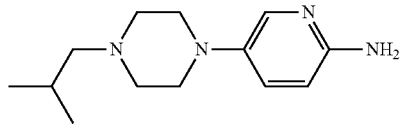

1-isobutyl-4-(6-nitro-3-pyridyl)piperazine was synthesized in a manner similar to that used in the synthesis of 2-nitro-5-[4-(1-piperidyl)-1-piperidyl]pyridine which was then converted 5-(4-isobutylpiperazin-1-yl)pyridin-2-amine in a manner similar to that used in the synthesis of 5-(4-methylpiperazin-1-yl)pyridin-2--amine. 1H NMR (600 MHz, CHLOROFORM-d) δ ppm 0.88 (d, J=6.73 Hz, 6 H) 1.71-1.84 (m, 1 H) 2.10 (d, J=7.32 Hz, 2 H) 2.46-2.58 (m, 4 H) 2.97-3.07 (m, 4 H) 4.12 (s, 2 H) 6.45 (d, J=8.78 Hz, 1 H) 7.14 (dd, J=8.78, 2.93 Hz, 1 H) 7.75 (d, J=2.93 Hz, 1 H). LCMS (ESI) 235 (M+H).

5-(4-isopropylpiperazin-1-yl)pyridin-2-amine

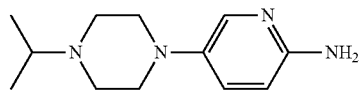 [SMILES: CC(C)N1CCN(c2ccc(N)nc2)CC1]

1-isopropyl-4-(6-nitro-3-pyridyl)piperazine was synthesized in a manner similar to that used in the synthesis of 2-nitro-5-[4-(1-piperidyl)-1-piperidyl]pyridine which was then converted to 5-(4-isopropylpiperazin-1-yl)pyridin-2-amine in a manner similar to that used in the synthesis of 5-(4-methylpiperazin-1-yl)pyridin-2-amine. 1H NMR (600 MHz, CHLOROFORM-d) δ ppm 1.06 (d, J=6.44 Hz, 6 H) 2.59-2.75 (m, 5 H) 2.97-3.10 (m, 4 H) 4.13 (s, 2 H) 6.45 (d, J=8.78 Hz, 1 H) 7.15 (dd, J=9.08, 2.93 Hz, 1 H) 7.76 (d, J=2.93 Hz, 1 H). LCMS (ESI) 221 (M+H).

5-[(2R,6S)-2,6-dimethylmorpholin-4-yl]pyridin-2-amine

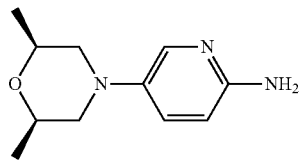

(2S,6R)-2,6-dimethyl-4-(6-nitro-3-pyridyl)morpholine was synthesized in a manner similar to that used in the synthesis of 2-nitro-5-[4-(1-piperidyl)-1-piperidyl]pyridine which was then converted to 5-[(2R,6S)-2,6-dimethylmorpholin-4-yl]pyridin-2-amine in a manner similar to that used in the synthesis of 5-(4-methylpiperazin-1-yl)pyridin-2-amine. 1H NMR (600 MHz, CHLOROFORM-d) δ ppm 1.20 (d, J=6.44 Hz, 6 H) 2.27-2.39 (m, 2 H) 3.11-3.21 (m, 2 H) 3.70-3.84 (m, 2 H) 4.15 (s, 2 H) 6.45 (d, J=8.78 Hz, 1 H) 7.12 (dd, J=8.78, 2.93 Hz, 1 H) 7.72 (d, J=2.63 Hz, 1 H). LCMS (ESI) 208 (M+H).

5-[(3R,5S)-3,5-dimethylpiperazin-1-yl]pyridin-2-amine

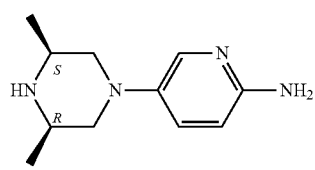

(3S,5R)-3,5-dimethyl-1-(6-nitro-3-pyridyl)piperazine was synthesized in a manner similar to that used in the synthesis of 2-nitro-5-[4-(1-piperidyl)-1-piperidyl]pyridine which was then converted to 5-[(3R,5S)-3,5-dimethylpiperazin-1-yl]pyridin-2-amine in a manner similar to that used in the synthesis of 5-(4-methylpiperazin-1-yl)pyridin-2-amine. 1H NMR (600 MHz, CHLOROFORM-d) δ ppm 1.09 (d, J=6.44 Hz, 6 H) 2.20 (t, J=10.83 Hz, 2 H) 2.95-3.08 (m, 2 H) 3.23 (dd, J=11.71, 2.05 Hz, 2 H) 4.13 (s, 2 H) 6.45 (d, J=8.78 Hz, 1 H) 7.14 (dd, J=8.78, 2.93 Hz, 1 H) 7.73 (d, J=2.63 Hz, 1 H). LCMS (ESI) 207 (M+H).

Intermediate 1A

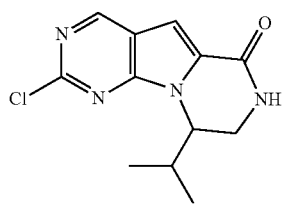 [SMILES: CC(C)C1CNC(=O)c2cc3cnc(Cl)nc3n21]

tert-butyl N-[2-[(5-bromo-2-chloro-pyrimidin-4-yl)amino]-3-methyl-butyl]carbamate

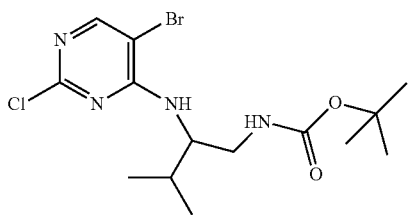 [SMILES: CC(C)C(CNC(=O)OC(C)(C)C)Nc1nc(Cl)ncc1Br]

A solution of intermediate A in ethanol (100 mL) was hydrogenated under 30 psi of hydrogen using 10% Pd/C (0.7 g) in a pressure bomb for 7 hrs. After filtration of the reaction mixture through CELITE™, the organic layer was concentrated under vacuum to afford tert-butyl N-(2-amino-3-methyl-butyl)carbamate (3.8 g).

To a solution of 5-bromo-2,4-dichloro-pyrimidine 7.11 g (0.0312 mole) in ethanol (100 mL) was added diisopropylethyl amine 5.45 mL (1.0 eq) and tert-butyl N-(2-amino-3-methyl-butyl) carbamate 6.31 g (0.0312 mole). The reaction mixture was stirred at room temperature for 20 hrs. After concentration under vacuum, ethyl acetate and water was added. The organic layer was separated, dried with magnesium sulfate and then concentrated under vacuum. The crude product was purified by column chromatography using hexane/ethyl acetate (0-30%) over silica gel to afford tert-butyl N-[2-[(5-bromo-2-chloro-pyrimidin-4-yl)amino]-3-methyl-butyl]carbamate. 1H NMR (600 MHz, DMSO-d$_6$) δ ppm 0.77-0.85 (d, J=6.5 Hz, 3 H) 0.87 (d, J=6.73 Hz, 3 H) 1.31-1.39 (m, 9 H) 1.82-1.93 (m, 1 H) 2.94 (d, J=5.56 Hz, 1 H) 3.08-3.22 (m, 2 H) 3.98 (d, J=8.20 Hz, 1 H) 6.96 (d, J=8.78 Hz, 1 H) 8.21 (s, 1 H). LCMS (ESI) 393 (M+H).

tert-butyl N-[2-[2-chloro-6-(diethoxymethyl)pyrrolo[2,3-d]pyrimidin-7-yl]-3-methyl-butyl]carbamate

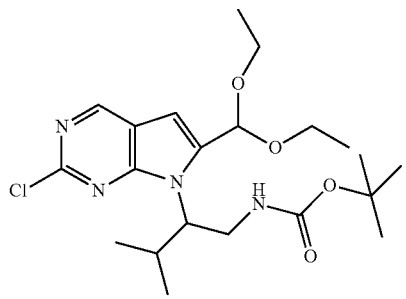 [SMILES: CCOC(OCC)c1cc2cnc(Cl)nc2n1C(CNC(=O)OC(C)(C)C)C(C)C]

tert-butyl N-[2-[2-chloro-6-(diethoxymethyl)pyrrolo[2,3-d]pyrimidin-7-yl]-3-methyl-butyl]carbamate was synthesized by subjecting tert-butyl N-[2-[(5-bromo-2-chloro-pyrimidin-4-yl)amino]-3-methyl-butyl]carbamate to Sonogoshira conditions as described for tert-butyl N-[2-[[2-chloro-5-(3,3-diethoxyprop-1-ynyl)pyrimidin-4-yl]amino]ethyl]carbamate followed by subsequent treatment with TBAF as described in the synthesis of tert-butyl N-[2-[2-chloro-6-(diethoxymethyl)pyrrolo[2,3-d]pyrimidin-7-yl]ethyl]carbamate. 1H NMR (600 MHz, DMSO-d$_6$) δ ppm 1.11 (d, J=6.44 Hz, 3 H) 1.18 (t, J=7.03 Hz, 6 H) 1.21-1.26 (m, 12 H) 2.88 (br. s., 1 H) 3.43-3.78 (m, 6 H) 3.97-4.08 (m, 1 H) 5.61 (s, 1 H) 6.65 (s, 1 H) 6.71-6.78 (m, 1 H) 8.87 (s, 1 H). LCMS (ESI) 441 (M+H).

7-[1-[(tert-butoxycarbonylamino)methyl]-2-methyl-propyl]-2-chloro-pyrrolo[2,3-d]pyrimidine-6-carboxylic acid

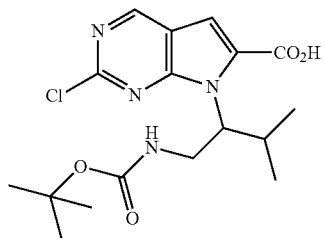 [SMILES: CC(C)C(CNC(=O)OC(C)(C)C)n1c(C(=O)O)cc2cnc(Cl)nc21]

To a solution tert-butyl N-[2-[[2-chloro-5-(3,3-diethoxyprop-1-ynyl)pyrimidin-4-yl]amino]ethyl]carbamate in THF was added TBAF and the contents refluxed for 3 hrs. Ethyl acetate and water was then added and the organic layer separated, dried with magnesium sulfate and then concentrated under vacuum. To this crude reaction was added acetic acid/water (9:1) and then contents stirred for 12 hrs at room temperature. After concentration under vacuum, sat NaHCO$_3$ and ethyl acetate was then added. The organic layer was separated, dried and then concentrated under vacuum. The crude reaction product thus obtained was dissolved in DMF, oxone was then added and the contents stirred for 3 hrs. After addition of ethyl acetate, the reaction mixture was filtered through CELITE™ and concentrated under vacuum. Column chromatography of the crude product over silica gel using hexane/ethyl acetate (0-100%) afforded 7-[1-[(tert-butoxy-carbonylamino)methyl]-2-methyl-propyl]-2-chloro-pyrrolo [2,3-d]pyrimidine-6-carboxylic acid. 1H NMR (600 MHz, DMSO-d$_6$) δ ppm 0.85 (d, J=7.03 Hz, 3 H) 0.97 (d, J=6.73 Hz, 3 H) 1.52 (s, 9 H) 1.99-2.23 (m, 1 H) 3.98 (dd, J=14.05, 3.51 Hz, 1 H) 4.47-4.71 (m, 2 H) 7.47 (s, 1 H) 9.17 (s, 1 H). LCMS (ESI) 383 (M+H).

Intermediate 1A

To 7-[1-[(tert-butoxycarbonylamino)methyl]-2-methyl-propyl]-2-chloro-pyrrolo[2,3-d]pyrimidine-6-carboxylic acid 0.050 g (0.00013 mole) in DCM (1.5 mL) was added DIC (32.7 mg) and DMAP (10 mg). The contents were stirred for 2 hrs. Trifluoroacetic acid (0.4 mL) was then added and stirring continued for an additional 30 minutes. After addition of satd NaHCO3 to neutralize the excess acid, ethyl acetate was then added and the organic layer separated, dried using magnesium sulfate and then concentrated under vacuum. The crude product was column chromatographed over silica gel using hexane/ethyl acetate (0-100%) to afford Intermediate 1A. 1H NMR (600 MHz, DMSO-d$_6$) δ ppm 0.72 (d, J=6.73 Hz, 3 H) 0.97 (d, J=6.73 Hz, 3 H) 2.09-2.22 (m, 1 H) 3.57 (dd, J=13.18, 4.98 Hz, 1 H) 3.72 (dd, J=13.61, 4.25 Hz, 1 H) 4.53 (dd, J=8.05, 3.95 Hz, 1 H) 7.20 (s, 1 H) 8.34 (d, J=4.98 Hz, 1 H) 9.08 (s, 1 H). LCMS (ESI) 265 (M+H).

Intermediate 1B

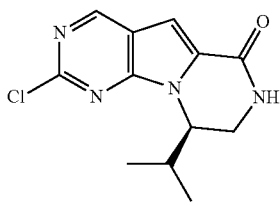 [SMILES: CC(C)[C@@H]1CNC(=O)c2cc3cnc(Cl)nc3n21]

Intermediate C was hydrogenated with 10% Pd/C to afford the intermediate tert-butyl N-[(2R)-2-amino-3-methyl-butyl] carbamate, which was then treated with 5-bromo-2,4-dichloro-pyrimidine using analogous reaction conditions as described for Intermediate 1A to afford intermediate 1B. The analytical data is consistent with that reported for the racemate (Intermediate 1A).

Intermediate 1C

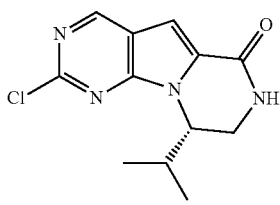 [SMILES: CC(C)[C@H]1CNC(=O)c2cc3cnc(Cl)nc3n21]

Intermediate D was hydrogenated with 10% Pd/C to afford the intermediate tert-butyl N-[(2S)-2-amino-3-methyl-butyl] carbamate, which was then treated with 5-bromo-2,4-dichloro-pyrimidine using analogous reaction conditions as described for Intermediate 1A to afford intermediate 1C. The analytical data (NMR and LCMS) was consistent with that reported for the racemate (intermediate 1A).

Intermediate 1CA

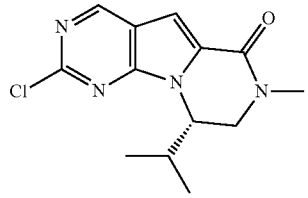 [SMILES: CC(C)[C@H]1CN(C)C(=O)c2cc3cnc(Cl)nc3n21]

To a solution of Intermediate 1A (80 mg, 0.00030 mole) in DMF (3 mL) was added a 60% dispersion of sodium hydride in oil (40 mg). After stirring for 15 minutes, methyl iodide (37 μL, 2 eq) was added. The contents were stirred at room temperature for 30 minutes. Satd NaHCO3 was then added followed by ethyl acetate. The organic layer was dried with magnesium sulfate and then concentrated under vacuum to afford intermediate 1AA. 1H NMR (600 MHz, DMSO-d$_6$) δ ppm 0.74 (d, J=6.73 Hz, 3 H) 0.91 (d, J=6.73 Hz, 3 H) 2.04-2.20 (m, 1 H) 3.04 (s, 3 H) 3.69 (dd, J=13.76, 1.17 Hz, 1 H) 3.96 (dd, J=13.76, 4.68 Hz, 1 H) 4.58 (dd, J=7.32, 3.51 Hz, 1 H) 7.16 (s, 1 H) 9.05 (s, 1 H). LCMS (ESI) 279 (M+H).

Intermediate 1D

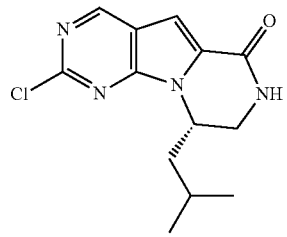 [SMILES: CC(C)C[C@H]1CNC(=O)c2cc3cnc(Cl)nc3n21]

tert-butyl N-[(2S)-2-[(5-bromo-2-chloro-pyrimidin-4-yl)amino]-4-methyl-pentyl]carbamate

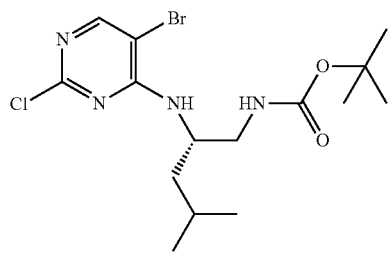 [SMILES: CC(C)C[C@@H](CNC(=O)OC(C)(C)C)Nc1nc(Cl)ncc1Br]

Intermediate G was hydrogenated with 10% Pd/C in ethanol under a blanket of hydrogen at 50 psi in a pressure bomb to afford tert-butyl N-[(2S)-2-amino-4-methyl-pentyl]carbamate which was then reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-4-methyl-pentyl]carbamate. 1H NMR (600 MHz, CHLOROFORM-d) δ ppm 0.91 (d, J=6.44 Hz, 3 H) 0.94 (d, J=6.44 Hz, 3 H) 1.32-1.51 (m, 11 H) 1.55-1.67 (m, 1 H) 3.28 (t, J=5.86 Hz, 2 H) 4.21-4.42 (m, 1 H) 4.84 (s, 1 H) 5.84 (d, J=7.32 Hz, 1 H) 8.07 (s, 1 H). LCMS (ESI) 407 (M+H).

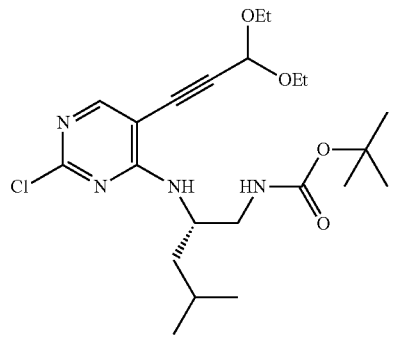 [SMILES: CCOC(C#Cc1cnc(Cl)nc1N[C@H](CNC(=O)OC(C)(C)C)CC(C)C)OCC]

To a solution of tert-butyl N-[(2S)-2-[(5-bromo-2-chloro-pyrimidin-4-yl)amino]-4-methyl-pentyl]carbamate 5.0 g (12.3 mmole) in toluene (36 mL) and triethyl amine (7.2 mL) was added under nitrogen, 3,3-diethoxyprop-1-yne 2.8 mL (19.7 mmole), Pd$_2$(dba)$_3$ 1.1 g (1.23 mmole), and triphenylarsine 3.8 g (12.3 mmole). The contents were heated to 70 degrees for 24 hrs. After cooling to room temperature, the reaction mixture was filtered through CELITE™ and then concentrated under vacuum. The crude product was columned over silica gel using hexane/ethyl acetate (0-30%) to afford (2S)-N2-[2-chloro-5-(3,3-diethoxyprop-1-ynyl)pyrimidin-4-yl]-4-methyl-pentane-1,2-diamine. LCMS (ESI) 455 (M+H).

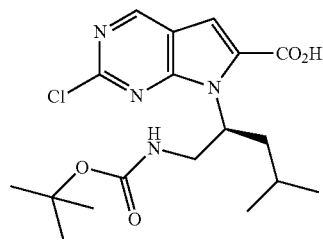 [SMILES: CC(C)C[C@@H](CNC(=O)OC(C)(C)C)n1c(C(=O)O)cc2cnc(Cl)nc21]

7-[(1S)-1-[(tert-butoxycarbonylamino)methyl]-3-methyl-butyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. 1H NMR (600 MHz, DMSO-d$_6$) δ ppm 0.88 (d, J=6.44 Hz, 3 H) 0.97 (d, J=6.44 Hz, 3 H) 1.47 (s, 9 H) 1.49-1.54 (m, 1 H) 1.56 (t, J=7.17 Hz, 2 H) 3.98 (dd, J=13.91, 3.07 Hz, 1 H) 3.76 (dd, J=13.31, 4.13 Hz, 1 H) 4.38 (d, J=14.05 Hz, 1 H) 4.90 (t, J=7.17 Hz, 1 H) 7.41 (s, 1 H) 9.11 (s, 1 H). LCMS (M+H) 397.

Intermediate 1D was synthesized using an analogous synthetic sequence as that described for intermediate 1A. 1H NMR (600 MHz, DMSO-d$_6$) δ ppm 0.82 (d, J=6.73 Hz, 3 H) 0.97 (d, J=6.44 Hz, 3 H) 1.34-1.46 (m, 1 H) 1.48-1.65 (m, 2 H) 3.40 (dd, J=13.32, 5.42 Hz, 1 H) 3.76 (dd, J=13.47, 4.10 Hz, 1 H) 4.76-4.92 (m, 1 H) 7.17 (s, 1 H) 8.34 (d, J=5.27 Hz, 1 H) 9.04 (s, 1 H). LCMS (ESI) 279 (M+H).

Intermediate 1DA

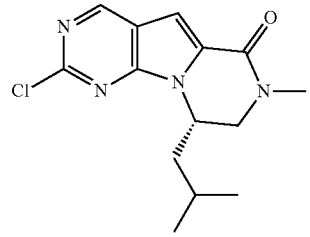 [SMILES: CC(C)C[C@H]1CN(C)C(=O)c2cc3cnc(Cl)nc3n21]

Intermediate 1DA was synthesized in a manner similar to that described for 1CA. 1H NMR (600 MHz, DMSO-d$_6$) δ ppm 0.82 (d, J=6.44 Hz, 3 H) 0.97 (d, J=6.44 Hz, 3 H) 1.37-1.68 (m, 3 H) 3.04 (s, 3 H) 3.56 (d, J=13.47 Hz, 1 H) 4.00 (dd, J=13.32, 4.25 Hz, 1 H) 4.82-4.94 (m, 1 H) 7.16 (s, 1 H) 9.03 (s, 1 H). LCMS (ESI) 293 (M+H)

Intermediate 1E

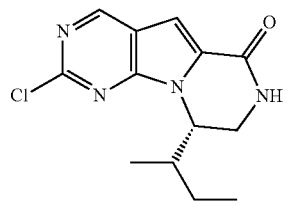 [SMILES: CCC(C)[C@H]1CNC(=O)c2cc3cnc(Cl)nc3n21]

tert-butyl N-[(2S)-2-[(5-bromo-2-chloro-pyrimidin-4-yl)amino]-3-methyl-pentyl]carbamate

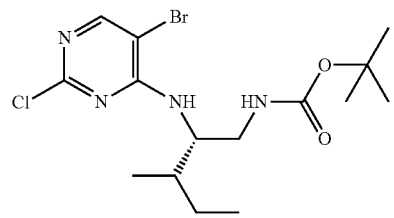 [SMILES: CCC(C)[C@@H](CNC(=O)OC(C)(C)C)Nc1nc(Cl)ncc1Br]

Intermediate I was hydrogenated using 10% Pd/C under hydrogen at 50 psi in a pressure vessel to afford tert-butyl N-[(2S)-2-amino-3-methyl-pentyl]carbamate which was reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-3-methyl-pentyl]carbamate. 1H NMR (600 MHz, CHLOROFORM-d) δ ppm 0.88-0.95 (m, 6 H) 1.11-1.20 (m, 1 H) 1.34 (s, 9 H) 1.44-1.54 (m, 1 H)

1.64-1.72 (m, 1 H) 3.17-3.27 (m, 1 H) 3.33-3.43 (m, 1 H) 4.11-4.21 (m, 1 H) 4.81 (s, 1 H) 5.92 (d, J=8.20 Hz, 1 H) 8.05 (s, 1 H). LCMS (ESI) 407.

tert-butyl N-[(2S)-2-[[2-chloro-5-(3,3-diethoxyprop-1-ynyl)pyrimidin-4-yl]amino]-3-methyl-pentyl]carbamate

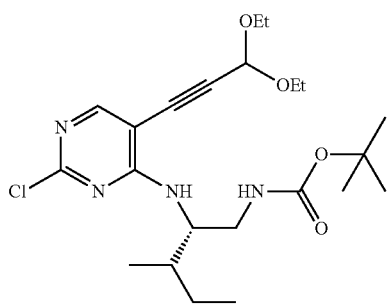 [SMILES: CCOC(C#Cc1cnc(Cl)nc1N[C@H](CNC(=O)OC(C)(C)C)C(C)CC)OCC]

tert-butyl N-[(2S)-2-[[2-chloro-5-(3,3-diethoxyprop-1-ynyl)pyrimidin-4-yl]amino]-3-methyl-pentyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. 1H NMR (600 MHz, DMSO-$d_6$) δ ppm 0.76-0.89 (m, 6H) 1.03 (q, J=7.22 Hz, 3 H) 1.10-1.17 (m, 3 H) 1.25-1.42 (m, 11 H) 1.59-1.73 (m, 1 H) 3.35-3.47 (m, 4 H) 3.51-3.73 (m, 2 H) 3.99-4.11 (m, 1 H) 5.52-5.56 (m, 1 H) 6.76-7.03 (m, 2 H) 8.12-8.23 (m, 1 H). LCMS (ESI) 455 (M+H).

7-[(1S)-1-[(tert-butoxycarbonylamino)methyl]-2-methyl-butyl]-2-chloro-pyrrolo[2,3-d]pyrimidine-6-carboxylic acid

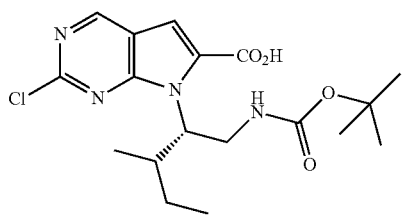 [SMILES: CCC(C)[C@@H](CNC(=O)OC(C)(C)C)n1c(C(=O)O)cc2cnc(Cl)nc21]

7-[(1S)-1-[(tert-butoxycarbonylamino)methyl]-2-methyl-butyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. 1H NMR (600 MHz, DMSO-$d_6$) δ ppm 0.80 (t, J=7.47 Hz, 3 H) 0.86 (d, J=7.03 Hz, 3 H) 1.06-1.30 (m, 2 H) 1.48 (s, 9 H) 1.79-1.96 (m, 1 H) 3.95 (dd, J=14.05, 3.22 Hz, 1 H) 4.52 (d, J=14.35 Hz, 1 H) 4.61-4.73 (m, 1 H) 7.43 (s, 1 H) 9.13 (s, 1 H). LCMS (ESI) 397 (M+H).

Intermediate 1E was synthesized using an analogous synthetic sequence as that described for intermediate 1A. 1H NMR (600 MHz, DMSO-$d_6$) δ ppm 0.74 (t, J=7.32 Hz, 3 H) 0.89 (d, J=6.73 Hz, 3 H) 1.00-1.12 (m, 2 H) 1.82-1.94 (m, 1 H) 3.55 (dd, J=13.91, 4.83 Hz, 1 H) 3.70 (dd, J=13.61, 4.25 Hz, 1 H) 4.57 (dd, J=7.91, 4.10 Hz, 1 H) 7.17 (s, 1 H) 8.31 (d, J=5.27 Hz, 1 H) 9.05 (s, 1 H). LCMS (ESI) 279 (M+H).

Intermediate 1EA

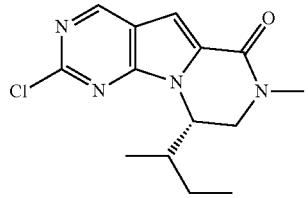 [SMILES: CCC(C)[C@H]1CN(C)C(=O)c2cc3cnc(Cl)nc3n21]

Intermediate 1EA was synthesized in a manner similar to Intermediate 1CA. 1H NMR (600 MHz, DMSO-$d_6$) δ ppm 0.77 (t, J=7.47 Hz, 3 H) 0.84 (d, J=6.73 Hz, 3 H) 1.07-1.16 (m, 2 H) 1.82-1.95 (m, 1 H) 3.03 (s, 3 H) 3.68 (d, J=13.76 Hz, 1 H) 3.96 (dd, J=13.76, 4.39 Hz, 1 H) 4.59-4.70 (m, 1 H) 7.16 (s, 1 H) 9.04 (s, 1 H). LCMS (ESI) 293 (M+H).

Intermediate 1F

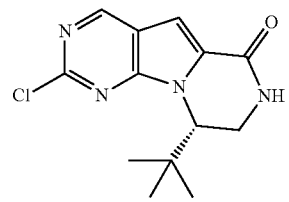 [SMILES: CC(C)(C)[C@H]1CNC(=O)c2cc3cnc(Cl)nc3n21]

tert-butyl N-[(2S)-2-[(5-bromo-2-chloro-pyrimidin-4-yl)amino]-3,3-dimethyl-butyl]carbamate

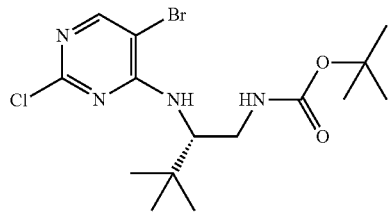 [SMILES: CC(C)(C)OC(=O)NC[C@@H](Nc1nc(Cl)ncc1Br)C(C)(C)C]

Intermediate J was hydrogenated using 10% Pd/C under hydrogen at 50 psi in a pressure vessel to afford tert-butyl N-[(2S)-2-amino-3,3-dimethyl-butyl]carbamate which was then reacted with 5-bromo-2,4-dichloro-pyrimidine using analogous reaction conditions as described using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-3,3-dimethyl-butyl]carbamate. LCMS (ESI) 407 (M+H).

tert-butyl N-[(2S)-2-[[2-chloro-5-(3,3-diethoxyprop-1-ynyl)pyrimidin-4-yl]amino]-3,3-dimethyl-butyl]carbamate

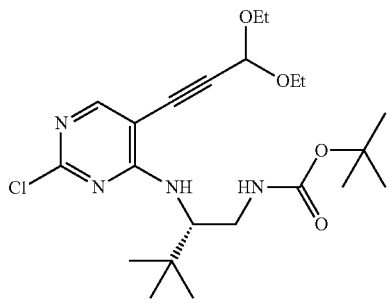 [SMILES: CCOC(C#Cc1cnc(Cl)nc1N[C@H](CNC(=O)OC(C)(C)C)C(C)(C)C)OCC]

tert-butyl N-[(2S)-2-[[2-chloro-5-(3,3-diethoxyprop-1-ynyl)pyrimidin-4-yl]amino]-3,3-dimethyl-butyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. LCMS (ESI) 455 (M+H).

7-[(1S)-1-[(tert-butoxycarbonylamino)methyl]-2,2-dimethyl-propyl]-2-chloro-pyrrolo[2,3-d]pyrimidine-6-carboxylic acid

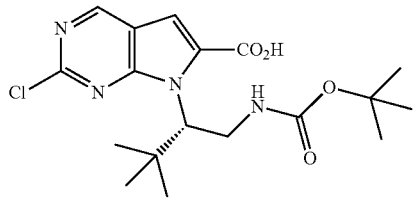 [SMILES: CC(C)(C)OC(=O)NC[C@@H](n1c(C(=O)O)cc2cnc(Cl)nc21)C(C)(C)C]

7-[(1S)-1-[(tert-butoxycarbonylamino)methyl]-2,2-dimethyl-propyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 397 (M+H).

Intermediate 1F was synthesized using an analogous synthetic sequence as that described for intermediate 1A. LCMS (ESI) 279 (M+H).

Intermediate 1FA

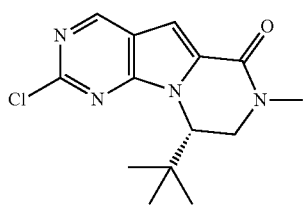 [SMILES: CN1C[C@H](C(C)(C)C)n2c(cc3cnc(Cl)nc32)C1=O]

Intermediate 1FA was synthesized in a manner similar to that described for Intermediate 1CA. LCMS (ESI) 293 (M+H).

Intermediate 1G

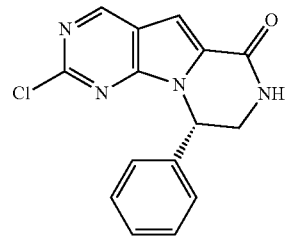 [SMILES: O=C1NC[C@H](c2ccccc2)n2c1cc1cnc(Cl)nc12]

tert-butyl N-[(2S)-2-[(5-bromo-2-chloro-pyrimidin-4-yl)amino]-2-phenyl-ethyl]carbamate

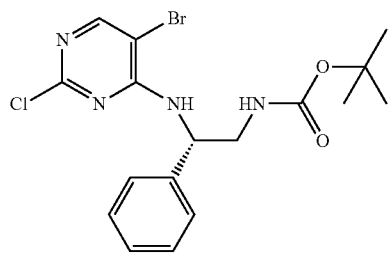 [SMILES: CC(C)(C)OC(=O)NC[C@@H](Nc1nc(Cl)ncc1Br)c1ccccc1]

Intermediate J was hydrogenated using 10% Pd/C under hydrogen at 50 psi in a pressure vessel to afford tert-butyl N-[(2S)-2-amino-2-phenyl-ethyl]carbamate which was then reacted with 5-bromo-2,4-dichloro-pyrimidine using analogous reaction conditions as described using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-2-phenyl-ethyl]carbamate. 1H NMR (600 MHz, DMSO-d$_6$) δ ppm 1.32 (s, 9 H) 3.29-3.50 (m, 2 H) 5.12-5.24 (m, 1 H) 7.10 (t, J=5.27 Hz, 1 H) 7.21 (t, J=6.88 Hz, 1 H) 7.26-7.34 (m, 4 H) 7.89 (d, J=7.32 Hz, 1 H) 8.24 (s, 1 H). LCMS (ESI) 427 (M+H).

tert-butyl N-[(2S)-2-[[2-chloro-5-(3,3-diethoxyprop-1-ynyl)pyrimidin-4-yl]amino]-2-phenyl-ethyl]carbamate

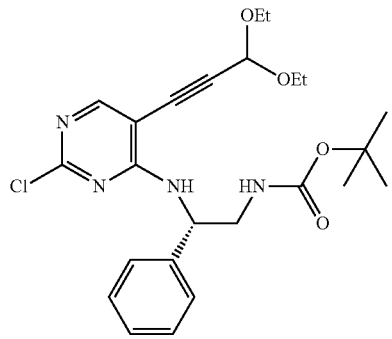 [SMILES: CCOC(C#Cc1cnc(Cl)nc1N[C@H](CNC(=O)OC(C)(C)C)c1ccccc1)OCC]

tert-butyl N-[(2S)-2-[[2-chloro-5-(3,3-diethoxyprop-1-ynyl)pyrimidin-4-yl]amino]-2-phenyl-ethyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. 1H NMR (600 MHz, DMSO-d₆) δ ppm 1.14 (t, J=7.03 Hz, 6 H) 1.32 (s, 9 H) 3.39 (s, 2 H) 3.52-3.61 (m, 2 H) 3.64-3.73 (m, 2 H) 5.17-5.26 (m, 1 H) 5.57 (s, 1 H) 7.07-7.14 (m, 1 H) 7.20-7.25 (m, 1 H) 7.26-7.33 (m, 4 H) 7.90 (d, J=7.61 Hz, 1 H) 8.19 (s, 1 H). LCMS (ESI) 475 (M+H).

7-[(1S)-2-(tert-butoxycarbonylamino)-1-phenyl-ethyl]-2-chloro-pyrrolo[2,3-d]pyrimidine-6-carboxylic acid

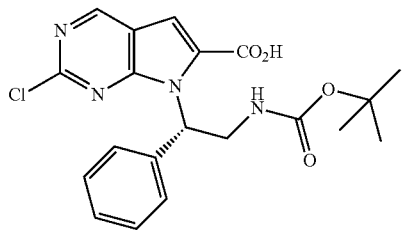 [SMILES: CC(C)(C)OC(=O)NC[C@H](c1ccccc1)n1c(C(=O)O)cc2cnc(Cl)nc21]

7-[(1S)-2-(tert-butoxycarbonylamino)-1-phenyl-ethyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 417 (M+H).

Intermediate 1G

Intermediate 1G was synthesized using an analogous synthetic sequence as that described for intermediate 1A. 1H NMR (600 MHz, DMSO-d₆) δ ppm 3.58-3.69 (m, 1 H) 4.13 (dd, J=13.47, 4.39 Hz, 1 H) 6.07 (d, J=3.81 Hz, 1 H) 6.85 (d, J=7.32 Hz, 2 H) 7.19-7.31 (m, 3 H) 7.34 (s, 1 H) 8.27 (d, J=5.27 Hz, 1 H) 9.13 (s, 1 H). LCMS (ESI) 299 (M+H).

Intermediate 1H

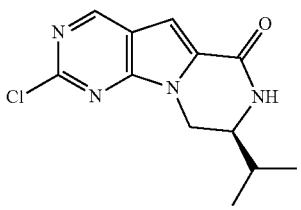 [SMILES: CC(C)[C@H]1Cn2c(cc3cnc(Cl)nc32)C(=O)N1]

tert-butyl N-[(1S)-1-[[(5-bromo-2-chloro-pyrimidin-4-yl)amino]methyl]-2-methyl-propyl]carbamate

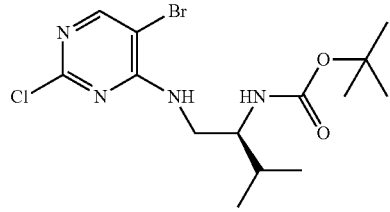 [SMILES: CC(C)[C@@H](CNc1nc(Cl)ncc1Br)NC(=O)OC(C)(C)C]

tert-butyl N-[(1S)-1-[[(5-bromo-2-chloro-pyrimidin-4-yl)amino]methyl]-2-methyl-propyl]carbamate was synthesized using 5-bromo-2,4-dichloro-pyrimidine and Intermediate E using analogous reaction conditions as described for tert-butyl N-[2-[(5-bromo-2-chloro-pyrimidin-4-yl)amino]-3-methyl-butyl]carbamate. 1H NMR (600 MHz, CHLOROFORM-d) δ ppm 0.95-1.02 (m, 6 H) 1.35-1.45 (m, 9 H) 1.75-1.90 (m, 1 H) 3.35-3.48 (m, 1 H) 3.52-3.61 (m, 1 H) 3.64-3.76 (m, 1 H) 4.56 (d, J=8.49 Hz, 1 H) 6.47 (s, 1 H) 8.07 (s, 1 H). LCMS (ESI) 393 (M+H).

tert-butyl N-[(1S)-1-[[[2-chloro-5-(3,3-diethoxyprop-1-ynyl)pyrimidin-4-yl]amino]methyl]-2-methyl-propyl]carbamate

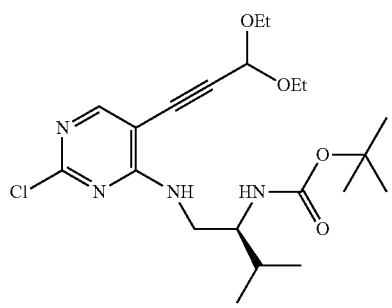 [SMILES: CCOC(C#Cc1cnc(Cl)nc1NC[C@@H](NC(=O)OC(C)(C)C)C(C)C)OCC]

tert-butyl N-[(1S)-1-[[[2-chloro-5-(3,3-diethoxyprop-1-ynyl)pyrimidin-4-yl]amino]methyl]-2-methyl-propyl]carbamate was synthesized using similar experimental conditions to that used in the synthesis (2S)-N2-[2-chloro-5-(3,3-diethoxyprop-1-ynyl)pyrimidin-4-yl]-4-methyl-pentane-1,2-diamine. 1H NMR (600 MHz, CHLOROFORM-d) δ ppm 0.90-1.00 (m, 6 H) 1.18-1.25 (m, 6 H) 1.34-1.36 (m, 9 H) 1.69-1.90 (m, 1 H) 3.34-3.82 (m, 6 H) 4.53-4.77 (m, 1 H) 5.45-5.55 (m, 1 H) 6.37 (dd, J=15.37, 6.59 Hz, 1 H) 6.56 (s, 1 H) 8.05 (s, 1 H). LCMS (ESI) 441 (M+H).

7-[(2S)-2-(tert-butoxycarbonylamino)-3-methyl-butyl]-2-chloro-pyrrolo[2,3-d]pyrimidine-6-carboxylic acid

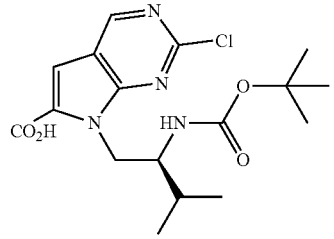 [SMILES: CC(C)[C@@H](Cn1c(C(=O)O)cc2cnc(Cl)nc21)NC(=O)OC(C)(C)C]

7-[(2S)-2-(tert-butoxycarbonylamino)-3-methyl-butyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. 1H NMR (600 MHz, CHLOROFORM-d) δ ppm 0.90 (d, J=6.73 Hz, 3 H) 0.96 (d, J=7.03 Hz, 3 H) 1.55-1.66 (m, 10 H) 4.14 (dd, J=13.61, 3.95 Hz, 1 H) 4.52-4.63 (m, 1 H) 4.84 (dd, J=13.61, 1.32 Hz, 1 H) 7.37 (s, 1 H) 8.95 (s, 1 H). LCMS (ESI) 383 (M+H).

Intermediate H

Intermediate 1H was synthesized using an analogous synthetic sequence as that described for intermediate 1A. LCMS (ESI) 265 (M+H).

Intermediate 1I

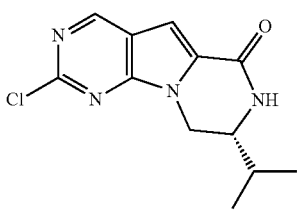 [SMILES: CC(C)[C@@H]1Cn2c(cc3cnc(Cl)nc32)C(=O)N1]

Intermediate 1I was synthesized using 5-bromo-2,4-dichloro-pyrimidine and Intermediate F as starting materials, and following a similar sequence of synthetic steps as for intermediate 1H. The analytical data was consistent with that described for its antipode (intermediate 1 H). 1H NMR (600 MHz, DMSO-$d_6$) δ ppm 0.88 (d, J=6.44 Hz, 6 H) 1.73-1.86 (m, 1 H) 3.67-3.76 (m, 2 H) 4.11-4.21 (m, 1 H) 7.13-7.19 (m, 1 H) 8.56 (s, 1 H) 9.05 (s, 1 H). LCMS (ESI) 265 (M+H).

Intermediate 1J

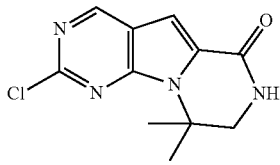 [SMILES: CC1(C)CNC(=O)c2cc3cnc(Cl)nc3n21]

tert-butyl N-[2-[(5-bromo-2-chloro-pyrimidin-4-yl)amino]-2-methyl-propyl]carbamate

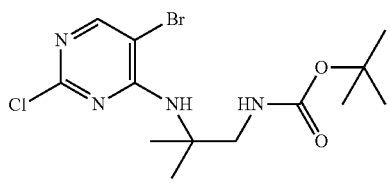 [SMILES: CC(C)(CNC(=O)OC(C)(C)C)Nc1nc(Cl)ncc1Br]

tert-butyl N-[2-[(5-bromo-2-chloro-pyrimidin-4-yl)amino]-2-methyl-propyl]carbamate was synthesized using 5-bromo-2,4-dichloro-pyrimidine and tert-butyl N-(2-amino-2-methyl-propyl)carbamate using analogous reaction conditions as described for tert-butyl N-[2-[(5-bromo-2-chloro-pyrimidin-4-yl)amino]-3-methyl-butyl]carbamate. LCMS (ESI) 379 (M+H).

tert-butyl N-[2-[[2-chloro-5-(3,3-diethoxyprop-1-ynyl)pyrimidin-4-yl]amino]-2-methyl-propyl]carbamate

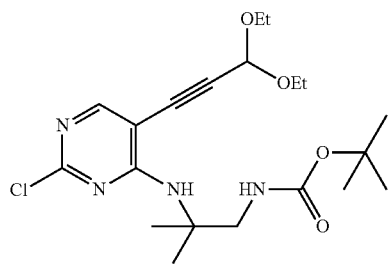 [SMILES: CCOC(C#Cc1cnc(Cl)nc1NC(C)(C)CNC(=O)OC(C)(C)C)OCC]

tert-butyl N-[2-[[2-chloro-5-(3,3-diethoxyprop-1-ynyl)pyrimidin-4-yl]amino]-2-methyl-propyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. 1H NMR (600 MHz, DMSO-$d_6$) d ppm 1.11-1.22 (m, 6 H) 1.31-1.45 (m, 15 H) 3.10-3.24 (m, 2 H) 3.51-3.76 (m, 4 H) 5.60 (s, 1 H) 6.94 (s, 1 H) 7.33 (t, J=6.44 Hz, 1 H) 8.18 (s, 1 H). LCMS (ESI) 427 (M+H).

7-[2-(tert-butoxycarbonylamino)-1,1-dimethyl-ethyl]-2-chloro-pyrrolo[2,3-d]pyrimidine-6-carboxylic acid

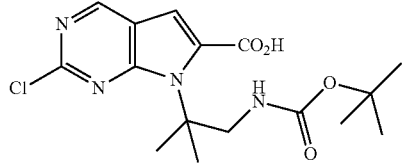 [SMILES: CC(C)(C)OC(=O)NCC(C)(C)n1c(C(=O)O)cc2cnc(Cl)nc21]

7-[2-(tert-butoxycarbonylamino)-1,1-dimethyl-ethyl]-2-chloro-pyrrolo[2,3-d]pyrimidine-6-carboxylic acid using analogous synthetic sequence as that described for 7-[1-[(tert-butoxycarbonylamino)methyl]-2-methyl-propyl]-2-chloro-pyrrolo[2,3-d]pyrimidine-6-carboxylic acid. 1H NMR (600 MHz, DMSO-$d_6$) δ ppm 1.43 (s, 9H) 1.73 (s, 6 H) 4.06 (s, 2 H) 7.46 (s, 1 H) 9.23 (s, 1H). LCMS (ESI) 369 (M+H).

Intermediate 1J

Intermediate 1J was synthesized using an analogous synthetic sequence as that described for intermediate 1A. 1H NMR (600 MHz, DMSO-$d_6$) δ ppm 1.73 (s, 6 H) 3.50 (d, J=2.93 Hz, 2 H) 7.25 (s, 1 H) 8.46-8.55 (m, 1 H) 9.07 (s, 1 H). LCMS (ESI) 251 (M+H).

Intermediate 1K

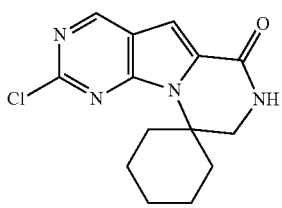 [SMILES: O=C1NCC2(CCCCC2)n2c1cc1cnc(Cl)nc12]

tert-butyl N-[[1-[(5-bromo-2-chloro-pyrimidin-4-yl)amino]cyclohexyl]methyl]carbamate

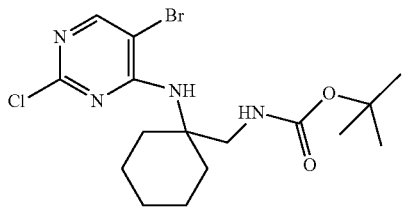 [SMILES: CC(C)(C)OC(=O)NCC1(Nc2nc(Cl)ncc2Br)CCCCC1]

tert-butyl N-[[1-[(5-bromo-2-chloro-pyrimidin-4-yl)amino]cyclohexyl]methyl]carbamate was synthesized using 5-bromo-2,4-dichloro-pyrimidine and Intermediate K using analogous reaction conditions as described for tert-butyl N-[2-[(5-bromo-2-chloro-pyrimidin-4-yl)amino]-3-methyl-butyl]carbamate. 1H NMR (600 MHz, DMSO-$d_6$) δ ppm 1.18-1.54 (m, 17 H) 2.23 (d, J=14.35 Hz, 2 H) 3.36 (d, J=6.44 Hz, 2 H) 5.82 (s, 1 H) 6.93 (s, 1 H) 8.22 (s, 1 H). LCMS (ESI) 419 (M+H).

tert-butyl N-[[1-[[2-chloro-5-(3,3-diethoxyprop-1-ynyl)pyrimidin-4-yl]amino]cyclohexyl]methyl]carbamate

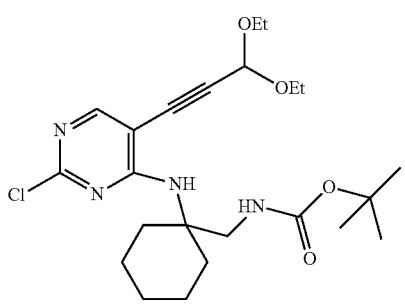 [SMILES: CCOC(C#Cc1cnc(Cl)nc1NC1(CNC(=O)OC(C)(C)C)CCCCC1)OCC]

tert-butyl N-[[1-[[2-chloro-5-(3,3-diethoxyprop-1-ynyl)pyrimidin-4-yl]amino]cyclohexyl]methyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. 1H NMR (600 MHz, DMSO-$d_6$) d ppm 1.08-1.16 (m, 6 H) 1.17-1.54 (m, 17 H) 2.13 (br. s., 2 H) 3.36 (d, J=6.73 Hz, 2 H) 3.50-3.69 (m, 4 H) 5.72 (s, 1 H) 6.94 (s, 1 H) 5.72 (br. s., 1 H) 8.17 (s, 1 H). LCMS (ESI) 467 (M+H).

7-[1-[(tert-butoxycarbonylamino)methyl]cyclohexyl]-2-chloro-pyrrolo[2,3-d]pyrimidine-6-carboxylic acid

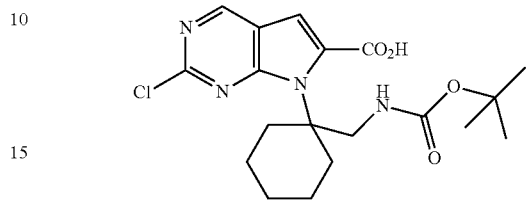

7-[1-[(tert-butoxycarbonylamino)methyl]cyclohexyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. 1H NMR (600 MHz, DMSO-$d_6$) δ ppm 1.37-1.54 (m, 13 H) 1.75 (br. s., 4 H) 2.74 (br. s., 2 H) 3.78-3.84 (m, 2 H) 7.44-7.51 (m, 1 H) 8.23 (s, 1 H) 9.11 (s, 1 H). LCMS (ESI) 409 (M+H).

Intermediate K

Intermediate 1K was synthesized using an analogous synthetic sequence as that described for intermediate 1A. 1H NMR (600 MHz, DMSO-$d_6$) δ ppm 1.28 (br. s., 2 H) 1.42 (br. s., 2 H) 1.70 (br. s., 4 H) 1.85-1.95 (m, 2 H) 2.69 (m, 2 H) 7.16-7.25 (m, 1 H) 8.41 (br. s., 1 H) 9.04 (s, 1 H). LCMS 291 (M+H).

Intermediate 1L

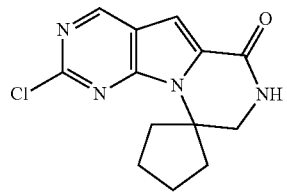 [SMILES: O=C1NCC2(CCCC2)n2c1cc1cnc(Cl)nc12]

tert-butyl N-[[1-[(5-bromo-2-chloro-pyrimidin-4-yl)amino]cyclopentyl]methyl]carbamate

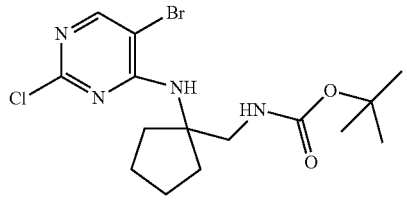 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl]methyl]carbamate was synthesized using 5-bromo-2,4-dichloro-pyrimidine and Intermediate L using analogous reaction conditions as described for tert-butyl N-[2-[(5-bromo-2-chloro-pyrimidin-4-yl)amino]-3-methyl-butyl]carbamate. 1H NMR (600 MHz, DMSO-$d_6$) δ ppm 1.34 (s, 9 H) 1.50-1.58 (m, 2 H) 1.63-1.78 (m, 4 H) 1.96-2.06 (m, 2 H) 3.25 (d, J=6.15 Hz, 2 H) 6.71 (s, 1 H) 7.18 (t, J=6.29 Hz, 1 H) 8.20 (s, 1 H). LCMS (ESI) 405 (M+H).

tert-butyl N-[[1-[[2-chloro-5-(3,3-diethoxyprop-1-ynyl)pyrimidin-4-yl]amino]cyclopentyl]methyl]carbamate

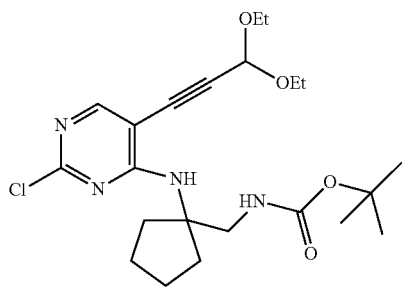 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. LCMS (ESI) 453 (M+H).

7-[1-[(tert-butoxycarbonylamino)methyl]cyclopentyl]-2-chloro-pyrrolo[2,3-d]pyrimidine-6-carboxylic acid

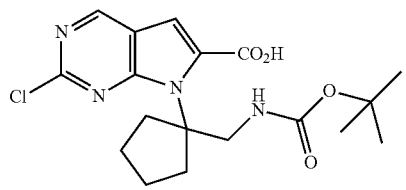 [SMILES: CC(C)(C)OC(=O)NCC1(n2c(C(=O)O)cc3cnc(Cl)nc32)CCCC1]

7-[1-[(tert-butoxycarbonylamino)methyl]cyclopentyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. 1H NMR (600 MHz, DMSO-$d_6$) δ ppm 1.47 (s, 9 H) 1.74 (br. s., 2 H) 1.88 (br. s., 2 H) 2.04 (br. s., 2 H) 2.41-2.45 (m, 2 H) 4.06 (s, 2 H) 7.45 (s, 1 H) 9.11 (s, 1 H). LCMS (ESI) 395 (M+H).

Intermediate 1L

Intermediate 1L was synthesized using an analogous synthetic sequence as that described for intermediate 1A. 1H NMR (600 MHz, DMSO-$d_6$) δ ppm 1.72 (br. s., 2 H) 1.86 1.93 (m, 2 H) 1.99 (d, J=3.81 Hz, 2 H) 2.40 (br. s., 2 H) 3.48 (d, J=2.34 Hz, 2 H) 7.22 (s, 1 H) 8.53 (br. s., 1 H) 9.05 (s, 1 H). LCMS (ESI) 277 (M+H).

Intermediate 1M

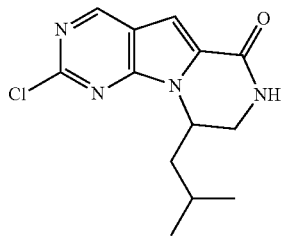 [SMILES: CC(C)CC1CNC(=O)c2cc3cnc(Cl)nc3n21]

tert-butyl N-[2-[(5-bromo-2-chloro-pyrimidin-4-yl)amino]-4-methyl-pentyl]carbamate

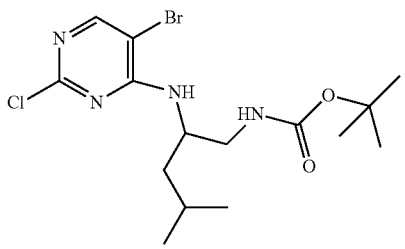 [SMILES: CC(C)CC(CNC(=O)OC(C)(C)C)Nc1nc(Cl)ncc1Br]

tert-butyl N-[2-[(5-bromo-2-chloro-pyrimidin-4-yl)amino]-4-methyl-pentyl]carbamate was synthesized using 5-bromo-2,4-dichloro-pyrimidine and Intermediate B using analogous reaction conditions as described for tert-butyl N-[2-[(5-bromo-2-chloro-pyrimidin-4-yl)amino]-3-methyl-butyl]carbamate. The analytical data is consistent with that described for the L-enantiomer.

tert-butyl N-[2-[[2-chloro-5-(3,3-diethoxyprop-1-ynyl)pyrimidin-4-yl]amino]-4-methyl-pentyl]carbamate

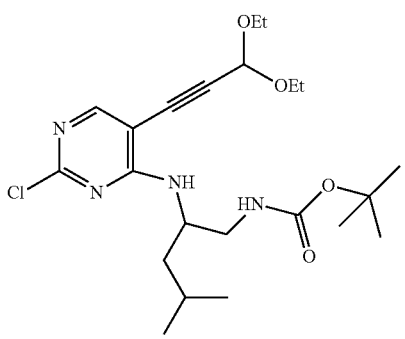 [SMILES: CCOC(C#Cc1cnc(Cl)nc1NC(CNC(=O)OC(C)(C)C)CC(C)C)OCC]

tert-butyl N-[2-[[2-chloro-5-(3,3-diethoxyprop-1-ynyl)pyrimidin-4-yl]amino]-4-methyl-pentyl]carbamate was synthesized using similar experimental conditions to that used in the synthesis of tert-butyl N-[2-[[2-chloro-5-(3,3-diethoxyprop-1-ynyl)pyrimidin-4-yl]amino]ethyl]carbamate. 1H NMR (600 MHz, CHLOROFORM-d) δ ppm 1.21-1.31 (m, 12 H) 1.38-1.46 (m, 11 H) 1.70 (m, 1H) 3.24 (m, 2 H) 3.65-3.82 (m, 4 H) 4.86 (br s., 1H), 5.65 (s, 1 H) 5.85 (br s., 1H) 6.94 (s, 1 H) 8.21 (s, 1 H). LCMS (ESI) 455 (M+H).

7-[1-[(tert-butoxycarbonylamino)methyl]-3-methyl-butyl]-2-chloro-pyrrolo[2,3-d]pyrimidine-6-carboxylic acid

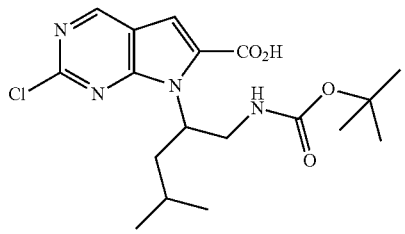 [SMILES: CC(C)CC(CNC(=O)OC(C)(C)C)n1c(C(=O)O)cc2cnc(Cl)nc21]

7-[1-[(tert-butoxycarbonylamino)methyl]-3-methyl-butyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. The analytical data was consistent with that described for the L-isomer.

Intermediate 1M

Intermediate 1M was synthesized using an analogous synthetic sequence as that described for intermediate 1A. The analytical data was consistent with that described for the L-isomer.

Intermediate 1MA

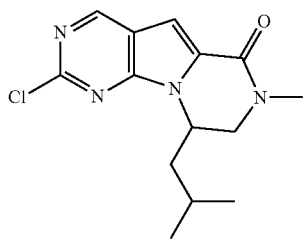

To a solution of Intermediate 1M (100 mg, 0.00024 mole) in DMF (3.0 mL) was added sodium hydride (60% dispersion in oil), (27.6 mg, 3 eq). After stirring for 15 mins, methyl iodide (30, 2 eq) was added. The contents were stirred at room temperature for 30 mins. After the addition of sat NaHCO₃, ethyl acetate was added. Separation of the organic layer followed by drying with magnesium sulfate and concentration under vacuum afforded the intermediate 1MA. Analytical data was similar to the Intermediate 1DA.

Intermediate 1N

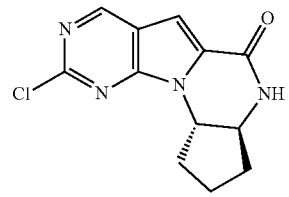 [SMILES: O=C1N[C@H]2CCC[C@@H]2n2c1cc1cnc(Cl)nc12]

tert-butyl N-[(1S,2S)-2-[(5-bromo-2-chloro-pyrimidin-4-yl)amino]cyclopentyl]carbamate

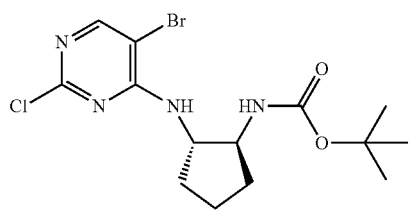 [SMILES: CC(C)(C)OC(=O)N[C@H]1CCC[C@@H]1Nc1nc(Cl)ncc1Br]

tert-butyl N-[(1S,2S)-2-[(5-bromo-2-chloro-pyrimidin-4-yl)amino]cyclopentyl]carbamate was synthesized by treating tert-butyl N-[(1S,2S)-2-aminocyclopentyl]carbamate with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate.
1H NMR (600 MHz, DMSO-d₆) δ ppm 1.27 (s, 9 H) 1.42-1.54 (m, 2 H) 1.56-1.65 (m, 2 H) 1.80-1.88 (m, 1 H) 1.96-2.01 (m, 1 H) 3.88-3.96 (m, 1 H) 4.03-4.09 (m, 1 H) 6.91 (d, J=8.20 Hz, 1 H) 7.41 (d, J=7.32 Hz, 1 H) 8.18 (s, 1 H). LCMS (ESI) 391 (M+H).

tert-butyl N-[(1S,2S)-2-[[2-chloro-5-(3,3-diethoxyprop-1-ynyl)pyrimidin-4-yl]amino]cyclopentyl]carbamate

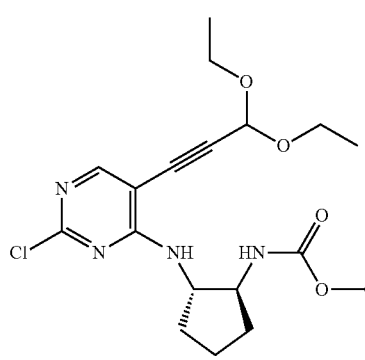

tert-butyl N-[(1S,2S)-2-[[2-chloro-5-(3,3-diethoxyprop-1-ynyl)pyrimidin-4-yl]amino]cyclopentyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. 1H NMR (600 MHz, DMSO-$d_6$) δ ppm 1.13 (t, 6 H) 1.28 (s, 9 H) 1.42-1.52 (m, 2 H) 1.58-1.65 (m, 2 H) 1.81-1.90 (m, 1 H) 1.99-2.08 (m, 1 H) 3.49-3.60 (m, 2 H) 3.63-3.71 (m, 2 H) 3.84-3.93 (m, 1 H) 3.96-4.04 (m, 1 H) 5.53 (s, 1 H) 6.96 (d, J=7.90 Hz, 1 H) 7.34 (d, J=7.03 Hz, 1 H) 8.14 (s, 1 H). LCMS (ESI) 439 (M+H).

7-[(1S,2S)-2-(tert-butoxycarbonylamino)cyclopentyl]-2-chloro-pyrrolo[2,3-d]pyrimidine-6-carboxylic acid

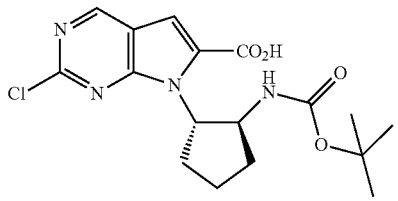 [SMILES: CC(C)(C)OC(=O)N[C@H]1CCC[C@@H]1n1c(C(=O)O)cc2cnc(Cl)nc21]

7-[(1S,2S)-2-(tert-butoxycarbonylamino)cyclopentyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. 1H NMR (600 MHz, DMSO-$d_6$) δ ppm 1.41-1.52 (m, 9 H) 1.55-1.68 (m, 1 H) 1.88-2.00 (m, 2 H) 2.05-2.15 (m, 1 H) 2.26-2.35 (m, 1 H) 2.71-2.89 (m, 1 H) 4.01-4.16 (m, 1 H) 4.28-4.45 (m, 1 H) 7.41 (s, 1 H) 9.11 (s, 1 H). LCMS (ESI) 381 (M+H).

Intermediate 1N

Intermediate 1N was synthesized using an analogous synthetic sequence as that described for intermediate 1A. 1H NMR (600 MHz, DMSO-$d_6$) δ ppm 1.48-1.60 (m, 1 H) 1.88-1.98 (m, 3 H) 1.99-2.08 (m, 1 H) 2.66-2.75 (m, 1 H) 3.63-3.74 (m, 1 H) 3.99-4.12 (m, 1 H) 7.21 (s, 1 H) 8.89 (s, 1 H) 9.04 (s, 1 H). LCMS (ESI) 263 (M+H).

Example 3

Example Compounds

Compound 1

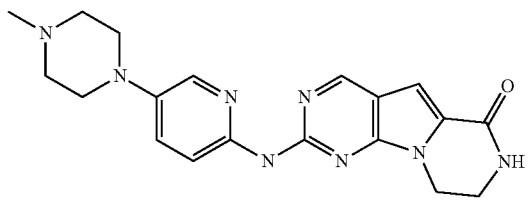

To 0.050 g (0.225 mmole) chloro tricycliclactam in dioxane (2.0 mL) under nitrogen was added 5-(4-methylpiperazin-1-yl)pyridin-2-amine 0.052 g (1.2 eq, 0.270 mmole) followed by the addition of Pd$_2$(dba)$_3$ (18.5 mg), BINAP (25 mg) and sodium-tert-butoxide (31 mg, 0.324 mmole). The contents of the flask are degassed for 10 minutes and then heated to 100 degrees for 12 hours. The crude reaction was loaded on a silica gel column and eluted with DCM/MeOH (0-15%) to afford the desired product (26 mg). To this compound dissolved in DCM/MeOH (10%) was added 3N HCl in iso-propanol (2 eq) and stirred overnight. Concentration under vacuum afforded the hydrochloride salt. $^1$HNMR (d6-DMSO) 11.13 (brs, 1H), 9.07 (s, 1H), 8.42 (s, 1H), 8.03 (br m 1H), 7.99 (s, 1H), 7.67 (brm, 1H), 7.18 (s, 1H), 4.33 (m, 2H), 3.79 (m, 2H), 3.64 (m, 2H), 3.50 (m, 2H), 3.16 (m, 4H), 2.79 (s, 3H). LCMS (ESI) 379 (M+H)

Compound 2

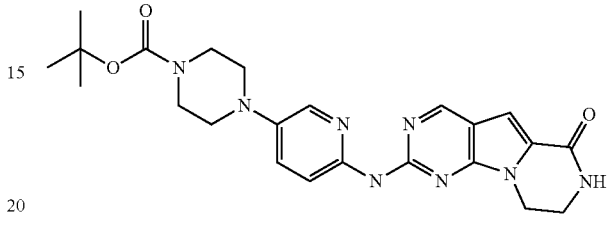

To chloro tricycliclactam 0.075 g (0.338 mmole) in dioxane 3.5 mL under nitrogen was added tert-butyl 4-(6-amino-3-pyridyl)piperazine-1-carboxylate 0.098 g (1.05 eq) followed by the addition of Pd$_2$(dba)$_3$ (27 mg) and BINAP (36 mg) and sodium-tert-butoxide (45 mg). The contents were refluxed for 11 hrs. The crude reaction was loaded on a silica gel column and eluted with DCM/MeOH (0-10%) to afford the desired product (32 mg). $^1$HNMR (d6-DMSO) 9.48 (s, 1H), 8.84 (s, 1H), 8.29 (s, 1H), 8.18 (s, 1H), 7.99 (s, 1H), 7.42 (m, 1H), 6.98 (s, 1H), 4.23 (m, 2H), 3.59 (m, 2H), 3.45 (m, 4H), 3.50 (m, 2H), 3.05 (m, 4H). LCMS (ESI) 465 (M+H)

Compound 3

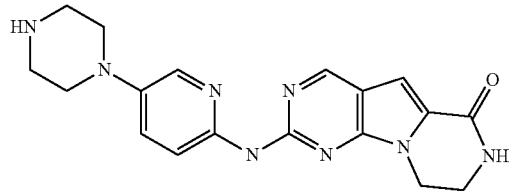

To a solution of Compound 2 (23 mg) in 10% DCM/MeOH was added 10 mL of a 3M solution of HCl in iso-propanol. The contents were stirred overnight for 16 hrs. Concentration of the reaction mixture afforded the hydrochloride salt. $^1$HNMR (d6-DMSO) 9.01 (s, 1H), 7.94 (m, 1H), 7.86 (m, 1H), 7.23 (s, 1H), 4.30 (m, 2H), 3.64 (m, 2H), 3.36 (m, 4H), 3.25 (m, 4H). LCMS (ESI) 465 (M+H)

Compound 4

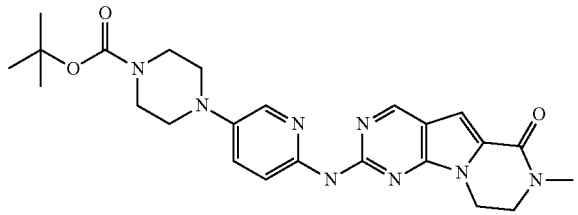

To chloro-N-methyltricyclic amide 0.080 g (0.338 mmole) in dioxane 3.5 mL under nitrogen was added tert-butyl 4-(6- amino-3-pyridyl)piperazine-1-carboxylate 0.102 g (1.1 eq) followed by the addition of Pd$_2$(dba)$_3$ (27 mg), BINAP (36 mg) and sodium-tert-butoxide (45 mg). The contents were refluxed for 11 hrs. The crude product was purified using column chromatography with an eluent of dichloromethane/methanol (0-5%) to afford the desired product (44 mg). $^1$HNMR (d6-DMSO) 9.49 (s, 1H), 8.85 (s, 1H), 8.32 (m, 1H), 8.02 (s, 1H), 7.44 (m, 1H), 7.00 (s, 1H), 4.33 (m, 2H), 3.80 (m, 2H), 3.48 (m, 4H), 3.07 (m, 4H), 3.05 (s, 3H), 1.42 (s, 9H). LCMS (ESI) 479 (M+H)

Compound 5

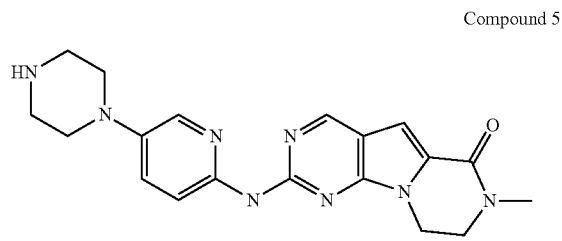 [SMILES: CN1CCn2c(cc3cnc(Nc4ccc(N5CCNCC5)cn4)nc32)C1=O]

To 32 mg of Compound 4 was added 10 mL 3N HCL in isopropanol and the contents stirred at room temperature overnight for 16 hrs. Concentration afforded the hydrochloride salt. $^1$HNMR (d6-DMSO) 9.13 (m, 2H), 8.11 (m, 1H), 8.10 (s, 1H), 7.62 (m, 1H), 7.21 (s, 1H), 4.43 (m, 2H), 3.85 (m, 2H), 3.41 (m, 4H), 3.28 (m, 4H), 3.08 (s, 3H). LCMS (ESI) 379 (M+H)

Compound 6

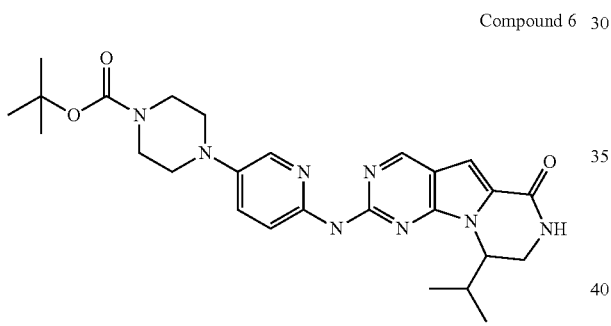

Compound 6 was synthesized using similar experimental conditions to that described for compound 2. $^1$H NMR (600 MHz, DMSO-d$_6$) δ ppm 0.79 (d, J=7.03 Hz, 3 H) 1.01 (d, J=6.73 Hz, 3 H) 1.35-1.48 (m, 9 H) 2.16 (dd, J=14.64, 6.73 Hz, 1 H) 3.00-3.14 (m, 4 H) 3.40-3.51 (m, 4 H) 3.51-3.60 (m, 1 H) 3.63-3.74 (m, 1 H) 4.44 (dd, J=7.90, 3.81 Hz, 1 H) 6.99 (s, 1 H) 7.46 (dd, J=8.93, 2.78 Hz, 1 H) 7.94-8.09 (m, 2 H) 8.31 (dd, J=9.08, 1.46 Hz, 1 H) 8.85 (s, 1 H) 9.46 (s, 1 H). LCMS (ESI) 507 (M+H).

Compound 7

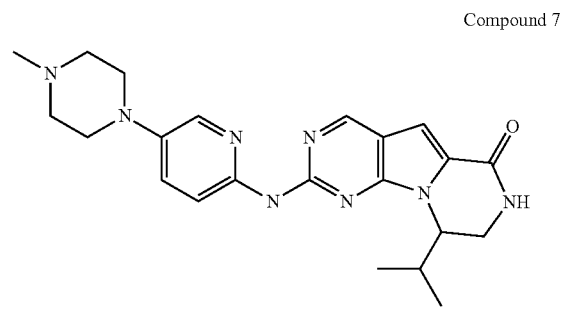 [SMILES: CC(C)C1CNC(=O)c2cc3cnc(Nc4ccc(N5CCN(C)CC5)cn4)nc3n21]

Compound 7 was synthesized using similar experimental conditions to that described for compound 1 and was recovered as an HCl salt. 1H NMR (600 MHz, DMSO-d$_6$) δ ppm 0.77-0.86 (m, 3 H) 0.96 (d, J=7.03 Hz, 3 H) 2.10-2.24 (m, 1 H) 3.07 (s, 3 H) 3.37-3.79 (m, 8 H) 4.00 (dd, J=13.61, 4.54 Hz, 2 H) 4.63-4.73 (m, 1 H) 7.20 (s, 1 H) 7.58-7.71 (m, 1 H) 7.99 (d, J=2.34 Hz, 1 H) 8.12 (d, J=9.37 Hz, 1 H) 9.11 (s, 1 H) 9.41 (br. s., 2 H) 11.76 (br. s., 1 H). LCMS (ESI) 421 (M+H).

Compound 8

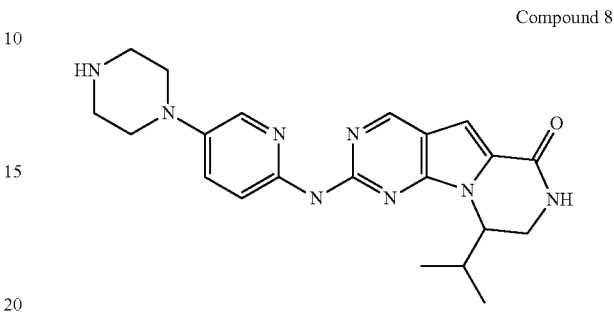

Compound 8 was synthesized using similar experimental conditions to that described for compounds 2 and 3 and was recovered as an HCl salt. The characterization data (NMR and LCMS) was consistent with that reported for compound 9.

Compound 9

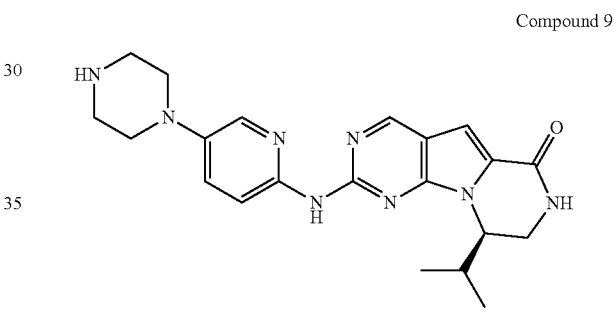

Compound 9 was synthesized using similar experimental conditions to that described for compounds 2 and 3 and was recovered as an HCl salt. 1H NMR (600 MHz, DMSO-d$_6$) δ ppm 0.79 (d, J=6.73 Hz, 3 H) 1.01 (d, J=6.73 Hz, 3 H) 2.18 (dd, J=14.49, 7.17 Hz, 1 H) 3.18-3.84 (m, 10 H) 4.53-4.71 (m, 1 H) 7.24 (s, 1 H) 7.65 (d, J=9.37 Hz, 1 H) 8.01 (d, J=2.64 Hz, 1 H) 8.14 (d, J=1.46 Hz, 1 H) 8.35 (d, J=5.27 Hz, 1 H) 9.14 (s, 1 H) 9.46 (s, 2 H) 11.80 (s, 1 H) LCMS (ESI) 407 (M+H).

Compound 10

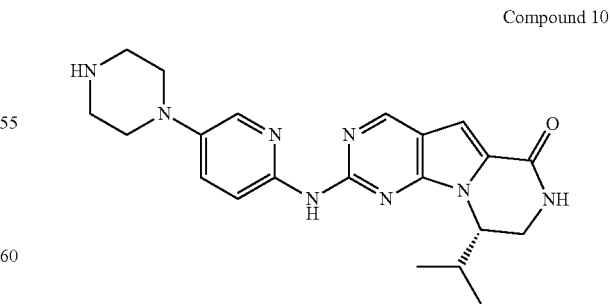

Compound 10 was synthesized using similar experimental conditions to that described for compounds 2 and 3 and was recovered as an HCl salt. 1H NMR (600 MHz, DMSO-d$_6$) δ ppm 0.77 (d, J=7.03 Hz, 3 H) 0.99 (d, J=6.73 Hz, 3 H)

2.10-2.24 (m, 1 H) 3.18-3.81 (m, 10 H) 4.54-4.69 (m, 1 H) 7.22 (s, 1 H) 7.63 (d, J=9.08 Hz, 1 H) 7.99 (d, J=2.63 Hz, 1 H) 8.11 (s, 1 H) 8.33 (d, J=5.27 Hz, 1 H) 9.12 (s, 1 H) 9.43 (s, 2 H) 11.77 (s, 1 H). LCMS (ESI) 407 (M+H).

Compound 11

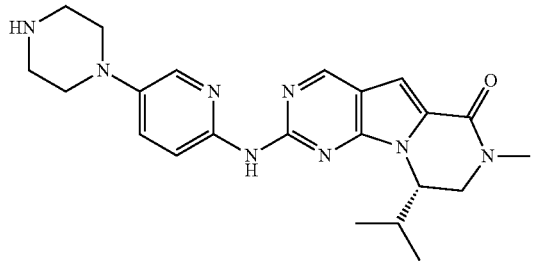

Compound 11 was synthesized using similar experimental conditions to that described for compounds 2 and 3 and was recovered as an HCl salt. 1H NMR (600 MHz, DMSO-$d_6$) δ ppm 0.84 (d, J=6.73 Hz, 3 H) 0.98 (d, J=6.73 Hz, 3 H) 2.12-2.26 (m, 1 H) 3.09 (s, 3 H) 3.22-3.81 (m, 8 H) 4.01 (dd, J=13.61, 4.25 Hz, 2 H) 4.59-4.72 (m, 1 H) 7.19 (s, 1 H) 7.74 (s, 1 H) 7.96-8.10 (m, 2 H) 9.08 (s, 1 H) 9.22 (s, 2 H). LCMS (ESI) 421 (M+H).

Compound 12

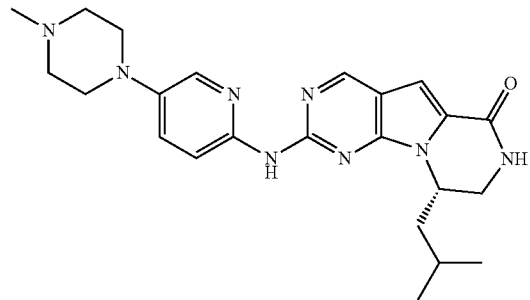

Compound 12 was synthesized using similar experimental conditions to that described for compound 1 and was recovered as an HCl salt. 1H NMR (600 MHz, DMSO-$d_6$) δ ppm 0.85 (d, J=4.98 Hz, 3 H) 0.95 (d, J=4.98 Hz, 3 H) 1.42-1.70 (m, 3 H) 2.77 (d, J=2.93 Hz, 3 H) 3.07-4.14 (m, 10 H) 4.95 (s, 1 H) 7.20 (s, 1 H) 7.66 (d, J=9.66 Hz, 1 H) 7.94 (s, 1 H) 8.08-8.16 (m, 1 H) 8.33 (d, J=4.68 Hz, 1 H) 9.09 (s, 1 H) 11.38 (s, 1 H) 11.71 (s, 1 H). LCMS (ESI) 435 (M+H).

Compound 13

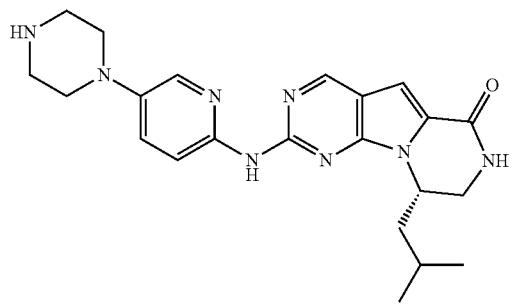

Compound 13 was synthesized using similar experimental conditions to that described for compounds 2 and 3 and was recovered as an HCl salt. 1H NMR (600 MHz, DMSO-$d_6$) δ ppm 0.87 (d, J=6.15 Hz, 3 H) 0.94 (d, J=6.15 Hz, 3 H) 1.57 (d, J=84.61 Hz, 3 H) 3.05 (s, 3 H) 3.13-3.55 (m, 8 H) 3.69 (d, J=78.17 Hz, 2 H) 4.90 (s, 1 H) 7.15 (s, 1 H) 7.63-7.85 (m, 1 H) 7.93 (s, 1 H) 8.26 (s, 1 H) 9.03 (s, 1 H) 9.20 (s, 2 H). LCMS (ESI) 421 (M+H).

Compound 14

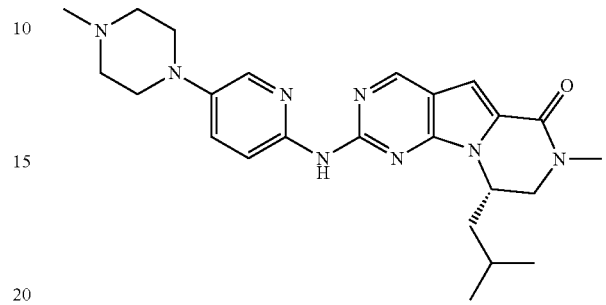

Compound 14 was synthesized using similar experimental conditions to that described for compound 1 and was recovered as an HCl salt. 1H NMR (600 MHz, DMSO-$d_6$) δ ppm 0.85 (d, J=6.44 Hz, 3 H) 0.95 (d, J=6.44 Hz, 3 H) 1.43-1.70 (m, 3 H) 2.78 (d, J=2.93 Hz, 3 H) 3.05 (s, 3 H) 3.24-3.84 (m, 8 H) 4.01 (d, J=9.66 Hz, 2 H) 4.89-5.01 (m, 1 H) 7.15 (s, 1 H) 7.77 (s, 1 H) 7.91-8.05 (m, 2 H) 9.03 (s, 1 H) 10.96-11.55 (m, 2 H). LCMS (ESI) 449 (M+H).

Compound 15

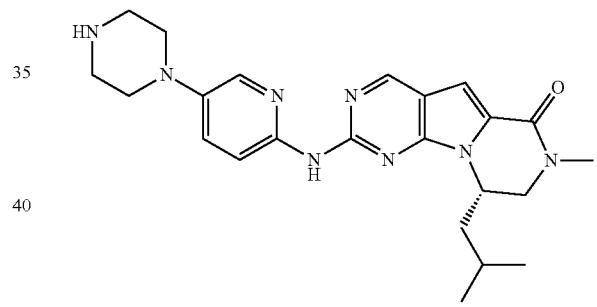

Compound 15 was synthesized using similar experimental conditions to that described for compounds 2 and 3 and was recovered as an HCl salt. 1H NMR (600 MHz, DMSO-$d_6$) δ ppm 0.83-0.88 (d, J=6.15 Hz, 3 H) 0.95 (d, J=6.15 Hz, 3 H) 1.40-1.71 (m, 3 H) 3.28-3.83 (m, 8 H) 4.00 (d, J=3.22 Hz, 2 H) 4.91-5.08 (m, 1 H) 7.17 (s, 1 H) 7.68 (d, J=9.66 Hz, 1 H) 7.93 (s, 1 H) 8.07 (s, 1 H) 9.06 (s, 1 H) 9.40 (s, 2 H) 11.59 (s, 1 H). LCMS (ESI) 435 (M+H).

Compound 16

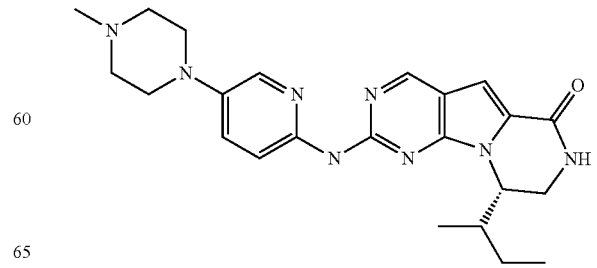

To intermediate 1E 0.060 g (0.205 mmole) was added 5-(4-methylpiperazin-1-yl)pyridin-2-amine 35.42 mg (0.9 eq) followed by the addition of 1,4-dioxane (3 mL). After degassing with nitrogen, Pd₂dba₃ (12 mg), BINAP (16 mg) and sodium tert-butoxide (24 mg) were added. The contents were then heated at 90 degrees in a CEM Discovery microwave for 3 hrs. The reaction is then loaded over a silica gel column and purified by eluting with DCM/MeOH (0-15%) to afford compound 16. 1H NMR (600 MHz, DMSO-d₆) δ ppm 0.75 (t, J=7.47 Hz, 3 H) 0.91 (d, J=6.73 Hz, 3 H) 1.04-1.20 (m, 2 H) 1.80-1.98 (m, 1 H) 2.77 (d, J=3.81 Hz, 3 H) 2.94-3.90 (m, 10 H) 4.54-4.68 (m, 1 H) 7.06-7.23 (m, 2 H) 7.56-7.75 (m, 1 H) 7.90-8.12 (m, 2 H) 8.29 (s, 1 H) 9.07 (s, 1 H) 10.98-11.74 (m, 2 H). LCMS (ESI) 435 (M+H).

Compound 17

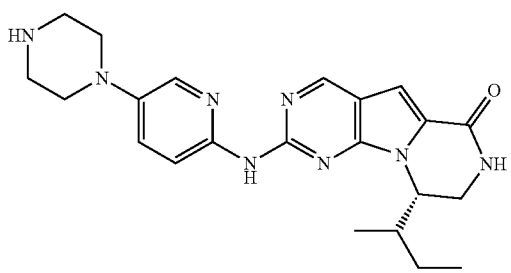

Compound 17 was synthesized in a similar manner to that described for compound 16 followed by the deblocking step described for compound 3 and was converted to an HCl salt. 1H NMR (600 MHz, DMSO-d₆) δ ppm 0.75 (t, J=7.32 Hz, 3 H) 0.90 (d, J=6.73 Hz, 3 H) 1.07-1.15 (m, 2 H) 1.85-1.94 (m, 1 H) 3.17-3.75 (m, 10 H) 4.58-4.67 (m, 1 H) 7.17 (s, 1 H) 7.71 (s, 1 H) 7.96 (s, 1 H) 7.98-8.05 (m, 1 H) 8.28 (d, J=4.10 Hz, 1 H) 9.06 (s, 1 H) 9.39 (s, 2 H). LCMS (ESI) 421 (M+H).

Compound 18

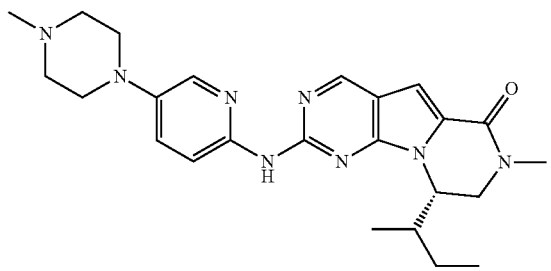

Compound 18 was synthesized in a similar manner to that described for compound 16. 1H NMR (600 MHz, DMSO-d₆) δ ppm 0.78 (t, J=7.32 Hz, 3 H) 0.86 (d, J=6.73 Hz, 3 H) 1.13-1.21 (m, 2 H) 1.84-1.96 (m, 1 H) 2.77 (d, J=4.39 Hz, 3 H) 3.04 (s, 3 H) 3.11-3.84 (m, 8 H) 3.98 (dd, J=13.61, 4.25 Hz, 2 H) 4.66-4.74 (m, 1 H) 7.17 (s, 1 H) 7.64 (s, 1 H) 7.96 (d, J=2.34 Hz, 1 H) 8.03-8.13 (m, 1 H) 9.08 (s, 1 H) 11.26 (s, 1 H) 11.66 (s, 1 H). LCMS (ESI) 449 (M+H).

Compound 19

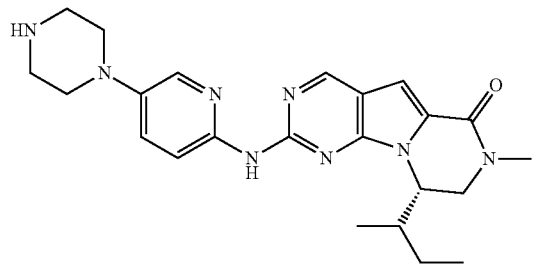

Compound 19 was synthesized in a similar manner to that described for compound 16 followed by the deblocking step described for compound 3 and was converted to an HCl salt. 1H NMR (600 MHz, DMSO-d₆) δ ppm 0.78 (t, J=7.32 Hz, 3 H) 0.85 (d, J=6.73 Hz, 3 H) 1.10-1.27 (m, 2 H) 1.82-1.99 (m, 1 H) 3.04 (s, 3 H) 3.28-3.77 (m, 8 H) 3.97 (dd, J=13.91, 4.54 Hz, 2 H) 4.62-4.75 (m, 1 H) 7.07-7.24 (m, 1 H) 7.62-7.75 (m, 1 H) 7.94 (d, J=2.34 Hz, 1 H) 7.97-8.08 (m, 1 H) 9.05 (s, 1 H) 9.29 (s, 2 H). LCMS (ESI) 435 (M+H).

Compound 20

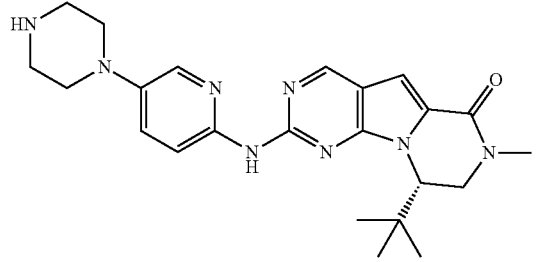

Compound 20 was synthesized in a similar manner to that described for compound 16 followed by the deblocking step described for compound 3 and was converted to an HCl salt. 1H NMR (600 MHz, DMSO-d₆) δ ppm 0.96 (s, 9 H) 3.15-3.87 (m, 10 H) 4.42-4.53 (m, 1 H) 6.99 (s, 1 H) 7.24 (s, 1 H) 8.06 (s, 1 H) 8.11-8.21 (m, 1 H) 8.79-8.98 (m, 2 H) 9.25 (s, 2 H) 9.88 (s, 1 H). LCMS (ESI) 421 (M+H).

Compound 21

Compound 21 was synthesized in a similar manner to that described for compound 16 followed by the deblocking step described for compound 3 and was converted to an HCl salt. 1H NMR (600 MHz, DMSO-d₆) δ ppm 0.95 (s, 9 H) 2.79 (d, J=4.10 Hz, 3 H) 3.06-3.86 (m, 10 H) 4.56-4.67 (m, 1 H) 7.17 (s, 1 H) 7.70 (s, 1 H) 7.96 (d, J=2.63 Hz, 1 H) 7.99-8.08 (m, 1 H) 8.26 (s, 1 H) 9.06 (s, 1 H) 10.80 (s, 1 H). LCMS (ESI) 435 (M+H).

Compound 22

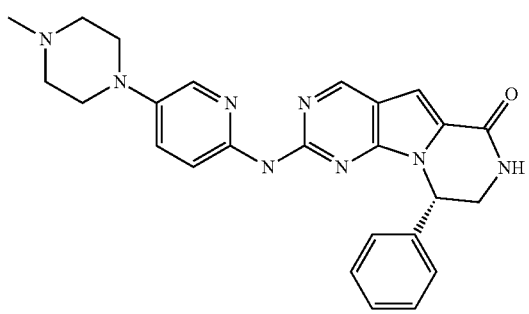

Compound 22 was synthesized in a similar manner to that described for compound 16 and was converted to an HCl salt. 1H NMR (600 MHz, DMSO-d$_6$) δ ppm 2.75-2.81 (m, 3 H) 3.12-3.16 (m, 2 H) 3.46-3.54 (m, 4 H) 3.60-3.69 (m, 2 H) 3.72-3.79 (m, 1 H) 4.07-4.18 (m, 2 H) 6.06-6.09 (m, 1 H) 6.90 (d, J=7.61 Hz, 2 H) 7.20-7.31 (m, 3 H) 7.33 (s, 1 H) 7.49-7.55 (m, 1 H) 7.62-7.70 (m, 1 H) 7.92 (d, J=2.93 Hz, 1 H) 8.22 (s, 1 H) 9.14 (s, 1 H). LCMS (ESI) 455 (M+H).

Compound 23

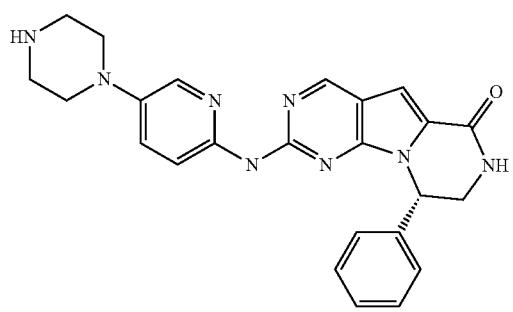

Compound 23 was synthesized in a similar manner to that described for compound 16 followed by the deblocking step described for compound 3 and was converted to an HCl salt. 1H NMR (600 MHz, DMSO-d$_6$) δ ppm 3.21 (s, 4 H) 3.35-3.67 (m, 5 H) 4.07-4.20 (m, 2 H) 6.13 (s, 1 H) 6.90 (d, J=7.32 Hz, 2 H) 7.22-7.31 (m, 3 H) 7.36 (s, 1 H) 7.48 (d, J=9.37 Hz, 1 H) 7.93 (d, J=2.34 Hz, 1 H) 8.04-8.11 (m, 1 H) 8.25 (d, J=4.98 Hz, 1 H) 9.17 (s, 1 H) 11.77 (br, s., 1H). LCMS (ESI) 441 (M+H).

Compound 24

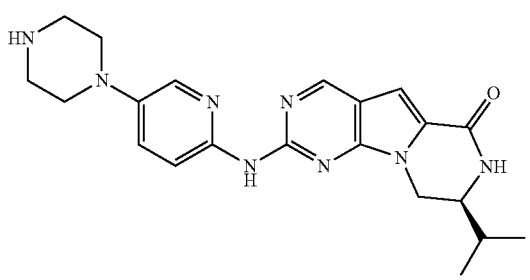

Compound 24 was synthesized in a similar manner to that described for compound 16 followed by the deblocking step described for compound 3 and was converted to an HCl salt. 1H NMR (600 MHz, DMSO-d$_6$) δ ppm 0.90 (d, J=6.15 Hz, 6 H) 1.72-1.89 (m, 1 H) 3.15-3.92 (m, 9 H) 4.10-4.46 (m, 2 H) 7.18 (s, 1 H) 7.59 (d, J=8.78 Hz, 1 H) 8.00 (s, 1 H) 8.13 (d, J=9.37 Hz, 1 H) 8.55 (s, 1 H) 9.09 (s, 1 H) 9.67 (s, 2 H) 11.91 (s, 1 H). LCMS (ESI) 407 (ESI).

Compound 25

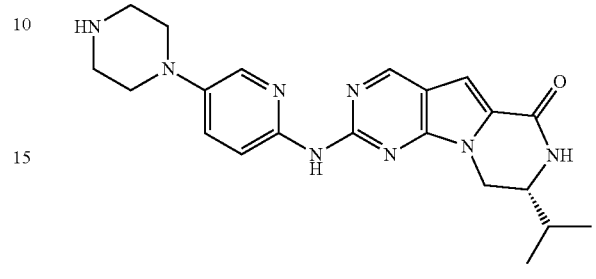

Compound 25 was synthesized in a manner similar to compound 24 and was converted to an HCl salt. The characterization data (NMR and LCMS) was similar to that obtained for the antipode compound 24.

Compound 26

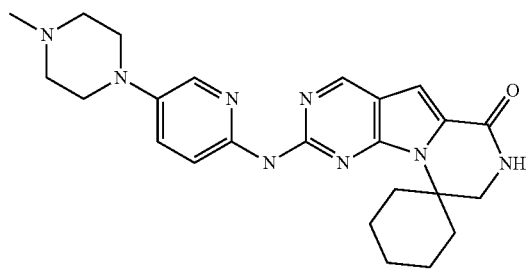

Compound 26 was synthesized in a similar manner to that described for compound 16 followed by the deblocking step described for compound 3 and was converted to an HCl salt. 1H NMR (600 MHz, DMSO-d$_6$) δ ppm 1.78 (s, 6 H) 3.40-3.53 (m, 6 H) 3.64-3.73 (m, 4 H) 7.27 (s, 1 H) 7.66 (d, J=9.37 Hz, 1 H) 7.98 (d, J=2.34 Hz, 1 H) 8.12 (br. s., 1 H) 8.47 (br. s., 1 H) 9.11 (s, 1 H) 9.45 (br. s., 2 H) 11.62 (br. s., 1 H). LCMS (ESI) 393 (M+H).

Compound 27

Compound 27 was synthesized in a similar manner to that described for compound 16 and was converted to an HCl salt. 1H NMR (600 MHz, DMSO-d$_6$) δ ppm 1.47 (br. s., 6 H) 1.72 (br. s., 2 H) 1.92 (br. s., 2 H) 2.77 (br. s., 3 H) 3.18 (br. s., 2 H) 3.46 (br. s., 2 H) 3.63 (br. s., 2 H) 3.66 (d, J=6.15 Hz, 2 H) 3.80

(br. s., 2 H) 7.25 (s, 1 H) 7.63 (br. s., 2 H) 7.94 (br. s., 1 H) 8.10 (br. s., 1 H) 8.39 (br. s., 1 H) 9.08 (br. s., 1 H) 11.59 (br. s., 1 H). LCMS (ESI) 447 (M+H).

Compound 28

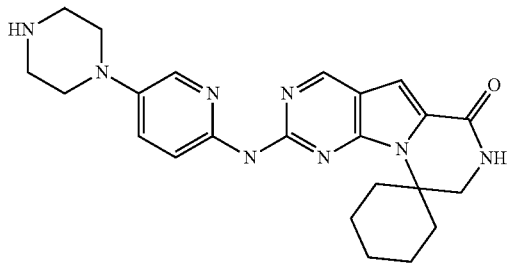

Compound 28 was synthesized in a similar manner to that described for compound 16 followed by the deblocking step described for compound 3 and was converted to an HCl salt. 1H NMR (600 MHz, DMSO-$d_6$) δ ppm 1.27-1.64 (m, 6 H) 1.71 (br. s., 2 H) 1.91 (br. s., 2 H) 2.80 (br. s., 1 H) 3.17-3.24 (m, 2 H) 3.41 (br. s., 4 H) 3.65 (br. s., 4 H) 7.26 (br. s., 1 H) 7.63 (br. s., 1 H) 7.94 (br. s., 1 H) 8.13 (br. s., 1 H) 8.40 (br. s., 1 H) 9.09 (br. s., 1 H) 9.62 (br. s., 1 H) 11.71 (br. s., 1 H). LCMS (ESI) 433 (M+H).

Compound 29

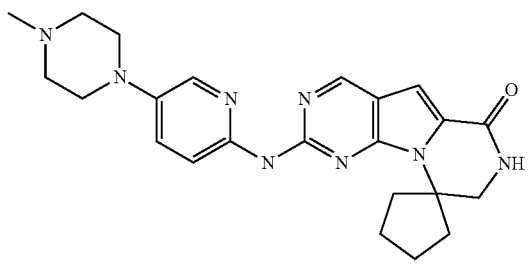

Compound 29 was synthesized using similar conditions to that described for compound 16 and was converted to an HCl salt. 1H NMR (600 MHz, DMSO-$d_6$) δ ppm 1.64-1.75 (m, 2 H) 1.83-1.92 (m, 2 H) 1.96-2.06 (m, 2 H) 2.49-2.58 (m, 2 H) 2.79 (d, J=3.81 Hz, 3 H) 3.06-3.18 (m, 4 H) 3.59-3.69 (m, 2 H) 3.73-3.83 (m, 2 H) 4.04-4.12 (m, 2 H) 7.17 (br. s., 1 H) 7.60-7.70 (m, 2 H) 7.70-7.92 (m, 2 H) 7.96 (br. s., 1 H) 8.41 (br. s., 1 H) 8.98 (br. s., 1 H) 10.77 (br. s., 1 H). LCMS (ESI) 433 (M+H).

Compound 30

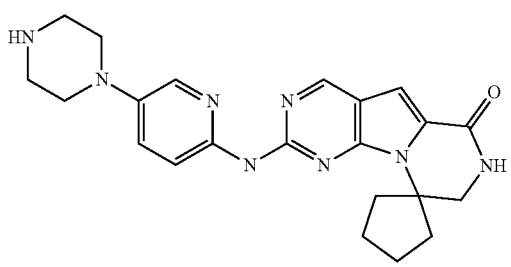

Compound 30 was synthesized in a similar manner to that described for compound 16 followed by the deblocking step described for compound 3 and was converted to an HCl salt. 1H NMR (600 MHz, DMSO-$d_6$) δ ppm 1.64-1.75 (m, 2 H) 1.84-1.92 (m, 2 H) 1.96-2.05 (m, 2 H) 2.48-2.56 (m, 2 H) 3.22 (br. s., 4 H) 3.42-3.48 (m, 4 H) 3.60-3.69 (m, 2 H) 4.05-4.13 (m, 1 H) 7.18 (s, 1 H) 7.65 (d, J=13.47 Hz, 1 H) 7.70-7.77 (m, 1 H) 7.94 (d, J=1.76 Hz, 1 H) 8.42 (br. s., 1 H) 9.00 (s, 1 H) 9.15 (br. s., 2 H). LCMS (ESI) 419 (M+H).

Compound 31

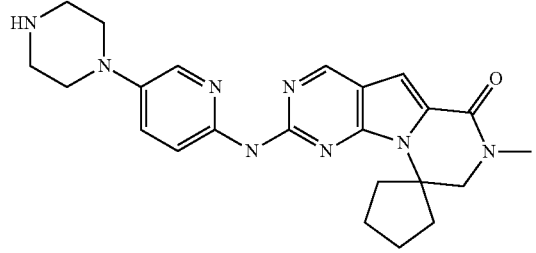

Compound 31 was synthesized in a similar manner to that described for compound 16 followed by the deblocking step described for compound 3 and was converted to an HCl salt. 1H NMR (600 MHz, DMSO-$d_6$) δ ppm 1.76 (br. s., 2 H) 1.89 (br. s., 2 H) 2.03 (br. s., 2 H) 2.47-2.58 (m, 2 H) 3.04 (s, 3 H) 3.22 (br. s., 4 H) 3.39 (br. s., 4 H) 3.66 (s, 2 H) 7.21 (s, 1 H) 7.67 (d, J=9.37 Hz, 1 H) 7.93 (br. s., 1 H) 7.98-8.09 (m, 1 H) 9.04 (s, 1 H) 9.34 (br. s., 2 H) 11.31 (br. s., 1 H). LCMS (ESI) 433 (M+H).

Compound 32

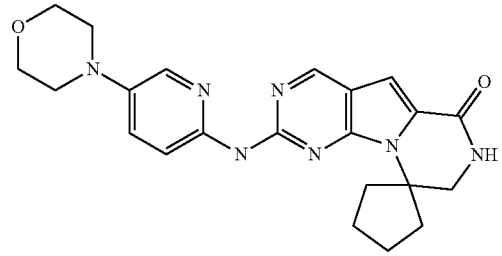

Compound 32 was synthesized using similar conditions to that described for compound 16 and was converted to an HCl salt. 1H NMR (600 MHz, DMSO-$d_6$) δ ppm 1.66-1.77 (m, 2 H) 1.84-1.94 (m, 2 H) 1.96-2.08 (m, 2 H) 2.48-2.57 (m, 2 H) 3.36-3.52 (m, 4 H) 3.60-3.80 (m, 6 H) 7.21 (s, 1 H) 7.53-7.74 (m, 2 H) 7.86 (s, 1 H) 8.02 (s, 1 H) 8.45 (s, 1 H) 9.03 (s, 1 H) 11.19 (br. s., 1 H). LCMS (ESI) 420 (M+H).

Compound 33

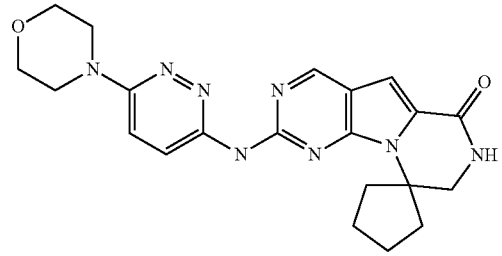

Compound 33 was synthesized using similar conditions to that described for compound 16 and was converted to an HCl salt. 1H NMR (600 MHz, DMSO-$d_6$) δ ppm 1.65-1.79 (m, 2 H) 1.85-1.95 (m, 2 H) 1.97-2.08 (m, 2 H) 2.47-2.54 (m, 2 H) 3.40-3.58 (m, 5 H) 3.65 (dd, J=21.67, 5.56 Hz, 1 H) 3.69-3.78 (m, 4 H) 7.24 (s, 1 H) 7.97-8.17 (m, 2 H) 8.48 (s, 1 H) 9.08 (s, 1 H) 11.81 (s, 1 H). LCMS (ESI) 421 (M+H).

Compound 36 was synthesized using similar conditions to that described for compound 16 and was converted to an HCl salt. 1H NMR (600 MHz, DMSO-$d_6$) δ ppm 0.99 (d, J=6.15 Hz, 6 H) 1.65-1.78 (m, 2 H) 1.90 (m, 2 H) 1.97-2.08 (m, 2 H) 2.08-2.17 (m, 1 H) 2.45-2.55 (m, 2 H) 2.88-3.02 (m, 2 H) 3.33-3.48 (m, 4 H) 3.50-3.90 (m, 6 H) 7.24 (s, 1 H) 7.67 (s, 2 H) 7.94 (s, 1 H) 8.12 (s, 1 H) 8.49 (s, 1 H) 9.07 (s, 1 H) 10.77 (s, 1 H) 11.51 (s, 1 H). LCMS (ESI) 475 (M+H).

Compound 34

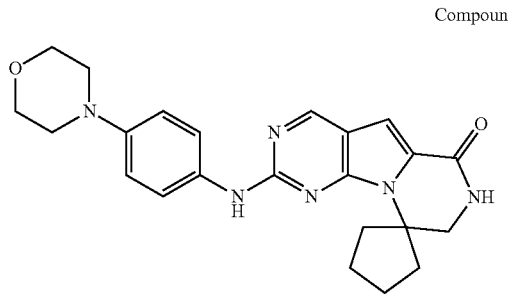

Compound 34 was synthesized using similar conditions to that described for compound 16 and was converted to an HCl salt. 1H NMR (600 MHz, DMSO-$d_6$) δ ppm 1.55-1.74 (m, 2 H) 1.80-1.98 (m, 4 H) 2.48-2.60 (m, 2 H) 3.40-3.50 (m, 4 H) 3.57-3.72 (m, 2 H) 3.90-4.20 (m, 4 H) 7.08 (s, 1 H) 7.37-7.57 (m, 2 H) 7.70 (m, 2 H) 8.32 (s, 1 H) 8.88 (s, 1 H) 9.98 (s, 1 H). LCMS (ESI) 419 (M+H).

Compound 37

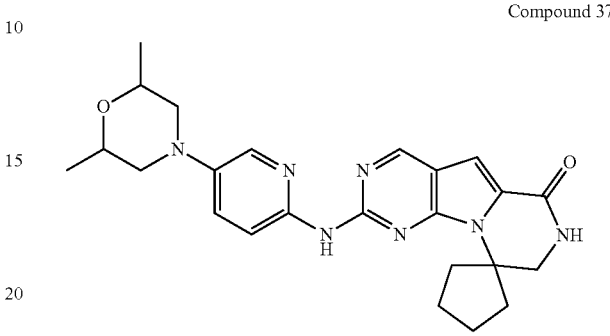

Compound 37 was synthesized using similar conditions to that described for compound 16 and was converted to an HCl salt. 1H NMR (600 MHz, DMSO-$d_6$) δ ppm 1.13 (d, J=5.86 Hz, 6 H) 1.66-1.77 (m, 2 H) 1.84-1.94 (m, 2 H) 1.97-2.09 (m, 2 H) 2.40-2.53 (m, 2 H) 3.37-3.49 (m, 2 H) 3.50-3.59 (m, 2 H) 3.59-3.73 (m, 4 H) 7.23 (s, 1 H) 7.64 (m, 3 H) 7.85 (s, 1 H) 8.11 (s, 1 H) 8.47 (s, 1 H) 9.05 (s, 1 H). 11.35 (br s., 1H). LCMS (ESI) 448 (M+H).

Compound 35

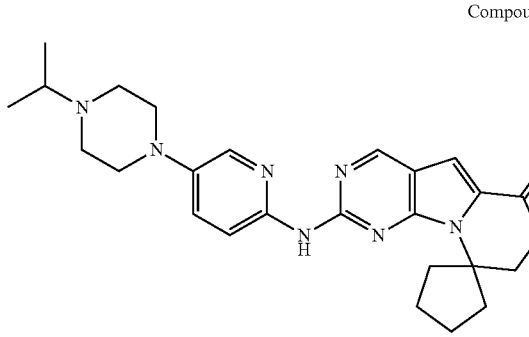

Compound 35 was synthesized using similar conditions to that described for compound 16 and was converted to an HCl salt. 1H NMR (600 MHz, DMSO-$d_6$) δ ppm 1.30 (d, J=5.27 Hz, 6 H) 1.65-1.78 (m, 2 H) 1.83-1.95 (m, 2 H) 1.97-2.10 (m, 2 H) 2.45-2.55 (m, 2H) 3.25-3.36 (m, 1 H) 3.39-3.48 (m, 4 H) 3.60-3.70 (m, 4 H) 3.75-4.15 (m, 2 H) 7.24 (s, 1 H) 7.54-7.75 (m, 2 H) 7.95 (s, 1 H) 8.10 (s, 1 H) 8.49 (s, 1 H) 9.07 (s, 1 H) 11.25 (s, 1 H) 11.48 (s, 1 H). LCMS (ESI) 461 (M+H).

Compound 38

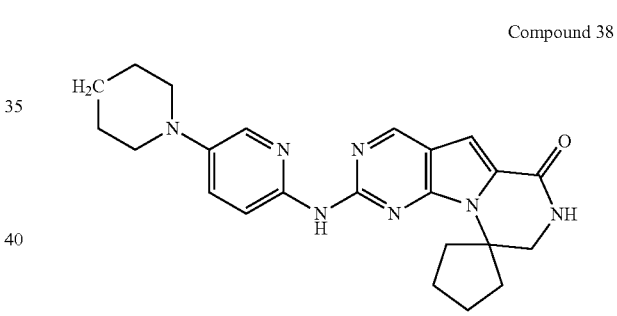

Compound 38 was synthesized using similar conditions to that described for compound 16 and was converted to an HCl salt. 1H NMR (600 MHz, DMSO-$d_6$) δ ppm 1.50-1.57 (m, 2 H) 1.62-1.68 (m, 3 H) 1.68-1.75 (m, 2 H) 1.84-1.92 (m, 2 H) 1.97-2.08 (m, 2 H) 2.48-2.53 (m, 2 H) 3.14-3.23 (m, 4 H) 3.43-3.47 (m, 2 H) 3.58-3.70 (m, 2 H) 7.22 (s, 1 H) 7.58-7.70 (m, 2 H) 7.85-8.00 (m, 1 H) 8.16 (d, 1 H) 8.46 (s, 1 H) 9.04 (s, 1 H) 11.37 (br s., 1H). LCMS (ESI) 418 (M+H).

Compound 36

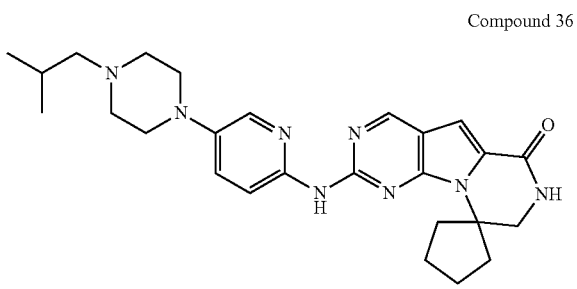

Compound 39

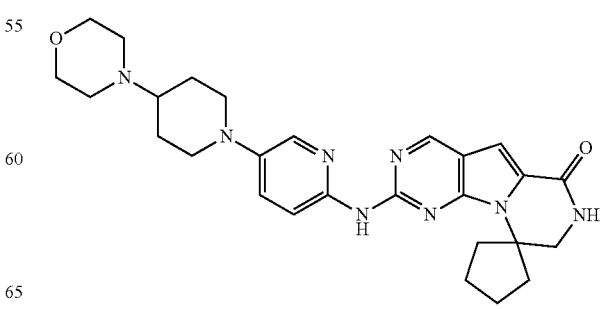

Compound 39 was synthesized using similar conditions to that described for compound 16 and was converted to an HCl salt. 1H NMR (600 MHz, DMSO-$d_6$) δ ppm 1.72 (s, 2 H) 1.90 (s, 4 H) 2.03 (s, 2 H) 2.21 (s, 2 H) 2.48-2.54 (m, 2 H) 2.73 (s, 2 H) 3.03 (s, 2 H) 3.25-3.35 (m, 1 H) 3.38-3.48 (m, 4 H) 3.65-3.99 (m, 5 H) 7.23 (s, 1 H) 7.63 (d, J=9.66 Hz, 1 H) 7.90 (s, 1 H) 8.13 (s, 1 H) 8.47 (s, 1 H) 9.06 (s, 1 H) 10.50 (br s., 1H). LCMS (ESI) 503 (M+H).

Compound 40

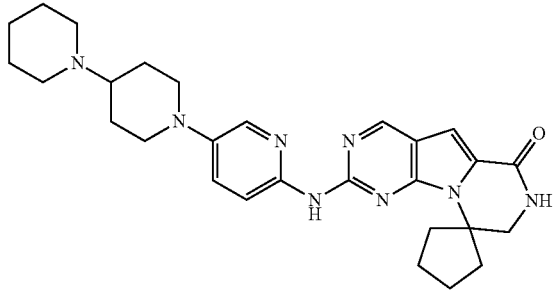

Compound 40 was synthesized using similar conditions to that described for compound 16 and was converted to an HCl salt. 1H NMR (600 MHz, DMSO-$d_6$) δ ppm 1.63-1.85 (m, 6 H) 1.87-1.92 (m, 2 H) 1.99-2.06 (m, 2 H) 2.15-2.23 (m, 2 H) 2.47-2.53 (m, 1 H) 2.69-2.79 (m, 2 H) 2.81-2.91 (m, 2 H) 2.98-3.08 (m, 2 H) 3.32-3.48 (m, 4 H) 3.57-3.72 (m, 4 H) 3.77-3.85 (m, 2 H) 7.22 (s, 1 H) 7.60-7.68 (m, 2 H) 7.90 (s, 1 H) 8.07 (s, 1 H) 8.46 (s, 1 H) 9.04 (s, 1 H). 11.41 (br s., 1H). LCMS (ESI) 501 (M+H).

Compound 41

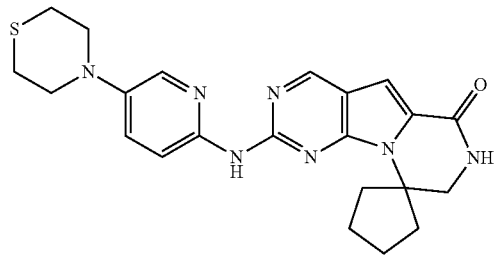

Compound 41 was synthesized using similar conditions to that described for compound 16 and was converted to an HCl salt. 1H NMR (600 MHz, DMSO-$d_6$) δ ppm 1.64-1.76 (m, 2 H) 1.87-1.93 (m, 2 H) 2.00-2.07 (m, 2 H) 2.48-2.53 (m, 2 H) 2.67-2.72 (m, 4 H) 3.44-3.47 (m, 2 H) 3.50-3.55 (m, 4 H) 7.24 (s, 1 H) 7.61 (d, J=9.37 Hz, 2 H) 7.86 (d, J=2.63 Hz, 1 H) 8.09 (d, J=12.88 Hz, 1 H) 8.48 (s, 1 H) 9.06 (s, 1 H) 11.41 (br s., 1H). LCMS (ESI) 436 (M+H).

Compound 42

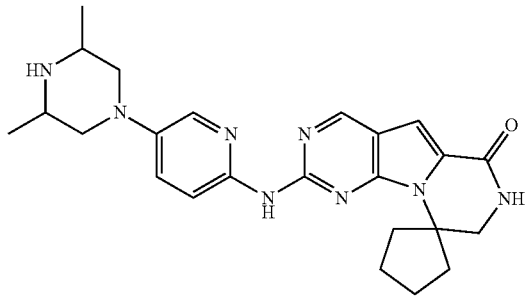

Compound 42 was synthesized using similar conditions to that described for compound 16 and was converted to an HCl salt. 1H NMR (600 MHz, DMSO-$d_6$) δ ppm 1.29 (d, J=6.73 Hz, 6 H) 1.66-1.79 (m, 2 H) 1.84-1.95 (m, 2 H) 1.98-2.09 (m, 2 H) 2.46-2.55 (m, 2 H) 3.29-3.39 (m, 2H) 3.58-3.70 (m, 4H) 3.77-3.86 (m, 4H) 7.24 (s, 1 H) 7.66 (d, J=9.37 Hz, 1 H) 7.96 (d, J=2.93 Hz, 1 H) 8.08 (s, 1 H) 8.48 (s, 1 H) 9.06 (s, 1 H) 9.28 (s, 1 H) 9.67 (s, 1 H) 11.36 (s, 1 H). LCMS (ESI) 447 (M+H).

Compound 43

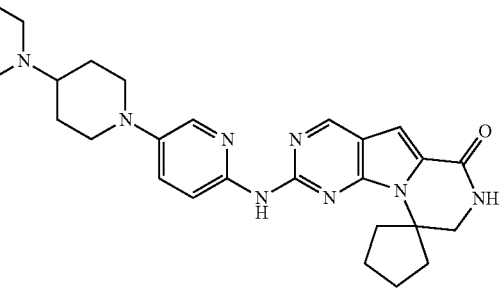

Compound 43 was synthesized using similar conditions to that described for compound 16 and was converted to an HCl salt. 1H NMR (600 MHz, DMSO-$d_6$) δ ppm 1.73 (s, 2 H) 1.76-1.85 (m, 2 H) 1.85-1.94 (m, 2 H) 1.98-2.07 (m, 2 H) 2.19-2.26 (m, 2 H) 2.48-2.52 (m, 1 H) 2.70-2.81 (m, 4 H) 3.13-3.20 (m, 1 H) 3.30-3.48 (m, 3 H) 3.58-3.71 (m, 4 H) 3.78-3.84 (m, 4 H) 7.24 (s, 1 H) 7.62 (d, J=9.37 Hz, 2 H) 7.89 (d, J=1.17 Hz, 1 H) 8.09-8.18 (m, 1 H) 8.48 (s, 1 H) 9.06 (s, 1 H) 11.46 (br s., 1H). LCMS (ESI) 519 (M+H).

Compound 44

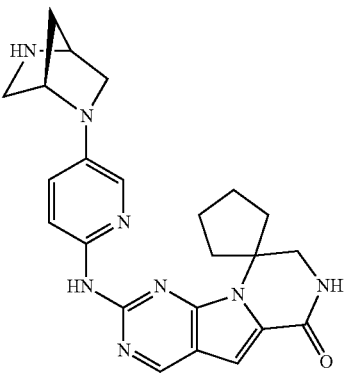

Compound 44 was synthesized using similar conditions to that described for compound 16 followed by the deblocking step described for compound 3 and was converted to an HCl salt. 1H NMR (600 MHz, DMSO-$d_6$) δ ppm 1.65-1.75 (m, 2 H) 1.85-1.93 (m, 2 H) 1.93-1.99 (m, 1 H) 2.00-2.06 (m, 2 H) 2.08-2.14 (m, 1 H) 2.47-2.55 (m, 2 H) 3.07-3.25 (m, 2 H) 3.25-3.69 (m, 5 H) 4.46 (s, 1 H) 4.67 (s, 1 H) 7.22 (s, 1 H) 7.58-7.69 (m, 2 H) 8.46 (s, 1 H) 9.02 (s, 1 H) 9.34 (s, 1 H) 9.65 (s, 1 H). LCMS (ESI) 431 (M+H).

Compound 45

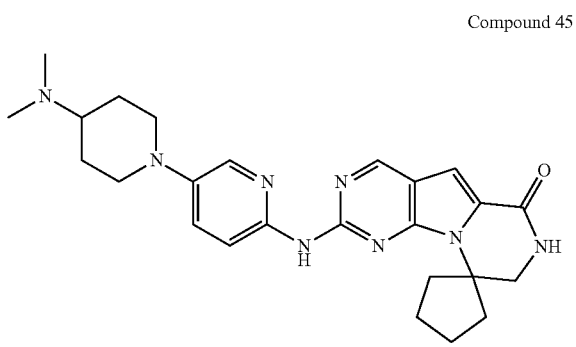 [SMILES: CC(C)N1CCN(c2ccc(Nc3ncc4cc5n(c4n3)C3(CCCC3)CNC5=O)nc2)CC1]

Compound 45 was synthesized using similar conditions to that described for compound 16 and was converted to an HCl salt. 1H NMR (600 MHz, DMSO-$d_6$) δ ppm 1.65-1.82 (m, 3 H) 1.89 (br. s., 2 H) 1.98-2.08 (m, 2 H) 2.13 (br. s., 2 H) 2.47-2.55 (m, 2 H) 2.68 (d, J=4.98 Hz, 6 H) 2.71-2.80 (m, 2 H) 3.29-3.71 (m, 10 H) 7.16-7.26 (m, 1 H) 7.67 (d, J=9.66 Hz, 2 H) 7.91 (d, J=2.05 Hz, 1 H) 8.14 (br. s., 1 H) 8.48 (br. s., 1 H) 9.05 (s, 1 H) 11.14 (br. s., 1 H) 11.43 (br. s., 1 H). LCMS (ESI) 461 (M+H).

Compound 46

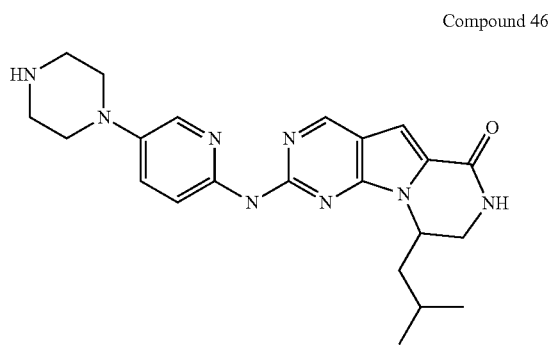 [SMILES: CC(C)CC1CNC(=O)c2cc3cnc(Nc4ccc(N5CCNCC5)cn4)nc3n21]

Compound 46 was synthesized in a manner similar to that described for compounds 2 and 3 and was recovered as an HCl salt. The analytical data was consistent with that described for the antipode compound 13.

Compound 47

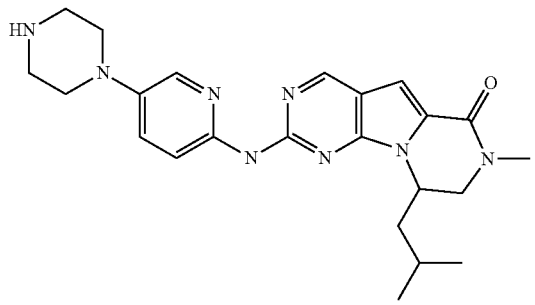

Compound 47 was synthesized in a manner similar to that described for compounds 2 and 3 and was recovered as an HCl salt. The analytical data was consistent with that described for the antipode compound 15.

Compound 48

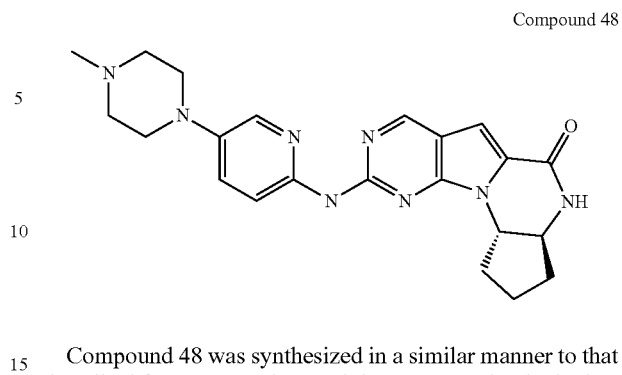

Compound 48 was synthesized in a similar manner to that described for compound 16 and then converted to its hydrochloride salt. 1H NMR (600 MHz, DMSO-$d_6$) δ ppm 1.50-1.65 (m, 1 H) 1.92-2.02 (m, 3 H) 2.06-2.15 (m, 1 H) 2.78 (d, J=3.81 Hz, 4 H) 3.10-3.20 (m, 4 H) 3.47-3.51 (m, 2 H) 3.64-3.71 (m, 1 H) 3.76-3.83 (m, 2 H) 3.98-4.14 (m, 1 H) 7.20 (s, 2 H) 7.77 (s, 1 H) 7.97 (s, 2 H) 8.81 (s, 1 H) 9.03 (s, 1 H) 10.97 (br s., 1H). LCMS (ESI) 419 (M+H).

Compound 49

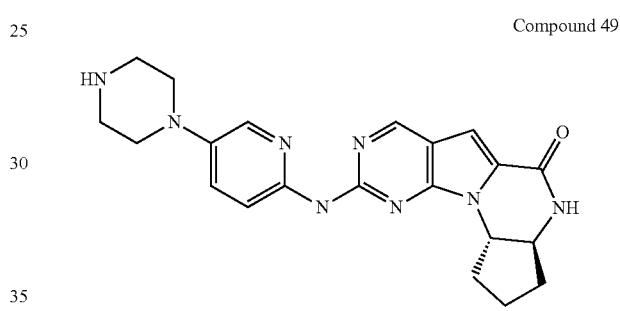

Compound 49 was synthesized in a similar manner to that described for compound 16 and then converted to its hydrochloride salt. 1H NMR (600 MHz, DMSO-$d_6$) δ ppm 1.54-1.59 (m, 1 H) 1.92-2.01 (m, 3 H) 2.06-2.15 (m, 1 H) 2.76-2.84 (m, 1 H) 3.17-3.24 (m, 6 H) 3.64-3.71 (m, 2 H) 4.02-4.11 (m, 2 H) 7.22 (s, 2 H) 7.64 (s, 1 H) 7.97 (s, 2 H) 8.75 (s, 1 H) 8.97 (s, 1 H) 9.21 (s, 1 H). LCMS (ESI) 405 (M+H).

Compound 50

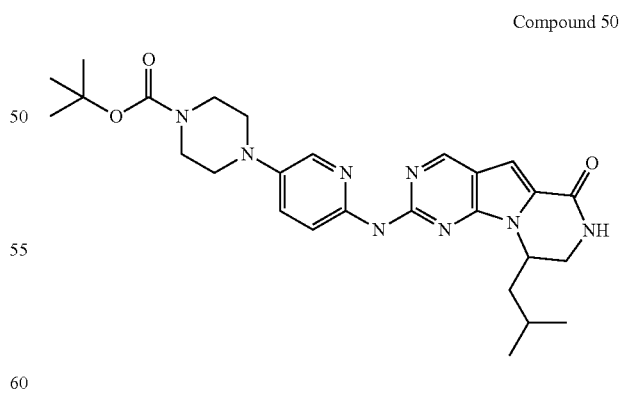

BIOLOGICAL ACTIVITY

Kinase enzymatic reactions were performed in 384-well microplates using a 12-channel Caliper LabChip instrument as a detection device. The enzymatic phosphorylation of a peptide results in a change in net charge, enabling electrophoretic separation of product from substrate. As substrate and product are separated, two peaks of fluorescence are observed. Change in the relative fluorescence intensity of the substrate and product peaks is the parameter measured, reflecting enzyme activity. In the presence of an inhibitor, the ratio between product and substrate is altered. The signal of the product decreases, while the signal of the substrate increases.

For the measurement of CDK2/cyclinE activity, enzyme (0.22 nM) was incubated with 100 mM ATP and the phosphoacceptor substrate peptide (1 mM) for one hour. For the measurement of CDK4/CyclinD activity, enzyme (0.85 nM) was incubated with 200 mM ATP and the phosphoacceptor substrate peptide (1 mM) for three hours. Potential inhibitor compounds (as HCl salts) were tested using 12-point dose response curves in single point at the $K_m$ for ATP. The $IC_{50}$ of each compound was determined using GraphPad Prism. Results from the $IC_{50}$ values demonstrate 200 and 100 fold selectivity for compounds Compound 1 and Compound 3 for Cdk4/CycD1 over Cdk2/CycE respectively. Results are provided in Table 1.

TABLE 1

| Compound | CDK2/cyclinE | | CDK4/cyclinD | |
|---|---|---|---|---|
| | $IC_{50}$ (µM) | Confidence Interval 95% | $IC_{50}$ (µM) | Confidence Interval 95% |
| staurosporine | 0.00393 | 0.000706 | 0.0375 | 0.99 |
| Compound 1 | >100 | | 0.453 | 0.85 |
| Compound 3 | >100 | | 1.05 | 0.78 |

Additional CDK2/cyclinE data is provided in Table 2. $IC_{50}$ data is as follows: A—0.001-0.010 µM; B—0.010-0.100 µM; C—0.100-1 µM; D—1-100 µM; and E—>100 µM. Data is also shown for known CDK4/6 inhibitor, PD0332991.

TABLE 2

| Compound # | CDK2/CycE IC50(µM) | Compound # | CDK2/CycE IC50(µM) |
|---|---|---|---|
| PD0332991 | D | 34 | B |
| 28 | D | 36 | D |
| 27 | D | 35 | D |
| 33 | D | 39 | D |
| 40 | D | 20 | C |
| 17 | D | 19 | E |
| 41 | D | 9 | D |
| 46 | D | 22 | D |
| 29 | D | 18 | E |
| 30 | D | 47 | E |
| 16 | D | 6 | E |
| 48 | E | 21 | D |
| 32 | D | 25 | D |
| 12 | D | 31 | E |
| 10 | D | 24 | D |
| 13 | D | 11 | E |
| 38 | D | 15 | E |
| 23 | C | 7 | E |
| 49 | D | 14 | E |
| 26 | D | 1 | E |
| 8 | D | 3 | E |
| 37 | D | 5 | E |

PHARMACEUTICAL COMPOSITIONS

In one embodiment a pharmaceutical composition comprising compounds of the invention is provided. In a first aspect, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, basic compounds such as free bases. A thorough discussion of pharmaceutically acceptable excipients and salts is available in Remington's Pharmaceutical Sciences, 18th Edition (Easton, Pa.: Mack Publishing Company, 1990).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

The invention claimed is:
1. A compound of formula:

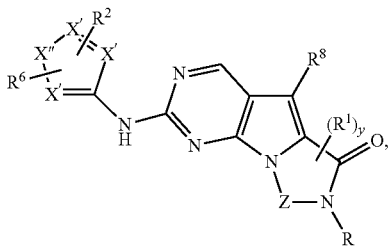

or a pharmaceutically acceptable salt thereof, wherein:
Z is —(CH$_2$)$_x$— wherein x is 1, 2, 3 or 4 or —O—(CH$_2$)$_z$— wherein z is 2, 3 or 4;
each X' is independently, CH or N;
X" is CH$_2$, S or NH;
each of R and R$^8$ are independently H, C$_1$-C$_3$ alkyl or haloalkyl;
each R$^1$ is independently aryl, alkyl, cycloalkyl or haloalkyl, wherein each of said alkyl, cycloalkyl and haloalkyl groups optionally includes O or N heteroatoms in place of a carbon in the chain and two R$^1$'s on adjacent ring atoms or on the same ring atom together with the ring atom(s) to which they are attached optionally form a 3-8-membered cycle;
y is 0, 1, 2, 3 or 4;
R$^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-C(O)—O-alkyl; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring and wherein m is 0 or 1 and n is 0, 1 or 2;
R$^3$ and R$^4$ at each occurrence are independently:
(i) hydrogen or
(ii) alkyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance, and wherein two R$^x$ groups bound to the same or adjacent atom may optionally combine to form a ring; or R$^3$ and R$^4$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;
R$^5$ and R$^{5*}$ at each occurrence is:
(i) hydrogen or
(ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance;
R$^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-O-alkylene-OR$^5$, -(alkylene)$_m$-S(O)$_n$—R$^5$, -(alkylene)$_m$-NR$^3$R$^4$, -(alkylene)$_m$-CN, -(alkylene)$_m$-C(O)—R$^5$, -(alkylene)$_m$-C(S)—R$^5$, -(alkylene)$_m$-C(O)—OR$^5$, -(alkylene)$_m$-O—C(O)—R$^5$, -(alkylene)$_m$-C(S)—OR$^5$, -(alkylene)$_m$-C(O)-(alkylene)$_m$-NR$^3$R$^4$, -(alkylene)$_m$-C(S)—NR$^3$R$^4$, -(alkylene)$_m$-N(R$^3$)—C(O)—NR$^3$R$^4$, -(alkylene)$_m$-N(R$^3$)—C(S)—NR$^3$R$^4$, -(alkylene)$_m$-N(R$^3$)—C(O)—R$^5$, -(alkylene)$_m$-N(R$^3$)—C(S)—R$^5$, -(alkylene)$_m$-O—C(O)—NR$^3$R$^4$, -(alkylene)$_m$-O—C(S)—NR$^3$R$^4$, -(alkylene)$_m$-SO$_2$—NR$^3$R$^4$, -(alkylene)$_m$-N(R$^3$)—SO$_2$—R$^5$, -(alkylene)$_m$-N(R$^3$)—SO$_2$—NR$^3$R$^4$, -(alkylene)$_m$-N(R$^3$)—C(O)—(OR$^5$), -(alkylene)$_m$-N(R$^3$)—C(S)—OR$^5$, or -(alkylene)$_m$-N(R$^3$)—SO$_2$—R$^5$; wherein:
said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^{5*}$, -(alkylene)$_m$-S(O)$_n$—R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)OR$^{5*}$, -(alkylene)$_m$-OC(=O)R$^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO$_2$—NR$^{3*}$R$^{4*}$, -(alkylene)$_m$-N(R$^{3*}$)—SO$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$-N(R$^{3*}$)—C(S)—OR$^{5*}$, or -(alkylene)$_m$-N(R$^{3*}$)—SO$_2$—R$^{5*}$,
n is 0, 1 or 2, and
m is 0 or 1; and
R$^{3*}$ and R$^{4*}$ at each occurrence are independently:
(i) hydrogen or
(ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance; or R$^{3*}$ and R$^{4*}$ together with the nitrogen atom to which they are attached may combine to form a heterocyclo ring optionally independently substituted with one or more R$^x$ groups as allowed by valance; and
R$^6$ is a lower alkyl or absent.
2. The compound of claim 1, wherein R$^8$ is hydrogen or C$_1$-C$_3$ alkyl.
3. The compound of claim 1, wherein R$^2$ is selected from any one of the structures of FIG. 1.
4. The compound of claim 1, wherein R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ any of which may be optionally independently substituted with one or more R$^x$ groups as allowed by valance, and wherein two R$^x$ groups bound to the same or adjacent atom may optionally combine to form a ring.
5. The compound of claim 1, wherein R$^2$ is

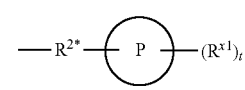

wherein:
R$^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-

(alkylene)$_m$- or -(alkylene)$_m$-NH-(alkylene)$_m$- wherein each m is independently 0 or 1;

P is a 4- to 8-membered mono- or bicyclic saturated heterocyclyl group;

each $R^{x1}$ is independently -(alkylene)$_m$-(C(O))$_m$-(alkylene)$_m$-(N($R^N$))$_m$-(alkyl)$_m$ wherein each m is independently 0 or 1 provided at least one m is 1, —C(O)—O-alkyl, -(alkylene)$_m$-cycloalkyl wherein m is 0 or 1, —N($R^N$)-cycloalkyl, —C(O)-cycloalkyl, -(alkylene)$_m$-heterocyclyl wherein m is 0 or 1, or —N($R^N$)-heterocyclyl, —C(O)-heterocyclyl, —S(O)$_2$-(alkylene)$_m$ wherein:

$R^N$ is H, $C_1$ to $C_4$ alkyl or $C_1$ to $C_6$ heteroalkyl, and wherein two $R^{x1}$ can, together with the atoms to which they attach on P, which may be the same atom, form a ring; and t is 0, 1 or 2.

6. The compound of claim 5, wherein $R^2$ is

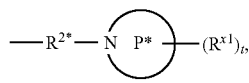

wherein P* is a 4- to 8-membered mono- or bicyclic saturated heterocyclyl group and $R^{2*}$, $R^{x1}$ and t are as previously defined.

7. The compound of claim 5, wherein $R^2$ is

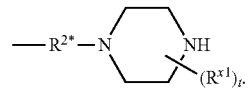

8. The compound of claim 6, wherein $R^2$ is

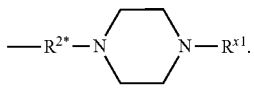

9. The compound of claim 5, wherein each $R^{x1}$ is only optionally substituted by $C_1$-$C_4$ alkyl, halogen or hydroxy.

10. The compound of claim 6, wherein each $R^{x1}$ is only optionally substituted by $C_1$-$C_4$ alkyl, halogen or hydroxy.

11. The compound of claim 7, wherein each $R^{x1}$ is only optionally substituted by $C_1$-$C_4$ alkyl, halogen or hydroxy.

12. The compound of claim 8, wherein each $R^{x1}$ is only optionally substituted by $C_1$-$C_4$ alkyl, halogen or hydroxy.

13. The compound of claim 1, wherein $R^2$ is

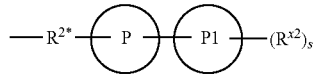

wherein:

$R^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- or -(alkylene)$_m$-NH-(alkylene)$_m$- wherein each m is independently 0 or 1;

P is a 4- to 8-membered mono- or bicyclic saturated heterocyclyl group;

P1 is a 4- to 6-membered monocyclic saturated heterocyclyl group;

each $R^{x2}$ is independently hydrogen or alkyl; and s is 0, 1 or 2.

14. The compound of claim 13, wherein $R^2$ is

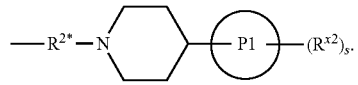

15. The compound of claim 1, wherein $R^x$ is not further substituted.

16. The compound of claim 5, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

17. The compound of claim 6, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

18. The compound of claim 7, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

19. The compound of claim 8, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

20. The compound of claim 9, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

21. The compound of claim 10 wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

22. The compound of claim 11 wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

23. The compound of claim 12, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

24. The compound of claim 13, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

25. The compound of claim 14, wherein $R^{2*}$ is an alkylene, -(alkylene)m-O-(alkylene)m-, -(alkylene)m-C(O)-(alkylene)m-, -(alkylene)m-S(O)2-(alkylene)m- or -(alkylene)m-NH-(alkylene)m- wherein each m is independently 0 or 1, and wherein any alkylene is not further substituted.

26. The compound of claim 1, wherein R is hydrogen or $C_1$-$C_3$ alkyl.

27. The compound of claim 4, wherein the alkylene in $R^2$ is methylene.

28. The compound of claim 5, wherein the alkylene in $R^2$ is methylene.

29. The compound of claim 13, wherein the alkylene in $R^2$ is methylene.

30. The compound of claim 1, wherein $R^2$ is -(alkylene)m-heterocyclo or -(alkylene)m-heteroaryl,
R is hydrogen, and,
X' is independently CH or N.

31. The compound of claim 30, wherein $R^2$ is -(alkylene)m-heterocyclo.

32. The compound of claim 30, wherein m is 0.

33. The compound of claim 31, wherein m is 0.

34. The compound of claim 30, wherein m is 1.

35. The compound of claim 31, wherein m is 1.

36. The compound of claim 30, wherein the heterocyclo is not substituted.

37. The compound of claim 31, wherein the heterocyclo is not substituted.

38. The compound of claim 30, wherein $R^2$ is

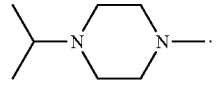

39. A pharmaceutical composition comprising the compound of claim 1, or a pharmaceutically acceptable salt thereof.

40. The compound of claim 1, wherein $R^2$ is selected from any one of the structures of FIG. 2.

41. The compound of claim 1, wherein $R^2$ is selected from any one of the structures of FIG. 3.

42. The compound of claim 1, wherein $R^6$ is absent.

* * * * *